(12) United States Patent
Levine et al.

(10) Patent No.: US 7,396,533 B2
(45) Date of Patent: Jul. 8, 2008

(54) POLYPEPTIDES AND NUCLEIC ACIDS ENCODING SAME

(75) Inventors: Arnold J. Levine, New York City, NY (US); Diane Pennica, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 479 days.

(21) Appl. No.: 10/628,770

(22) Filed: Jul. 28, 2003

(65) Prior Publication Data

US 2004/0132052 A1    Jul. 8, 2004

Related U.S. Application Data

(63) Continuation of application No. 09/182,562, filed on Oct. 29, 1998, now abandoned.

(60) Provisional application No. 60/073,612, filed on Feb. 4, 1998, provisional application No. 60/063,704, filed on Oct. 29, 1997.

(51) Int. Cl.
*A61K 39/385* (2006.01)
*C12N 9/14* (2006.01)
*C07K 14/435* (2006.01)

(52) U.S. Cl. .............. 424/193.1; 424/184.1; 424/185.1; 424/192.1; 424/178.1; 530/350; 435/195

(58) Field of Classification Search ................. 530/300, 530/350, 402; 424/184.1, 185.1, 192.1, 193.1, 424/178.1; 435/195
See application file for complete search history.

(56) References Cited

U.S. PATENT DOCUMENTS

| | | | |
|---|---|---|---|
| 5,408,040 | A | 4/1995 | Grotendorst et al. |
| 5,536,637 | A | 7/1996 | Jacobs |
| 5,585,087 | A | 12/1996 | Lustig et al. |
| 5,840,569 | A | 11/1998 | Hillman |
| 6,100,060 | A | 8/2000 | Barnes et al. |

FOREIGN PATENT DOCUMENTS

| | | |
|---|---|---|
| EP | 307247 | 3/1989 |
| WO | WO 89/06692 | 7/1989 |
| WO | WO 95/17416 | 6/1995 |
| WO | WO 98/21236 | 5/1998 |
| WO | WO 98/25956 | 6/1998 |
| WO | WO 02/088081 | 11/2002 |

OTHER PUBLICATIONS

Kirkoshi, H. et al., International Journal of Oncology, 20: 777-783, 2002.*
McClean and Hill, Eur J of Cancer, 1993, vol. 29A, pp. 2243-2248.*
Saras, J. et al., Experimental cell Research, 299: 356-369, 2004.*
Bowie et al, Science, 247: 1306-1310, 1990.*
Burgess et al, J. Cell Biology, 111 : 2129-2138, 1990.*
Lazar et al, Molecular and Cellular Biology, 8: 1247-1252, 1988.*
Chuang, Y.-y., et al, Journal of Cell Science, 120: 1927-1934, 2007.*
Bost, et al., "The JUN Kinase/Stress-activated Protein Kinase Pathway is Required for Epidermal Growth Factor Stimulation of Growth of Human A549 Lung Carcinoma Cells", The Journal of Biological Chemistry, 272(52); 33422-33429 (1997).
Carter, et al., "Pak-1 Expression Increases with Progression of Colorectal Carcinomas to Metastasis", Clinical Cancer Research 10:3448-3456 (2004).
Kumar, et al., "p21-activated Kinases in Cancer", Nature Reviews/Cancer, 6:459471 (2006).
O'Hagan, et al., "The PEA3 Ets Transcription Factor is a Downstream Target of the HER2/Neu Receptor Tyrosine Kinase", Oncogene 16:301-310 (1998).
Potapova, et al., "Targets of c-Jun $NH_2$-terminal Kinase 2-mediated Tumor Growth Regulation Revealed by Serial Analysis of Gene Expression", Cancer Research 62:3257-3263 (2002).
Taneyhill, et al., "Identification of Wnt Responsive Genes Using a Murine Mannary Epithelial Cell LIne Model System", BMC Developmental Biology, 4:6 (2004).
Tao, et al., *Wrch-1*, a Novel Member of the Rho Gene Family that is Regulated by Wnt-1, Genes & Development 15:1796-1807 (2001).
Adams et al., "Initial assessment of human gene diversity and expression patterns based upon 83 million nucleotides of cDNA sequence" *Nature* 377(6547 SUPPL):3-174 (1995).
Adams, MD et al., "EST90040 Synovial membrane *Homo sapiens* cDNA 5' end " *Database EMBL-EMESTI8, Entry Hszz82583, Acc. No. AA377456*, Apr. 21, 1997.
Alitalo and Schwab, "Oncogene amplification in tumor cells" *Advances in Cancer Research* 47:235-281 (1986).
Altschul and Gish, "Local Alignment Statistics" *Methods in Enzymology* 266:460-480 (1996).
Attisano et al., "TGF-beta receptors and actions" *Biochemica et Biophysica Acta* 1222(1):71-80 (May 26, 1994).
Augenlicht, LH et al, "Low-level c-myc amplification in human colonic carcinoma cell lines and tumors: a frequent, p53-independent mutation associated with improved outcome in a randomized multi-institutional trial" *Cancer Research* 57(9):1769-1775 (May 1, 1997).
Ausubel et al. *Current Protocols in Molecular Biology*, N.Y.:Green Publishing Associates and Wiley Interscience (1989).
Babic AM et al., "CYR61, a product of a growth factor-inducible immediate early gene, promotes angiogenesis and tumor growth" *Proc. Natl. Acad. Sci. USA* 95(11):6355-6360 (May 26, 1998).
Baker, N., "Embryonic and imaginal requirements for wingless, a segment-polarity gene in Drosophila" *Dev. Biol.* 125:96-108 (1988).
Barfod et al., "Cloning and expression of a human CDC42 GTPase-activating protein reveals a functional SH3-binding domain" *Journal of Biological Chemistry* 268(35):26059-26062 (Dec. 15, 1993).

(Continued)

*Primary Examiner*—Alana M. Harris
*Assistant Examiner*—Anne L. Holleran
(74) *Attorney, Agent, or Firm*—Traci Ropp; Ginger R. Dreger, Esq.; Goodwin Procter LLP

(57) ABSTRACT

DNAs are provided, whose genes are induced at least by Wnt-1. Also provided are nucleic acid molecules encoding those polypeptides, as well as vectors and host cells comprising those nucleic acid sequences, chimeric polypeptide molecules comprising the polypeptides fused to heterologous polypeptide sequences, antibodies which bind to the polypeptides, and methods for producing the polypeptides.

4 Claims, 23 Drawing Sheets

OTHER PUBLICATIONS

Baselga et al., "HER2 Overexpression and Paclitaxel Sensitivity in Breast Cancer: Therapeutic Implications" *Oncology* (Supplement No. 2) 11(3):43-48 (Mar. 1997).

Baselga et al., "Phase II Study of Weekly Intravenous Recombinant Humanized Anti-p185$^{HER2}$ Monoclonal Antibody in Patients With HER2/neu-Overexpressing Metastatic Breast Cancer" *J. Clin. Oncol.* 14(3):737-744 (Mar. 1996).

Beier et al, "MDB0332 Mouse brain, Stratagene Mus musculus cDNA 3' end similar to proto-ocogene (Wnt-5a) (human)" *Database EMBL-EMEST19, Entry MM953, Acc. No. R74953* Jul. 25, 1996.

Bennett et al., "Extracellular Domain-IgG Fusion Proteins for Three Human Natriuretic Peptide Receptors. Hormone Pharmacology and Application to Solid Phase Screening of Synthetic Peptide Antisera" *The Journal of Biological Chemistry* 266(34):23060-23067 (1991).

Bishop, J., "Molecular themes in oncogenesis" *Cell* 64(2):235-248 (Jan. 25, 1991).

Bolivar, "Construction and characterization of new cloning vehicles. II. A multipurpose cloning system" *Gene* 2(2):95-113 (1997).

Boring et al., "Cancer Statistics, 1993" *CA: A Cancer Journal for Clinicians* 43(1):7-26 (Jan.-Feb. 1993).

Bradbury et al., "Wnt-4 expression induces a pregnacy-like growth pattern in reconstituted mammary glands in virgin mice" *Dev. Biol.* 170:553-563 (1995).

Bradley and Brown, "The proto-oncogene int-1 encodes a secreted protein associated with the extracellular matrix" *EMBO Journal* 9:1569-1575 (1990).

Bradley, RS et al., "Expression of Wnt-1 in PC-12 cells results in modulation of plakoglobin and E-cadherin and increased cellular adhesion" *Journal of Cell Biology* 123(6, Pt.2): 1857-1865 (Dec. 1993).

Brown, et al., "A retrovirus vector expressing the putative mammary oncogene int-1 causes partial transformation of mammary epithelial cell line" *Cell* 46(7):1001-1009 (Sep. 26, 1986).

Brown, "Characterization of the Functional gene and several processed pseudogenes in the human triosephosphate isomerase gene family" *Mol. Cell Biol* 5(7):1694-1706 (Jul. 1985).

Cadigan and Nusse, "Wnt signaling: a common theme in animal development" *Genes & Development* 11(24):3286-3305 (Dec. 15, 1997).

Christiansen et al., "Murine Wnt-11 and Wnt-12 have temporally and spatially restricted expression patterns during embryonic development" *Mech. Dev.* 51(2-3):341-350 (1995).

Cornelis et al., "Allele loss patterns on chromosome 17g in 109 breast carcinomas indicate at least two distinct target regions" *Oncogene* 8(3):781-785 (Mar. 1993).

Cropp et al., "Loss of heterozygosity on chromosome 17 and 18 in breast carcinoma: two additional regions identified" *Proc. Natl. Acad. Sci. USA* 87(19):7737-7741 (Oct. 1990).

Darzynkiewicz et al., "Features of apoptotic cells measured by flow cytometry" *Cytometry* 13(8):795-808 (1992).

Diatchenko et al., "Suppression subtractive hybridization: a method for generating differentially regulated or tissue-specific cDNA probes and libraries" *Proc. Natl. Acad. Sci. USA* 93:6025-6030 (1996).

Didsbury et al., "rac, a novel ras-related family of proteins that are botulinum toxin substrates" *Journal of Biological Chemistry* 264(28):16378-16382 (Oct. 5, 1989).

Dzierzak and Medvinsky, "Mouse embryonic hematopoiesis" *Trends Genet.* 11:359-366 (1995).

Fendly, B.M. et al., "Characterization of Murine Monoclonal Antibodies Reactive to Either the Human Epidermal Growth Factor Receptor or HER2/neu Gene Product" *Cancer Research* 50:1550-1558 (Mar. 1, 1990).

Fracker PJ, et al., "Protein and cell membrane iodinations with sparingly soluble chloroamide, 1,3,4,6-tetrachloro-3a,6a-dephrenylglycoluril" *Biochem Biophys Res Commun* 80(4):849-857 (Feb. 28, 1978).

Gavin et al., "Expression of multiple novel Wnt-1/int-1-related genes during fetal and adult mouse development" *Genes Dev.* 4:2319-2332 (1990).

Glinka et al., "Dickkopf-1 is a Member of a New Family Secreted Proteins and Functions in Head Induction." *Nature.* 391(6665):357-362 (Jan. 22, 1998).

Godowski, et al., "Characterization of the human growth hormone receptor gene and demonstration of a partial gene deletion in two patients with Laron-type dwarfism" *Proc. Natl. Acad. Sci. USA* 86:8083-8087 (1989).

Haataja et al., "Characterization of RAC3, a novel member of the Rho family" *Journal of Biological Chemistry* 272(33):20384-20388 (Aug. 15, 1997).

Hashimoto et al., "Expression of the Elml gene, a novel gene of the CCN (connective tissue growth factor, Cyr61/Cef10, and neuroblastoma overexpressed gene) family, suppresses In vivo tumor growth and metastasis of K-1735 murine melanoma cells" *Journal of Experimental Medicine* 187(3):289-296 (Feb. 2, 1998).

Herman and Horvitz, "The Caenorhabditis elegans gene lin-44 controls the polarity of asymmetric cell divisions" *Development* 120:1035-1047 (1994).

Hiller et al. (GenBank EST accession No. AA133248) (Nov. 1996).

Hiller et al., "z117h12.r1 Soares pregnant uterus NbHPU Homosapiesn cDiens cDNA clone 502247 5' [C [C [C'" *Database EMBL-EMEST15, Entry Hsaa33248, Acc. No. AA133248,* Nov. 27, 1996.

Hiller, "yb42e03.rl Homo sapiens cDNA clone 73852 5'" *Database EMBL-EMEST10, Entry HSO1627, Acc. No. T55016,* Feb. 6, 1995.

Holland et al., "Gene duplications and the origins of vertebrate development" *Development—Supplement* pp. 125-133 (1994).

Holmes et al., "Structure and Functional Expression of a Human Interleukin-8 Receptor" *Science* 253(5025):1278-1280 (1991).

Hunter, T., "Cooperation between oncogenes" *Cell* 64(2):249-270 (Jan. 25, 1991).

Hynes and Stern., "The Biology of erbB-2/neu/HER-2 and its Role in Cancer." *Biochimica et Biophysica Acta* 1198(2-3):165-184 (Dec. 30, 1994).

Jue et al., "The mouse Wnt-1 gene can act via a paracrine mechanism in transformation of mammary epithelial cells" *Molecular & Cellular Biology* 12(1):321-328 (Jan. 1992).

Kanatsu and Nishikawa, "In vitro analysis of epiblast tissue potency for hematopoietic cell differentiation" *Development* 122:823-830 (1996).

Kay et al., "Xenopus laevis: Practical uses in Cell and Molecular Biology" *Methods in Cell Biology* 36. (1991).

Kearney JF et al, "A new mouse myeloma cell line that has lost immunoglobulin expression but permits the construction of antibody-secreting hybrid cell lines" *J. Immunol* 123(4):1548-1550 (Oct. 1979).

Kim et al., "Identification of family of low-affinity insulin-like growth factor binding proteins (IGFBPs): Characterization of connective tissue growth factor as a member of the IGFBP superfamily" *Proc. Natl. Acad. Sci. USA* 94(24):12981-12986 (Nov. 25, 1997).

Klein et al., "Selection for Genes Encoding Secreted Proteins and Receptors" *Proc. Natl. Acad. Sci. USA* 93(14):7108-7113 (1996).

Klingensmith and Nusse, "Signaling by wingless in Drosophila" *Dev. Biol.* 166:396-414 (1994).

Lee et al., "Insertional mutagenesis identifies a member of the Wnt gene family as a candidate oncogene in the mammary epithelium of int-2/Fgf-3 transgenic mice" *Proc. Natl. Acad. Sci.* 96(6):2268-2272 (1995).

Lu and Gillett, "An Optimized Protocol for In Situ Hybridization Using PCR-Generated $^{33}$P-Labeled Riboprobes." *Cell Vision.* 1(2):169-176 (1994).

Maquat LE et al., "Human triosephosphate isomerase cDNA and protein structure. Studies of triosephosphate isomerase deficiency in man" *J Biol Chem* 260(6):3748-3753 (Mar. 25, 1985).

Marra et al., "md87all.rl Soares mouse embryo NbME13.5 14.5 Mus musculus cDNA clone 375356 5'" *Database EMBL-MM71928, Entry MM71928, Acc. No. W64719,* Jun. 10, 1996.

Marra et al., "me63e12.rl Soares mouse embryo NbME13.5 14.5 Mus musculus cDNA clone 400270 5'" *Database EMBL-EMEST19, Entry MM22832, Acc. No. W77228,* Jun. 20, 1996.

Marra M et al, "va79b05.rl Soares mouse NML Mus musculus cDNA clone 737553 5'" *Database EMBL-EMEST18, Entry MM1181119, Acc. No. AA277108,* Apr. 1, 1997.

Marra M et al., "mw97e08.r1 Soares mouse NML Mus musculus cDNA clone 678662 5'" *Database EMBL-EMEST18, Entry MM1155850, Acc. No. AA238083*, Mar. 3, 1997.

Marra M et al., "ug99b06.r1 Soares mouse hypothalamus NMHy Mus musculus cDNA clone 1616531 5', mRNA sequence" *Database EMBL-EMEST5, Entry/acc. No. Aa981401*, May 27, 1998.

Marra M et al., "vc34c10.r1 Barstead MPLRB1 Mus musculus cDNA clone 776466 5'" *Database EMBL-EMEST18, Entry MM1182282. Acc. No. AA278092*, Apr. 1, 1997.

Marra M et al., "vu05a03.r1 Soares mouse mammary gland NbMMg Mus musculus cDNA clone 1179724 5' similar to SW:G25B human P21181 G25K GTP-binding protein, brain isoform" *Database EMBL-EMEST2. Entry/acc. No. Aa672834*, Nov. 26, 1997.

Marra, M et al., "mg36a12.r1 Soares mouse embryo NbME13.5 14.5 Mus Musculus cDNA clone 425854 5'" *Database EMBL-EMEST19, Entry MMA00708, Acc. No. AA000708*, Jul. 18, 1996.

Marra, M et al., "mi41b01.r1 Soares mouse embryo NbME13.5 14.5 Mus musculus cDNA clone 466057 5'" *Database EMBL-EMEST19, Entry mma34677, Acc. No. AA034677* (es), Aug. 23, 1996.

Marra, M et al., "mj41h08.r1 Soares mouse embryo NbME13.5 14.5 Mus musculus cDNA clone 478719 5'" *Database EMBL-EMEST19, Entry MMAA51212, Acc. No. AA051212*, Sep. 9, 1996.

Martinerie C, et al., "Physical mapping of human loci homologous to the chicken nov proto-oncogene" *Oncogene* 7(12):2529-2534 (Dec. 1992).

Martinerie et al., "Regulation of nov by WT1: a potential role for nov in nephrogenesis" *Oncogene* 12(7): 1479-1492 (Apr. 4, 1996).

Martinerie et al., "Structural analysis of the human nov proto-oncogene and expression in Wilms tumors" *Oncogene* 9(9):2729-2732 (Sep. 1994).

McMahon and Bradley, "The Wnt-1 (int-1) proto-oncogene is required for development of a large region of the mouse brain" *Cell* 62:1073-1085 (1990).

McMahon, A., "The Wnt Family of Developmental Regulators" *Trends in Genetics* 8(7):236-242 (1992).

Meese, "Molecular mapping of the oncogene MYB and rearrangements in malignant melanoma" *Genes Chromosomes Cancer* 1(1):88-94 (Sep. 1989).

Moll et al., "The murine rac1 gene: cDNA cloning, tissue distribution and regulated expression of rac1 mRNA by disassembly of actin microfilaments" *Oncogene* 6(5):863-866 (May 1991).

Morata and Lawrence, "The develoment of wingless, a homeotic mutation of Drosophila" *Dev. Biol.* 56:227-240 (1977).

Nieuwkoop et al, "Normal Table of Xenopus laevis: (Daudin)", Amsterdam: North—Holland (1967).

Nusse and Varmus, "Many tumors induced by the mouse mammary tumor virus contain a provirus integrated in the same region of the host genome" *Cell* 31:99-109 (1982).

Nusse and Varmus, "Wnt genes" *Cell* 69:1073-1087 (1992).

O'Reilley et al. *Baculovirus Expression Vectors: A Laboratory Manual*, Oxford: Oxford University Press (1994).

Oemar and Luscher, "Connective tissue growth factor. Friend or foe?" *Arteriosclerosis, Thrombosis & Vascular Biology* 17(8):1483-1489 (Aug. 1997).

Olson and Papkoff, "Regulated expression of Wnt Family Members duirng Proliferation of C57mg Mammary Cells" *Cell Growth & Differentiation* 5(2):197-206 (Feb. 1994).

Papkoff and Schryver, "Secreted int-1 protein is associated with the cell surface" *Mole. Cell. Biol.* 10:2723-2730 (1990).

Parr and McMahon, "Dorsalizing signal Wnt-7a required for normal polarity of D-V and A-P axes of mouse limb" *Nature* 374:350-353 (1995).

Pennica D, et al., "WISP genes are members of the connective tissue factor family that are up-regulated in wnt-1-transformed cells and aberrantly expressed in human colon tumors" *Proc. Natl. Acad. Sci. USA* 95(25):1471-14722 (Dec. 8, 1998).

Picker et al., "Control of lymphocyte recirculation in man. I. Differential regulation of the perpheral lymph node homing.receptor L-selectin on T cells during the virgin to memory cell transition" *Journal of Immunology* 150(3):1105-1121 (Feb. 1, 1993).

Possee R.D. et al., "Nucleotide sequence of the Autographa californica nuclear polyhedrosis 9.4 kbp EcoRI-I and -R(polyhedrin gene) region" *Virology* 185(1):229-241 (1991).

Price et al., "Tumorigenicity and metastasis of human breast carcinoma cell lines to nude mice" *Cancer Research* 50(3):717-721 (Feb. 1, 1990).

Ravdin and Chamness, "The c-erbB-2 proto-oncogene as a prognostic and predictive marker in breat cancer: a paradigm for the development of other macromolecular markers—a review" *Gene* 159(1):19-27 (Jun. 14, 1995)

Rijsewijk et al., "The Drosophila homolog of the mouse mammary oncogene int-1 is identical to the segment polarity gene wingless" *Cell* 50:649-657 (1987).

Ruppert et al., "Cloning and Expression of Human $TAF_{II}250$: a TBP-associated Factor Implicated in Cell-cycle Regulation" *Nature* 362:175-179 (1993).

Sambrook et al, "Molecular Cloning: A Laboratory Manual", Cold Spring Harbor Laboratory Press, New York (1989).

Schwab and Amler, "Amplification of cellular oncogenes: a predictor of clinical outcome in human cancer" *Genes, Chromosomes & Cancer* 1(3):181-193 (Jan. 1990).

Shirsat et al., "A member of the ras gene superfamily is expressed specifically in T, B and myeloid hempoietic cells" *Oncogene* 5(5):769-772 (May 1990).

Sigel M., et al., "Production of Antibodies by Inoculation into Lymph Nodes" *Methods in Enzymology*, New York: Academic Press vol. 93 (1983).

Slamon et al., "Human Breast Cancer: Correlation of Relapse and Survival with Amplification of the HER-2/neu Oncogene" *Science* 235:177-182 (Jan. 9, 1987).

Slamon et al., "Studies of the HER-2/neu Proto-Oncogene in Human Breast and Ovarian Cancer" *Science* 244:707-712 (May 12, 1989).

Sokol S, et al., "Injected Wnt RNA induces a complete body axis in Xenopus embryos" *Cell* 67(4):741-752 (Nov. 15, 1991).

Sompayrac et al., "Efficient infection of monkey cells with DNA of simian virus 40" *Proc. Natl. Acad. Sci. USA* 78(12):7575-7578 (Dec. 1981).

Stark et al., "Epithelial transformation of metanephric mesenchyme in the developing kidney regulated by Wnt-4" *Nature* 372:679-683 (1994).

Strausberg, R., "nn03e01.s1 NCI_CGAP_Pr4.1 *Homo sapiens* CDNA clone IMAGE:1076664 similar to TR:g984956 G984956 connective tissue growth factor" *Database EMBL-EMEST1, Entry Aa592984, Acc. No. AA592984*, Sep. 12, 1997.

Suva et al., "A parathyroid hormone-related protein implicated in malignant hypercalcemia: cloning and expression" *Science* 237(4817):893-896 (Aug. 1987).

Suva, L.J. et al., "A Parathyroid Hormone-Related Protein Implicated in Malignant Hypercalcemia: Cloning and Expression" *Science* 237:893-896 (1987).

Takada et al., "Wnt-3a regulates somite and tailbud formation in the mouse embryo" *Genes Dev.* 8:174-189 (1994).

Takahashi, "Mapping of the MYC gene to band 8q24.12—q24.13 by R-banding and distal to fra (8) (q24.11), FRA8E, by fluorescence in situ hybridization" *Cytogenet Cell Genet* 57(2):109-111 (1991).

Thimmappaya et al., "Andenovirus VAI RNA is required for efficient translation of viral mRNAs at late times after infection" *Cell* 31(3 Pt 2):543-551 (Dec. 1982).

Thomas and Cappechi, "Targeted disruption of the murine int-1 proto-oncogene resulting in severe abnormalities in midbrain and cerebellar development" *Nature* 346:847-850 (1990).

Tubby, B., "*Homo sapiens* DNA sequence from PAC 142L7 on chromosome 6q21. Contains a . . . Connective Tissue growth factor" *Database EMBL-EMHUM1, Entry Hs14217, Acc. No. Z99289*, May 30, 1998.

Van't Veer, "molecular cloning and chromosomal assignment of the human homolog of int-1, a mouse gene implicated in mammary tumorigenesis" *Mol Cell Biol* 4(11):2532-2534 (Nov. 1984).

Vant Veer et al., "Molecular cloning and chromosomal assignment of the human homolog of int-1, a mouse gene implicated in mammary tumorigenesis" *Mole. Cell. Biol.* 4:2532-2534 (1984).

Wong et al., "Differential transformation of mammary epithelial cells by Wnt genes" *Molecular & Cellular Biology* 14(9):6278-6286 (Sep. 1994).

Yamanaka et al., "Inhibition of insulin receptor activation by insulin-like growth factor binding proteins" *Journal of Biological Chemistry* 272(49):30729-30734 (Dec. 5, 1997).

Zhang et al., "Relative malignant potential of human breast carcinoma cell lines established from pleural effusions and a brain metastasis" *Invasion Metastasis* 11(4):204-215 (1991).

Zhang R et al., "Identification of rCop-1, a new member of the CCN protein family, as a negative regulator for cell transformation" *Mol Cell Biol* 18(10):6131-6141 (Oct. 1998).

Zheng S et al, "The induction of Wnt-1 in PC12 cells reults in modulation of plakoglobin and E-cadherin and increased cellular adhesion" *Journal of Cell Biology* 123 (6,pt2):1857-1865 (Dec. 1993).

Zheng S et al., "The induction of ret by Wnt-1 in PC12 cells is atypically dependent on continual Wnt-1 expression" *Oncogene* 12(3):555-562 (Feb. 1996).

Zon et al., "The zebrafish: a new model for studying embryonic hematopoiesis" *Collogue, INSERM*, Gluckman and Coulombel, eds. vol. 235:17-22 (1995).

Zon, et al.,, "in Gluckman and Coulombel, ed., Colloque, ISERM" *presented at the Joint International Workshop on Foetal and Neonatal Hematopoisis and Mechanism of Bone Marrow Failure*, Paris, France, Apr. 3-6, 1995 235:17-22 (1995).

\* cited by examiner

FIG._1A

```
  1 ATGGCCCCGC AGCAAGGCCG GCCGGCGCTG CCCGCGCCGCT GCGAGCCGCG CCGGTACCGC GGCGGGGGGG GGCGGGGCGC
    TACCGGGGCG TCGTTCCGGC CGGCCGCGAC GGGCGCGGCGA CGCTCGGCGC GGCCATGGCG CCGCCCCCC  CCGCCCCCGG
  1 M A P Q   Q G R   P A L    P A R C    E P P     A A P    P V P P    R R E    R G G      R G A R

101 GCGGGCCCGG GGTGTCCGGG GGTCGGGGGC GCGGGAGGGA CGCGGCGTCA AGTGCGTGCT GGTCGGCGAC CTGTAGATGG GCGGCCTGTG
    CGCCCGGGCC CCACAGGCCC CCAGCCCCCG CGCCCCTCCT GCGCCGCAGT TCACGCACGA CCAGCCGCTG GACATCTACC CGCCGGACAC
 35 G P G   V S G    G R G R     A G G     A E G     R G V K    C V L     V G D    G A V G    K T S

201 CCTGGTGGTC AGCTACACCA CTAACGGCTA TACATCCCTA CGGCCTTCGA CAACTTCTCG GCCGTGGTGT CGGCCACCAA GACATCTACC CGCCGGACAC
    GGACCACCAG TCGATGTGGT GATTGCCGAT ATGTAGGGAT GCCGGAAGCT GTTGAAGAGC CGGCACCACA GACATCTACC CGCCGGACAC
 68 L V V   S Y T T   N G Y    P T E     Y I P T    A F D     N F S    A V V S    V D G     R P V

301 AGACTCCAGC TCTGTGACAC TGCAGGACAG GATGAGTTTG ACAAGCTGAG GCCCCTCTGC TACACCAACA CAGACATCTT CCTGCTGTGC TTCAGCGTGG
    TCTGAGGTCG AGACACTGTG ACGTCCTGTC CTACTCAAAC TGTTCGACTC CGGGGAGACG ATGTGGTTGT GTCTGTAGAA GGACGACACG AAGTCGCACC
101 R L Q L    C D T    A G Q    D E F D    K L R    P L C     Y T N T   D I F    L L C     F S V V

401 TGAGCCCCAC ATCCTTCCAG AGAAGTGGGT TCCAGAGATT CGACGTCACT GCCAAAGGC  CCCCATCATC CTGGTCGGGA CACAGTCGGA
    ACTCGGGGTG TAGGAAGGTC TCTTCACCCA AGGTCTCTAA GCTGCAGTGA CGGGTTTCCG GGGGTAGTAG GACCAGCCCT GTGTCAGCCT
135 S P T   S F Q    N V G E    P E I     R R H C   P K A    P I I    L V G T    Q S D

501 CCTCAGGGAG GACGTCAAAG TGCTCATAGA ACTGGACAAG TGCAAAGAGA AGCCGGTGCC TGAAGAGGCG GCGGAGCTGT GCGCGGAGA AGTCAAAGCT
    GGAGTCCCTC CTGCAGTTTC ACGAGTATCT TGACCTGTTC ACGTTTCTCT TCGGCCACGG ACTTCTCCGC CGCCTCGACA CGCGCCTCCT TCAGTTCGA
168 L R E   D V K V    L I E    L D K    C K E K    P V P    E E A     A K L C    A E E     V K A

601 GTCTCCTACA TCGAGTGCTC AGCCGTTGACT CAGAAAAACC TCAAAGAGGT TTTCGACGCC GCCATTGTTG CTGGTATCCA GACACTCAGAC TCCCAGCTAC
    CAGAGGATGT AGCTCACGAG TCGGCAACTGA GTCTTTTTGG AGTTTCTCCA AAAGCTGCGG CGGTAACAAC GACCATAGGT CGTGAGTCTG AGGGTCGATG
201 V S Y I    E C S    A L T    Q K N L    K E V    F D A     A I V A   G I Q     H S D    S Q L Q

701 AGCCAAAGAA GTCTAAAAGC AGGACCCCGG ATAAGGTGCG GGACCTGTCC AAGTCTTGGT GGAGGAAGTA TTGCTGCCTG CGCAAATAGC
    TCGGTTTCTT CAGATTTCG TCCTGGGGCC TATTCCACGC CCTGGACAGG TTCAGAACCA CCTCCTTCAT AACGACGGAC GCGTTTATCG
235 P K K   S K S    R T P D    K V R     D L S    K S W W    R K Y    C C L     A Q

801 AGGTGTTTAA GCTGCAACAG CTCTTTATGG ACGAGGCTGT CATAGGATGA GCCCTTAACT TCCTGTGTGC GGGAGCTTAG
    TCCACAAATT CGACGTTGTC GAGAAATACC TGCTCCTACT GTATCCTACT CGGGAATTGA AGGACACACG CCCTCGAATC
268 V F K    L Q Q    L F M    D E A V    I G *

901 GGCTGAGATT CATATGCAAA ATACGTTTTT TTAAAAATTG AAAGTTACAT TTTTTTCTG TTAAGTCTGG AAGCTTTGAG CTGTAGACCT CCGGATTAAT
    CCGACTCTAA GTATACGTTT TATGCAAAAA AATTTTTAAC TTTCAATGTA AAAAAAGAC AATTCAGACC TTCGAAACTC GACATCTGGA GGCCTAATTA
```

```
1001  TTATATTCCA TATGAAAAGG GCTCTTCAAA GCGGGGTGTC AGCATGAAGT TCTGCTGTGT TGTACAGGAC AAAGGAGAAT GAATGGGACC TTCTCCTGAT
      AATATAAGGT ATACTTTTCC CGAGAAGTTT CGCCCCACAG TCGTACTTCA AGACGACACA ACATGTCCTG TTTCCTCTTA CTTACCCTGG AAGAGACTA

1101  TAAGGGCTAC TGAGGGCTCA ATTCCCGATG ACTCCCGAGT CGTGCAGGCA CGTGTGCACC AGGCTTGGTG AGAGTGAGCA AGCGTGAGCT TTGAAACCAC ACGAGCCACC CCCGGTTTG
      ATTCCCGATG ACTCCCGAGT TGTCAGGGCA CACGTCCCGT GCACAGCACC GCACACGTGG TCCGAACCAC TCTCACTCGT TCGCACTCGA AACTTTGGTG TGCTCGGTGG GGGCCAAAAC

1201  TAAGGGCAAA GATCTGAAAC CAGCAAGGGC CTTCTGCTTA CGAAACCTCG AGCCCATCCC TTCTGTTTAC TCAGATTCTC TTAGGATTTT AAAACAACCA
      ATTCCCGTTT CTAGACTTTG GTCGTTCCCG GAAGACGAAT GCTTTGGAGC TCGGGTAGGG AAGACAAATG AGTCCTAAGA AATCCTAAAA TTTTGTTGGT

1301  AACATCCCAC AGCCTACTGG GCGAACAGTG CACTTGCTTG GTTTTGTTTT TTTAAATCAC GTGACCAGTT ATATTGCTAT
      TTGTAGGGTG TCGGATGACC CGCTTGTCAC GTGAACGAAC CAAAACAAAA AAATTTAGTG CACTGGTCAA TATAACGATA

1401  GAAAATGGTG GAGATGCCTC GTAGAAGCGC AGTGCTGGGT GCACATGTGA CATTTCTTTC AGGGAGCGAC TCATGGTGAG ACCAGAGAGG GCTCTTAGCT
      CTTTACCAC CTCTACGGAG CATCTTCCGC TCACGACCCA CGTGTACACT GTAAAAGAAG TCCCCTCGCG AGTACCACTC TGGTCTCTCC CGAGAATCGA

1501  TGCAGGACTG GCTTCTGCAG GGCATCTGTG TCCTGCTGTT AAAAGCAGGA GGAGGTGCTT GTCTGGGAGC TTTAAGTGTG CTGGGCTCAT ATCGTCCCGT
      ACGTCCTGAC CGAAGACGTC CCGTAGACAC AGGACGACAA TTTTCGTCCT CCTCCACGAA CAGAGCTTCG AAATTCACAC GACCCGAGTA TAGCAGGCA

1601  TTGCAAGGAA TTGGGCCACC ATAGTTGATG GCTATGGGAC ACACACACAC TTTTTCCTTA AGTCCACCAA AATGCCTGCC TGTACACACA
      AACGTTCCTT AACCCGGTGG TATCAACTAC CGATACCCTG TGTGTGTGTG AAAAAGGAAT TCAGGTGGTT TTACGGACGG ACATGTGT

1701  CACACACACA GGCACCACAC CTTCCTCTTC TTGACATTTT TTCAGGGTCC ATTGACTAGA TGGAACCCTT AGACCACCCT CCCACCCCCA AGCATGGCTG
      GTGTGTGTGT CCGTGGTGTG GAAGGAGAAG AACTGTAAAG AAGTCCCAGG TAACTGATCT ACCTTGGGAA TCTGGTGGGA GGGTGGGGT TCGTACCGAC

1801  CACACACACA GGCACCACAC CTTCCTCTTC TTGACATTTC TTCAGGGTCC ATTGACTAGA TGGAACCCTT AGACCACCCT CCCCTCCCCA AGCATGGCTG
      GTGTGTGTGT CCGTGGTGTG GAAGGAGAAG AACTGTAAAG AAGTCCCAGG TAACTGATCT ACCTTGGGAA TCTGGTGGGA GGGGAGGGGT TCGTACCGAC

1801  CAAGTGTCAG ATACTTTGAA CCCCAGTGCC TTGTGGCACT TTTGAACAGA TTTGAACACAG GTTTTGCTGA TTTGAACAGA AACCTGTCT GTAGTAAAAC ATCCTAGAAT TAAATATGTA AAAAAAGTCC AGTATTTAC
      GTTCACAGTC TATGAAACTT GGGGTCACGG AACACCGTGA ACAAGAAATT CCAAACGACT CCAAACGACT GTAGTAAAAC ATCCTAGAAT TAAATATGTA AAAAAAGTCC AGTATTTAC

1901  TGGGATGAAC ATACTTTGAA CCCCAGTGCC TTGTGGCACT TGTTCTTTAA GGTGAGGGTC TTTGAACAGA TTTGAACACAG GTTTTGCTGA
      ACCCTACTTG TATGAAACTT GGGGTCACGG AACACCGTGA ACAAGAAATT CCACTCCCAG AACTTGTAAG AAACTTGTCT GTAGTAAAAC ATCCTAGAAT GTAGTAAAAC ATCCTAGAAT

2001  CTTCTGCTG ATACTTTGAA CAGGTCATGT TGTTCTTTAA GGTGAGGGTC TTATGACCGA CTGTTCTGAG AGGTATGTGC AGGTATGTGC AAGGCCTTAC CCACCAGTGG CTCTTTCACA
      GAAGACGAC GTCCAGTACA AACCGGTGA ACAAGAAATT CCACTCCCAG AATACTGGCT GACAAGACTC TGTCGGGACA CAGTCCGTTC TTCCGGAATG GGTGGTCACC GAGAAGTGT

2101  GGGTGTAGG TATTCCAAG ACGCCATAGG TGAATCATAG CTATCAGTTT GCTGTGGGCA AGGAACCTCT TTTTGGCCAC CTGGTAACAA
      CCCAACATCC ATAAAGGTTC TGCGGTATCC ACTTAGTAGT GATAGTCAAA CGACACCCGT TCCTTGGAGA AAAACCGGTG GACCATTGTT

2201  AATTTTATGT CTGTAAATTT TTTTCTTGCTA TTTAAAAAAAA AAAAAAAAA
      TTAAAATACA GACATTTAAA AAAGAACGAT AATTTTTTT TTTTTTTTT

FIG._1B
```

```
   1 CCCACGCGTC CGCTGAATGT ATGTTGGTTA GAAAGTAGCC TTTCTGCTTC CTGCCCATGG CCAGTTCTCC ACCCTCTCTT TGGTGTTCTT TGTGGGGAGG
     GGGTGCGCAG GCGACTTACA TACAACCAAT CTTTCATCGG AAAGACGAAG GACGGGTACC GGTCAAGAGG TGGGAGAGAA ACCACAAGAA ACACCCCTCC

101 GCACTGTGGT TTGTCGCAGC CCTGGACTTC GAGAGGCTCC CAGAACCCAG GATCACCAGC CTCCTGTCTG TTTGCTTCAC TCCTTCCCA GGGAGGACTT
     CGTGACACCA AACAGCGTCG GGACCTGAAG CTCTCCGAGG GTCTTGGGTC GAGGACAGAC AAGCGAAGTG AGGAAAGGGT CCCTCCTGAA

201 GGGACTGTCC TGTCTGACAG GACGGATCTG AGTTCCCGAA GCAAACCAGC TCACCACATA GATAGCTAGT TTTAAACAATG AGGGCACCTC
     CCCTGACAGG ACAGACTGTC CTGCCTAGAC TCAAGGGCTT CGTTTGGTCG AGTGGTGTAT CTATCGATCA AATTGTTAC AAAATTTTAT TCCCGTGGAG

301 TGTTTCAAAA GTGACATCTG CTGTGTTGTT TTCGAGGCCT GATACTCTTA CAAGGTTTGA AAAAAAAATGT GTGTATCCAT TCATGGGCTT GGTAGCCTTC
     ACAAAGTTTT CACTGTAGAC GACACAACAA AAGCTCCGGA CTATGAGAAT GTTCCAAACT TTTTTTACA CACATAGGTA AGTACCCGAA CCATCGGAAG

401 TGGTCACCTC AGTCCTGTGG CTCTTAACTT ATTGCCCAAC AATATTCATT TCCCCTCAGC TACAATGAAT AGTTCTCTCT CTCTCTCTTA GTTGTTAAAT CAGATTATGT
     ACCAGTGGAG TCAGGACACC GAGAATTGAA TAACGGGTTG TTATAAGTAA AGGGGAGTCG ATGTTACTTA ACGTTCGTTT TCTACAACTT TTTTTCGTGA

501 AATTTAGTTT AAAATGTCAC GATATTTTGT TTATTCTACA AAAACCATGA AGTTCTCTCT CTCTCTCTCT GTTGTTAAAT CAGATTATGT
     TTAAATCAAA TTTTACAGTG AAAAACAAA AATAAGATGT TTTGGTACT TCAAGAGAAT GAGAGAGAGA CAACAATTA GTCTAATACA

601 TCTTTTTTTG TTTTTGTTTT TAGTGATTCA CAGAGTGGAG TTTAACAAATC CTAGCTTTAA AAAAAACCTA TTTAATGTAA GATATTCTAC
     AGAAAAAAAC AAAAACAAAA ATCACTAAGT GTCTCACCTC AAATTGTTAG GATCGAAATT TTTTTTGGAT AAATTACATT CTATAAGATG

701 GCATCCTTCA GATATTTTGT ATATCCCCTA TGGCCTTTAG TCTGTACTTT TAATGTACAT ATTTCTGTCT GTAGATTTCA CTGGTTAAAA
     CGTAGGAAGT CTATAAAATC TATAGGGGAT ACCGGAAATC AGACATGAAA ATTACATGTA TAAAGACAGA CATCTAAAGT GACCAATTTT

801 GAGAGAGAACAT ATGCCAAGTG GAAGATAGAA TATAAAATAA AAATGTTACT TGTATATTGG TAAGAGGTTT CAGTTGTCCT TCAGCTAATT
     CTCTCTTGTA TACGGTTCAC CTTCTATCTT ATATTTTATT TTTACAATGA ACATATAAACC ATTCTCCAAA GTCAACAGGA AGTCGATTAA

901 CATGTAGAGA AATATTTTAG TTGAAGCCAC AAGAGACAGC TTCTCTGTCG TATGTGTTCA AATAACAGAA GAACAGACTT ATATGTTCCT TTTTTTTTT TTAAACCAAA
     GTACATCTCT TTATAAAATC AACTTCGGTG TTCTCTGTCG ATACAAAGT TTATTGTCTT CTTGTCTGAA TATACAAGGA AAAAAAAAAA AATTTGGTTT

1001 CCCAAACTGT TGGGAAACCT CAATAGAGCT CTATATGTAT TGGAACAAAA GTGGAATTCT CTTCTCCTAT ATATGTTCCT TCAAAAAGAG AGAGAGAATC
     GGGTTTGACA ACCCTTTGGA GTTATCTCGA GATATACATA ACCTTGTTTT CACCTTAAGA GAAGAGGATA TATACAAGGA AGTTTTTCTC TCTCTCTTAG

1101 AAGCAGATGG CTTAAAGCTG GTCACAGGAT TGCTTCACATT CTTTTGGCAT TATGCATGCG ACTTAATTGT TTGAGAGTGT TAACATCCCA
     TTCGTCTACC GAATTTCGAC CAGTGTCCTA ACGAGTGTAA GAAAACCGTA ATACGTACGC TGAATTAACA AACTCTCACA ATTGTAGGGT
```

FIG._2A

```
1201  GAGATGAATC AAAAAGGCTC ACCCTCTCAC CCAGGAGCAG CTTTTCAGCT TATATACACA TGCATGTACA TGTGTGTGAT ATGCATGTGT GCATGCATGT
      CTCTACTTAG TTTTTCCGAG TGGGAGAGTG GGTCCTCGTC GAAAAGTCGA ATATATGTGT ACGTACATGT ACACACACTA TACGTACACA CGTACGTACA

1301  TTGTATTTTT GTGCTTGCCA CTATAACTAT TGCACCTCTC TATTCGGTTT GACTGAAGAG GGGTCTTGTG GGACATCTCT GTGTCCCAGT CTTTATGGGA
      AACATAAAAA CACGAACGGT GATATTGATA ACGTGGAGAG ATAAGCCAAA CTGACTTCTC CCCAGAACAC CCTGTAGAGA CACAGGGTCA GAAATACCCT

1401  AGAAAGCAAG GGTCTGCAGA GAACAGGAAC TAAAGAATCC CTGTGTGATG TGCAATTAAT AGAAGGCCTC CTGCTTTCTG GAAATGTAGA CCAGAATCTG
      TCTTTCGTTC CCAGACGTCT CTTGTCCTTG ATTTCTTAGG GACACACTAC ACGTTAATTA TCTTCCGGAG GACGAAAGAC CTTTACATCT GGTCTTAGAC

1501  GCCAGGACTG TAGACTGATA CATTATCTGG TCCTTTGCCT TTTTCTTTTC CCTCCCCTGCC CCTCCCCCTC TTGCTTTATG GATAACCTTG TAACATATTG
      CGGTCCTGAC ATCTGACTAT GTAATAGACC AGGAAACGGA AAAAGAAAAG GGAGGGGACGG GGAGGGGGAG AACGAAATAC CTATTGGAAC ATTGTATAAC

1601  AAACCTTTAA AGGAAACCAA GAATGCATTA TTACACACAC ACACACACAC ACACACACAC ACACACACAC CAGTAGACCA ACATATAGAG
      TTTGGAAATT TCCTTTGGTT CTTACGTAAT AATGTGTGTG TGTGTGTGTG TGTGTGTGTG TGTGTGTGTG GTCATCTCGT TGTATATCTC

1701  TGTTTAAAAT AGCTTTTCTG GGCAAATTCA AACAACTTGT GTCAGCATCT CGCACATCTG TTTCCGTTTT TCTTCAGTTG TATATTGACC AGTATTCTTT
      ACAAATTTTA TCGAAAAGAC CCGTTTAAGT TTGTTGAACA CCGAGATCCT GCGTGTAGAC AAAGGCAAAA AGAAGTCAAC ATATAACTGG TCATAAGAAA

1801  ATTGCTAAAA CATATACTCG GGGTAGCAAT GTCAGCAAT  GTCAGCATCT TTTCCCTTCC CATCCTGGAG AGCATTCAAG ACCTTCCCAG TACAGGAACA TCAATGAAGC
      TAACGATTTT GTATATGAGC CCCATCGTTA CAGTCGTATA AAAGGGAAGG GTAGGACCTC TCGTAAGTTC TGGAAGGGTC ATGTCCTTGT AGTTACTTCG

1901  ATTTATATAC AGGCGGTGGC AAGCAGAACC ACATCCAAAA TGGTCAGTGT CGGGCTCTAG GGCAAGGCTA TCTTGTTCCA GTCCTCGTTTC TTTGTGCTCC
      TAAATATATG TCCGCCACCG TTCGTCTTGG TGTAGGTTTT ACCAGTCACA GCCCGAGATC CCGTTCCGAT CAGGACAAAG AACACGAGG

2001  TGACCTTTGG GGCTGCCACT TCCCAGGACG AGCCAATGGA ACCACTGCCT GCCCCACACTG TCCCCCCCCT AGGGGGGGAG AGCAGGATGA ATAGCCAGTT CCCATGTGTC
      ACTGGAAACC CCGACGGTGA AGGGTCCTGC TGGTGACGGA TGGTGACGAC CGGGGTGTGAC AGGGGGGCCCC CTAAAAGGGT TATCGGTCAA GGGTACACAG

2101  TTTTTCTGCA ACGTATTCA AGCCAATGGA ACCTTCAGAT AGGGCCCAAG AGCAGGATGA CACAACCTGT TATATTAACT TGATCACTAG
      AAAAAGACGT TGCCATAAGT TCGGTTACCT TGGAAGTCTA TCCCGGGTTC TCGTTCTACT GTGTTGGACA CCTGTTCTCG ATATAATTGA ACTAGTGATC

2201  TATGAGCTAA TATTAACATG ATCACCCATG AAAGGCGCCT GCAAGAGCTG TTTAGTCTGA AATATAGGTA GAGAGCGGGG ATGGCAAGGT TGCTTGTAAC
      ATACTCGATT ATAATATATG TAGTGGGTAC TTTCCGCGGA CGTTCTCGAC AAATCAGACT TTATATCCAT CTCTCGCCCC TACCGTTCCA ACGAACATTG

2301  TTCTGGTACA TGTTGAATGC ACACACGCAT GGAGGCAAGC TCTAAATCAC TGCACTGTTA CTGTAAAGCA TACTTAAAA ATATTTATTG TTTGAAAAAG
      AAGACCATGT ACAACTTACG TGTGTGCGTA CCTCCGTTCG AGATTAGTG ACGTGACAAT GACATTTCGT ATGAAATTTT TATAAATAAC AAAACTTTTC
```

*FIG._2B*

```
2401  CATTTTCTAG TCTTCCCTCT CTTGGTGGAG CTGTAAACAA GATGGCATGT TGTGAAGGTT CAAGATGATT TTTTTTTAAA TCGCAGAAAC ATTTAGACAC
      GTAAAAGATC AGAAGGGAGA GAACCACCTC GACATTTGTT CTACCGTACA ACACTTCCAA GTTCTACTAA AAAAAAATTT AGCGTCTTTG TAAATCTGTG

2501  CTAAGAACTA AAACTTATAA AAGGGATCTT TGAATTTGCC TGTTAACATG GATTAATGTT TACACTTACA GCTGATGATT GGACGGTGTT TTATGTTAGG
      GATTCTTGAT TTTGAATATT TTCCCTAGAA ACTTAAACGG ACAATTGTAC CTAATTACAA ATGTGAATGT CGACTACTAA CCTGCCACAA AATACAATCC

2601  GAAATGCCTT GTTAACGAAC TTCATGAAGC AGATGTAATT AAAGGTTGAT GTGAGCCAAT CTAGAAGGTT GAACAGTGTT TTCAAAGAAC GGAGAGACTT
      CTTTACGGAA CAATTGCTTG AAGTACTTCG TCTACATTAA TTTCCAACTA CACTCGGTTA GATCTTCCAA CTTGTCACAA AAGTTTCTTG CCTCTCTGAA

2701  ACATTTTAGA CCAATCTTTA TACATTTTGC TGAGCTAGAA AGGAGATAAA GATTATTTAT TTTTGTTCAT ATCTTGTACT TTTCTATTAA AATCATTTTA
      TGTAAAATCT GGTTAGAAAT ATGTAAAACG ACTCGATCTT TCCTCTATTT CTAATAAATA AAAACAAGTA TAGAACATGA AAAGATAATT TTAGTAAAAT

2801  TGAAAWMAA AAAAAAAAAA AA
      ACTTTWKKTT TTTTTTTTTT TT
```

FIG._2C

CCCACGCGTCCGCATATGTCTCCTTTGTGAGGATCAACAGCTCGCTGGCAGTGGCGGCTT
ACGAGGATGGGATCCTTAACATTTGGGACCTGAGAACCGGAAGGTTCCCTATCTTTCGTT
TTGAGCATGACGCAAGAATACAAGCCCTTGCGCTGAGCCAAGAAAAGCCCATTGTTGCCA
CGGCTTCTGCTTTTGACGTTGTGATGTTGTACCCCAACGAGGAGGGGCATTGGCATGTGG
CCTCGGAGTTTGAAGTTCAGAAGCTGGTTGACTACCTTGAAATAGTTCCGAATACTGGGA
GGTACCCTGTGGCAATAGCCACAGCCGGGGATCTGGTGTACCTGCTGAAGGCCGACGACT
CAGCCAGAACCCTTCATTATGTCAATGGCCAGCCTGCCACATGTCTGGATGTCTCAGCCA
GCCAGGTTGCCTTTGGAGTGAAGAGTCTAGGATGGGTGTATGAAGGAAACAAGATCCTGG
TGTACAGCCTGGAAGCAGAGCGCTGCCTCTCGAAGCTGGGCAATGCACTTGGAGACTTTA
CCTGTGTCAACATCCGGGATAGCCCTCCCAACCTCATGGTCAGCGGCAACATGGACAGGA
GAGTGAGGATTCATGACCTCCGCAGCGATAAGATCGCCCTGTCGCTGTCTGCCCATCAGC
TGGGGGTGTCCGCAATTCCAAATGGATAACTGGAAAGGTTGTCAGTGGAGGCCAGGAGGG
GTGGTGT

FIG._3

```
   1  CCCACGCGTC CGCATATGTC TCCTTTGTGA GGATCAACAG CTCGCTGGCA GTGGCGGCTT ACGAGGATGG GATCCTTAAC ATTTGGGACC TGAGAACCGG
      GGGTGCGCAG GCGTATACAG AGGAAACACT CCTAGTTGTC GAGCGACCGT CACCGCCGAA TGCTCCTACC CTAGGAATTG TAAACCCTGG ACTCTTGGCC

101  AAGGTTCCCT ATCTTTCGTT TTGAGCATGA CGCAAGAATA CGCTGAGCCA AGAAAAGCCC ATTGTTGCCA CGGCTTCTGC TTTTGACGTT
      TTCCAAGGGA TAGAAAGCAA AACTCGTACT GCGTTCTTAT GCGACTCGGT TCTTTTCGGG TAACAACGGT GCCGAAGACG AAAACTGCAA

201  GTGATGTTGT ACCCAACGA GGAGGGGCAT TGGCATGTGG CCTCGGAGTT TGAAGTTCAG AAGCTGGTTG ACTACCTTGA AATAGTTCCG AATACTGGGA
      CACTACAACA TGGGGTTGCT CCTCCCCGTA ACCGTACACC GGAGCCTCAA ACTTCAAGTC TTCGACCAAC TGATGGAACT TTATCAAGGC TTATGACCCT

301  GGTACCCTGT GGCAATAGCC ACAGCCGGGG ATCTGGTTGTA CCTGCTGAAG GCCGACGACT CAGCCAGAAC CCTTCATTAT GTCAATGGCC AGCCTGCCAC
      CCATGGGACA CCGTTATCGG TGTCGGCCCC TAGACCACAT GGACGACTTC CGGCTGCTGA GTCGGTCTTG GGAAGTAATA CAGTTACCGG TCGGACGGTG

401  ATGTCTGGAT GTCTCAGCCA GCCAGGTTGC CTTTGGAGTG AAGATCTAG TGAAGGAAAC AAGATCCTGG TGTACAGCCT GGAAGCAGAG
      TACAGACCTA CAGAGTCGGT CGGTCCAACG GAAACCTCAC CTACCCACAT TTCTAGAGAT CACTTCCTTTG TTCTAGGACC ACATGTCGGA CCTTCGTCTC

501  CGCTGCCTCT CGAAGCTGGG CAATGCACTT GGAGACTTTA CCTGTGTCAA CATCCGGGAT AGCCCTCCCA ACCTCATGT CAGCCGGCAAC ATGGACAGA
      GCGACGGAGA GCTTCGACCG GTTACGTGAA CCTCTGAAAT GGACACAGTT GTAGGCCCTA TCGGGAGGGT TGGAGTACCA GTCGCCGTTG TACCTGTCCT

601  CCATGACCTC CGCAGCGATA AGATCGCCCT GTCGCTGTCT GCCCATCAGC TGGGGGTGTC ATGGATGACT GGAAGGTTGT
      GGTACTGGAG GCGTCGCTAT TCTAGCGGGA CAGCGACAGA CGGGTAGTCG ACCCCACAG TACCTACTGA CCTTCCAACA

701  CAGTGGAGGC GAGGAGGGGC TGGTGTCTGT GTGGGATTAC CGCATGAACC AGAAGCTGTG GGAAGTGCAC TCCAGGCACC CTGTGGCCTA TCTCTCCTTC
      GTCACCTCCG CTCCTCCCCG ACCACAGACA CACCCTAATG GCGTACTTGG TCTTCGACAC CCTTCACGTG AGGTCCGTGG GACACCGGAT AGAGAGGAAG

801  AATAGCCACA GCCTCATCAC TGCCAACGTG CCCTACGAGA AGGTGCTGCG AAACTCCGAC CTGACAACT TTGCCTGTCA CAGGAGACAT CGTGGCCTGA
      TTATCGGTGT CGGAGTAGTG ACGGTTGCAT GGGATGCTCT TCCACGACGC TTTGAGGCTG GACTGTTGA AACGGACAGT GTCCTCTGTA GCACCGGACT

901  TCCATGCCTA TGAATTGCT GTGGACCAGC TGGCCTTTCA GAGCCCCCCTT CCTGTCTGCC GCTTACCCCG TGACATCATG GCTGATGACCT GCTATGACCT
      AGGTACGGAT ACTTAAACGA CACCTGGTCG ACCGGAAAGT CTCGGGGGAA GGACAGACGG CGAATGGGGC ACTGTAGTAC CGACCTATGT CGATACTGGA

1001  CGCACTGTCT TTCCCCCATG ACAGTATTTA GGGTGTCACC TCATGTAGAC GTGGAAAGGG CAGTTTTACA AATGTTAGAG TTGGAGAGAG GCTCTGCAGC
      GCGTGACAGA AAGGGGGTAC TGTCATAAAT CCCACAGTGG AGTACATCTG CACCTTTCCC GTCAAAATGT TTACAATCTC AACCTCTCTC CGAGACGTCG

1101  ACATGGTGGG AGTTTGGGGA CAGTGTCCTG TATGACTGTG GCCACACAGC CCTGTTGCCC TGTACAGAAC CAGACTCCAT TGCTGCCTTT CTCCCTCCTCC
      TGTACCACCC TCAAACCCCT GTCACAGGAC ATACTGACAC CGGTGTGTCG GGACAACGGG ACATGTCTTG GTCTGAGGTA ACGACGGAAA GAGGAGGAGG
```

FIG._4A

```
1201  TCCTCCTCCT CAGGCTTTGG TAGGACTGGC TGATGACTCA GAGTTAACCT TTCCAGGGGT GGCTCCTCCC CCTCAGCCTA TGGCAGCAGT GACACCCCCC
      AGGAGGAGGA GTCCGAAACC ATCCTGACCG ACTACTGAGT CTCAATTGGA AAGGTCCCCA CCGAGGAGG  GGAGTCGGAT ACCGTCGTCA CTGTGGGGGG

1301  CTCGTTCCAT AGGCCAGGGA CACAGGGCCT TCACTTGCAC TGTCTCCTGG CCAGAATCTC GAGGGTGCTG CCAAGCATAG ACACGCATAG GCAAGCGTCA
      GAGCAAGGTA TCCGGTCCCT GTGTCCCGGA AGTGAACGTG ACAGAGGACC GGTCTTAGAG CTCCCACCTT GGTCGTATC  TGTGCGTATC CGTTCGCAGT

1401  GCCTCCAAGC TGCCTCCCCA GCTGTCAGCC TCTCCAGCTG GCACCCTCCA GTGCAGCCCC TCCTCTGGGA GTGGGAGGT  TTCACACCGT TGATAATTAT
      CGGAGGTTCG ACGGAGGGGT CGACAGTCGG AGAGGTCGAC CGTGGGAGGT CACGTCGGGG AGGAGACCCT CACCCTCCAG AAGTGTGGCA ACTATTAATA

1501  AGGGCCACCT TACCTGTAGG AGCTGTTCTG TCCTGTACAT GTGCTATGAA GGAGACAGCC ATCCTTCCTG CAGAGGGAAA GGGTCATTGC ACAGGGATAG
      TCCCGGTGGA ATGGACATCC TCGACAAGAC AGGACATGTA CACGATACTT CCTCTGTCGG TAGGAAGGAC GTCTCCCTTT CCCAGTAACG TGTCCCTATC

1601  GGTCAGTCTC CAAGCCTAGC CGGTGGTGTC TCTTCCTGAC AAACGCAGCC GACCAGCAC  CACTCTGCCT ATGGACAAAT CCACACATAG
      CCAGTCAGAG GTTCGGATCG GCCACCACAG AGAAGGACTG TTTGCGTCGG CTGGTCGTG  GTGAGACGGA TACCTGTTTA GGTGTGTATC

1701  TGGCCAGGAG ACCCAGTCAG AGCTCTTCAG AATCCCCACA GGCTGGCAAA CTTCACATTG GGTCTGCCGA TGCACAGAGG TCAGGAGTC  AAGTTCCTCT
      ACCGGTCCTC TGGGTCAGTC TCGAGAAGTC TTAGGGGTGT CCGACCGTTT GAAGTGTAAC CACGACGGCT AGTCCTCTCC AGTCCTCTGT TTCAAGGAGA

1801  CCCAGGAAAT ACCAGCTCAA AAAACAAGTG GGCTGGCAAA CTTCCACATTG GGTCTGCCGA GAGCAAGAGA AAAGAGGGGG GTGGGGGAGC TCCATGGGGT
      GGGTCCCTTA TGGTCGAGTT TTTTGTTCAC CCGACCGTTT GAAGGTGTAAC CTCGTTCTCG TTTCTCCCCC CACCCCCTCG AGTACCCCA

1901  GGATCCCAGG CTGGCAGCAG GAAGGTGCTG GAGGGTGTGC GAGGGCCTGA AGTGCCCTCC CCGAGCCCTG GTGGTCTCCT CCTGTGTGCT GGGATGGAGT
      CCTAGGGTCC GACCGTCGTC CTTCCACACG CTCCCACACG CTCCCGGACT TCACGGGAGG GGCTCGGGAC CACCAGAGGA GGACACGA   CCCTACCTCA

2001  CTAGTGGGTT TGTGGCATGA TCTCAGATCT TGGCATTGAG ACCGTAACTC CCAGTCCTAA GCCCTCTCCC GCCCAGGGGA GCTCCACCTCC CTCTTGCTGG GCTGGCGCCC
      GATCACCCAA ACACCGTACT AGAGTCTAGA ACCGTAACTC GGTCAGGATT CGGAGAGGG  CGGGTCCCCT CGAGTGGAGG GAGAACGACC CGACCGCGGG

2101  CCTGCTGGCC TGGTCTTGCT GTGTCCTCAC TCGAGCATTC CAGTCCTAAG AGCTCGTAAG GCTGTCCACT CTGTCAGAGA AATTGGCTGT GCGGTCAGCT
      GGACGACCGG ACCAGAACGA CACAGGAGTG AGCTCGTAAG GGTCAGGATT TCGAGCATTC CGACAGGTGA CCCTCTGTAAA TTAACCGACA CGCCAGTCGA

2201  CCTTTCTGGG CTTCGCAGCC ATGAAAGAGC ACTGAAGAGC AGAGTAGTTT CAAGCATACA TGCCCTTCTA GCCCCCAATC CCTGCCCCT
      GGAAAGACCC GAAGCGTCGG TACTTTCTCG TGACTTCTCG TCTCATCAAA GTTCGTATGT ACGGGAAGAT CGGGGGTTAG GGACGGGGA

2301  ACCCCACACAG AGCATCTGTC CTCGCTGGCT CAGGTGGGGG CACCTGCTCC CACCCTGTGC GACAGGCTGG TGCCTCTGAA GCCAGAAGAC
      TGGGGGTGTC TCGTAGACAG GAGCGACCGA GTCCACCCCC GTGGACGAGG CTGTCCGACC GAGGGACACG CGGTCTTCTG

2401  ACCAGGACAC AGCCCTGGGA GCCAGGGGTG GCCAGGGCTT TGCAGCTTGC AGTCACACAT CTGCACACATC TCTACACATG AAGATGTGAC
      TGCCCTGTGT TCGGGACCCT CGGTCCCCAC CGGTCCCGAA ACGTCGAACG CAGTGTGTAG TAATAATTCC AAGATGTGAC

2501  AAAAAAAAAA AAAAAAAA  AAAAAA
      TTTTTTTTTT TTTTTTTT  TTTTTT
```

FIG._4B

```
  1 CTCCAACAGC GCAGGGCAGA GCGGCTGGCG CCGCCGGAGC CCGCCGGCCC GCCGAGCCAC GACCCTCCCT GTCCTACTGG CGTGCCGCCC GGAACCGCCA
    GAGGTTGTCG CGTCCCGTCT CGCCGACCGC GGCGGCCTCG GGCGGCCGGG CGGCGGCCTG CTGGGAGGGA CAGATGACCG GCACGCCGGG CCTTGCGGT

101 CTCTCCAGGG CCGGGACGC GCCCGCAGCT GTCGGTGACA GCTCCTCCCT ACCGCAACCC TCCGGGGCGG AGGGGCCGTC GGCCGGGCC CTGCTAGCCC
    GAGAGGTCCC GGCCCTGCG CGGGCGTCGA CAGCCACTGT CGAGGAGGGA TGGCGTTGGG AGGCCCCGCC TCCCCGCCAG CCGGCCCGGG GACGATCGGG

201 GCGACCGCAA GCCCGCGCTC GCGGATCGAT GCCCCCGCAG CCCGCGTTCC CGACCGCTGC GAGGGCCTC CGACGCCTGC GCGTCGGGAG
    CGCTGGCGTT CGGGCGCGAG CGCCTAGCTA CGGGGGCGCT GTTCCCCAGG GCTGGCGACG CTGGCGACG GCTCGCGACG GCCACCGCGG CGCAGCCCTC
                                                           M   P   P   Q   Q   G   D   P   A   F   P   D   R   C   E   A   P   P   V   P   P   R   R   E
  1

301 CGCGGTGGAC GCGGGGGACG CGGGCCCTGG GAGCCCGGGT GCCGAGGGCG TGCGGGGGT GCCGAGGGCG GCGGGCGTCAA GTGCGTGCTG GTCGGCGACG
    GCGCCACCTG CGCCCCCTGC GCCCGGGACCC CTCGGGCCCA ACGCCTCCCG CGGCTCCCCG ACGCCCCCCA CGGCCCCGC CAGCCACAGTT CAGCCGCTGC
 25  R   G   G   R   G   P   G   E   P   G   G   A   G   G   R   A   G   G   V   K   C   V   L   V   G   D   G

401 GCGCCGGTGG CAAGACGAGC CTGGTGGTGA GTTACACCAC CAACGGCTAC CCCACCGAGT ACATCCCTAC TGCCTTCGAC AACTTCTCCG CGGTGGTGTC
    CGCGGCCACC GTTCTGCTCG GACCACCACT CAATGTGGTG GTTGCCGATG GGGTGGCTCA TGTAGGGATG ACGGAAGCTG TTGAAGAGGC GCCACCACAG
 59  A   V   G   K   T   S   L   V   V   S   Y   T   T   N   G   Y   P   T   E   Y   I   P   T   A   F   D   N   F   S   A   V   V   S

501 TGTGGATGGG CGGCCCGTGA GACTCCAACT CTGTGACACT GCCGGACAGG ATGAATTTGA CAAGCTGAGG CCTCTCTGCT ACACCAACAC AGACATCTTC
    ACACCTACCC GCCGGGCACT CTGAGGTTGA GACACTGTGA CGGCCTGTCC TACTTAAACT GTTCGACTCC GGAGAGACGA TGTGGTTGTG TCTGTAGAAG
 92  V   D   G   R   P   V   R   L   Q   L   C   D   T   A   G   Q   D   E   F   D   K   L   R   P   L   C   Y   T   N   T   D   I   F

601 CTGCTCTGCT TCAGTGTCGT GAGCCCCTCA TCCTTCCAGA ACGTCAGTGA GAAATGGGTG CCGGAGATTC GATGCCACTG TCCCAAAGCC CCCATCATCC
    GACGAGACGA AGTCACAGCA CTCGGGGAGT AGGAAGGTCT TGCAGTCACT CTTTACCCAC GGCCTCTAAG CTACGTGAC AGGGTTTCGG GGGTAGTAGG
125  L   L   C   F   S   V   V   S   P   S   F   Q   N   V   S   E   K   W   V   P   E   I   R   C   H   C   P   K   A   P   I   I   L

701 TAGTTGGAAC GCAGTCGGAT CTCAGAGAAG ATGTCAAAGT CCTCATTGAG TTGGACAAAT GCAAAGAAAA CGTTTCTTTT GAAGAGGCGG CTAAGCTGTG
    ATCAACCTTG CGTCAGCCTA GAGTCTCTTC TACAGTTTCA GGAGTAACTC AACCTGTTTA CGTTTCTTTT GCAAAGAAAA CTTCTCCGCC GATTCGACAC
159  V   G   T   Q   S   D   L   R   E   D   V   K   V   L   I   E   L   D   K   C   K   E   K   P   V   P   E   E   A   A   K   L   C

801 CGCCGAGGAA ATCAAAGCCG CCTCCTACAT CGAGTGTTCA GCCTTGACTC AAAAAAACCT CAAAGAGGTC TTTGATGCAG CCATCGTCGC TGGCATTCAA
    GCGGCTCCTT TAGTTTCGGC GGAGGATGTA GCTCACAAGT CGGAACTGAG GTTTTTTGGA GTTTCTCCAG AAACTACGTC GGTAGCAGCG ACCGTAAGTT
192  A   E   E   I   K   A   A   S   Y   I   E   C   S   A   L   T   Q   K   N   L   K   E   V   F   D   A   A   I   V   A   G   I   Q
```

*FIG._5A*

```
 901 TACTCGGACA CTCAGCAACA GCCAAAGAAG TCTAAAAAGCA GGACTCCAGA TAAAATGAAA AACCTCTCCA AGTCCTGGTG GAAGAAGTAC TGCTGTTTCG
     ATGAGCCTGT GAGTCGTTGT CGGTTTCTTC AGATTTTCGT CCTGAGGTCT ATTTTACTTT TTGGAGAGGT TCAGGACCAC CTTCTTCATG ACGACAAAGC
 225 Y  S  D  T     Q  Q  Q     P  K  K     S  K  S  R     T  P  D     K  M  K     N  L  S  K     S  W  W     K  K  Y     C  C  F  V
 259 Q

1001 TATGATGCTG GCAAGACACC CAGAAAGGCT ATTTTCAGAT GAAATCGATA TTAGAAGCTA AACAACTCCT TTTACTGCGT AGAACCTATA
     ATACTACGAC CGTTCTGTGG GTCTTTCCGA TAAAAGTCTA CTTTAGCTAT AATCTTCGAT ATAAATCGACT TTGTTGAGGA AAATGACGCA TCTTGGATAT

1101 TCGAGAGTGT GTGTATATGT ATTATAGGAG GAGCTCTCAA TTTTATGTAT TCTTTCTGCC TTTAATTTTC TTGTTGTGTTT GAGCTTAGGG ATGAGATACT
     AGCTCTCACA CACATATACA TAATATCCTC CTCGAGAGTT AAAATACATA AGAAAGACGG AAATTAAAAG AACAAACAAA CTCGAATCCC TACTCTATGA

1201 TATGCAAGAT ATTTTGAAG TAAATTAAAC ATTTTTCACA TTAGAGTTTC TAGACCTCTG GTTAATTTAT ATCTAATATG AAGAAGACAC
     ATACGTTCTA TAAAAACTTC ATTAATTTG TAAAAGTGT AGAGACCTTT AATCTCAAG CAATTAAATA TAGATTATAC TTCTTCTGTG

1301 CTCTAATCTG GATGTTAAGA ATGAAGTTCT GCTACATTAT AATGTACAGA AGAGCAAAAG GGAGGAACAC TATGGTTAAC CCTCTCTTGA TTAAGGGCTA
     GAGATTAGAC CTACAATTCT TACTTCAAGA CGATGTAATA TTACATGTCT TCTCGTTTTC CCTCCTTGTG ATACCAATTG GGAGAGAACT AATTCCCGAT

1401 CTTAGTTCTG GTACACAGGT CAACCATGGT CAACAATAGTT CTTAGCTTTG AAACTCCATG CAAAACCATGC CTTTTTTTA AGGAGCAAAA
     GAATTACGTG TCACGTAATA GTTGGTACCA GTTATTATCA GAATCGAAAC TTTGAGGTAC GTTTGGTACG GAAAAAAAAT TCCTCGTTTT

1501 ATCTGAGAAA AAAAGTGAGA GACCCTCTGC TACAAAACTT CAAACCAGTC ACTTTGTCA ATTGCTAATA TATGATTTAT AAACAACCAA
     TAGACTCTTT TTTTCACTCT CTGGAGACGG ATGTTTTGAA GTTTGGTCAG TGAAAACAGT TAACGATTAT ATACTAAATT TTTGTTGGTT

1601 CAGAAAACAT CCCACAGACT GTATGGCACT CTGTAGTCAA AAAGGAAAC TTTCTTATTG GGACTTTTCT CCTGAAAAGA AGAATCAGG ACACATATGA
     GTCTTTTGTA GGGTGTCTGA CATACCGTGA GACATCAGT TTTTCCTTTG AAAGAATAAC CCTGAAAAGA GGACTTTTCT TCAACACAAC TGTGTATACT

1701 ACACAGACAA AGTGCTATGC GGAGGAAAGC AAGTGTTGGT CAGTAGTTTC AATGTTTTAGG TGTGGAGATC GAGTGGTTCC AGAAAGTGAC ATTTGCTTTC
     TGTGTCTGTT TCACGATACG CCTCCTTTCG TTCACAACCA GTCATCAAAG TACAAAATCC CTCACCAAGG CTCACCAAGG TCTTTCACTG TAAACGAAAG

1801 GGTACTGTAA TACATGCACC AAACTGCCTC AATCCTAGGT AACGAGGGCA ACAGGGAGCA CCTGTCTGGA TTGTTTTTAA ACCTCCATAC TCAAGCTGTC
     CCATGACATT ATGTACGTGG TTTGACGGAG TTAGGATCCA TTGCCTCCGT TGTCCCTCGT GGACAGACCT AACAAAAATT TGGAGGTATG AGTTCGACAG

1901 TCTTCGGCAG GGAGGTGAAT ACTCTTGAAA GGCCAACAGC AAGTGTTTGT GGGACACAAC CCCTGTGTTG TTCACAAACA TTTTCTTAAG TCGACCAAGA TGTACTTCTC
     AGAAGCCGTC CCTCCACTTA TGAGAACTTT CCGGTTGTCG TTCACAAACA CCCTGTGTTG AAAGAATTC AGCTGGTTCT ACATGAAGAG

2001 TGTGTGCACA CCCATGCACA CTCATGCACA CAGATACACA GGTCTGTATG CTGTTGATTC AGACTTTCAC ACCATTAATG GGGAAAAGCG
     ACACGTGTGT GGGTACGTGT GAGTACGTGT GTCTATGTAT CCAGACATAC CGACAACTAAG TCTGAAAGTG TGGTAATTAC CCCTTTTCGC
```

FIG._5B

```
2101  TGGCCACAAA AACAGATGCT AGGAAGCTTG GCTTCCTCTT CTTGTTGACC CTTTTTTGAA CCAACATCTT TTTTATTATA TTCAGAGTAT GTTTTTAAGT
      ACCGGTGTTT TTGTCTACGA TCCTTCGAAC CGAAGGAGAA GAACAACTGG GAACAAACTT GGTTGTAGAA AAATAATAT AAGTCTCATA CAAAAATTCA

2201  GTATCTTAAT ATATACATTT TTTAGGACAT CTTAAATCTA AACAAAAAAT AAAATGAACA TCTCTTGAAA CCTGTTAAAA AGCCACAGA
      CATAGAATTA TATATGTAAA AAATCCTGTA GAATTTAGAT TTGTTTTTTA TTTTACTTGT AGAGAACTTT GGACAATTTT GTTGGTCAAT TTCGGTGTCT

2301  TGGCTTTCAG GGCAGTAGCA GCAGAGGCCA GTGGACTCTG AGGACTCCTG AGGGGCGGGG CGTGTAGCCA GCCAGGTGCA TGCCGGGACC ATGGCCCCCA
      ACCGAAAGTC CCGTCATCGT CGTCTCCGGT CACCTGAGAC TCCTGAGGAC TCCCCGCCCC GCACATCGGT CGGTCCACGT ACGGCCCTGG TACCGGGGGT

2401  TACTTGGCTG CTTCCTGTGA CAGTGAAATA GGTGGCAGCT GTTAGGGCTG AATCTTCTGG AGAAAAAGGT GCCATCTCAG GAGAATAGCT
      ATGAACCGAC GAAGGACACT GTCACTTTAT CCACCGTCGA CAATCCCGAC TTAGAAGACC TCTTTTTCCA CGGTAGAGTC CTCTTATCGA

2501  TTTTACTCTGG TAGGAATGCT TCCGAGACAC CACAAGGCAG CCTGAACACT CAGTTGCAGG GTCGGGCTTG CGGTGGGTGA CCCAGAGCCA CCAAAGTCAC
      AAATGAGACC ATCCTTACGA AGGCTCTGTG GTGTTCCGTC GGACTGTGA GTCAACGTCC CAGCCCGAAC GCCACCCACT GGGTCTCCGGT GGTTTCAGTG

2601  ATCCACAACT AATGAGGGAA ATCTGTAAAG CCAGTTAGAT AGAAGAGTTT TATTTTCTG TGGGTTTTGT GTTGTCTTTT TTATGTCTTTT AAGAAATCCA
      TAGGTGTTGA TTACTCCCTT TAGACATTTC GGTCAATCTA TCTTCTCAAA ATAAAAAGAC ACCCAAACA CAACAGAAAA AATACAATT TTCTTAGGT

2701  GTTTGTGTTT TTCTATAGAA AAAGTAAAAG ATCAGGTTAT ACTTAGGTT AGGGGTTCTA TTTATTCCTG TTAGTAAATA AAATTAACAA ATTTCTTTGT
      CAAACACAAA AAGATATCTT TTTCATTTTC TAGTCCAATA TGAAATCCAA TCCCCAAGAT AAATAAGGAC AATCATTAT TTTAATTGTT TAAAGAAACA

2801  TTAACAAAAG ATTAATCTTT AAACCACTAA AATACATAGA ATTCAACACA CTGATTGATT AACTTAACT GTCTCATCTT AGTTTCCTGA AGCATTAGT
      AATTGTTTTC TAATTAGAAA TTTGGTGATT TTATGTATCT TAAGTTGTGT GACTAACTAA TTGAATTGA AACCTTAACT ACAGCCAGTA TCAAAGGACT TCGTAAATCA

2901  TACAACCTGA AGGAATAAAA TGATTTGTGG AAATGCTTAA AATAGACCTA ACTGAATACA AAGAAGTTTT ATGCCGTGTGA CAGTGTATGG GGCTGCAGTT
      ATGTGGACT TCCTTATTTT ACTAAACACC TTTACGAATT TTATCTGGAT TGACTTATGT TCTTCAAAA TACGCACACT GTCACATACC CCGACGTCAA

3001  CTAGGCTTCC CAGGTGGGCT CTGCCTGTCT GGTGCCTGGA GGTGTGGGAG GGAAGATGAG TTATTAACT AAGAAGTTT TGAAACACT ATTTTTATAT
      GATCCGAAGG GTCCACCCGA GACGGACAGA CCACGGACCT CCACACCCTC CCTTCTACTC AATAAATTGA ACTTTGTGA TAAAAATATA

3101  TAAAGTAAAT GGCATGGAGT ATAGTGCAAA TTCATTTTTA AGATAGAACA CAAAACTTGA AAGAAGTTT TCTTCAAAA CAGTGTATGG GGCTGCAGTT
      ATTTCATTTA CCGTACCTCA TATCGTTT AAGTAAAAAT TCTATCTTGT GTTTTGAACT TCTTCAAAA TACGCACACT GTCACATACC CCGACGTCAA

3201  GGTCTCCCTG GAGGGGACTT CCCCCTGAA TGCCTTTAGG CCATGGGTGG AAAGTGCTCA GTGAAGTACA CCTGTGTGGC CCAGTTCTGA AAGCTTTATA
      CCAGAGGGAC CTCCCCTGAA ACGGAAATCC GGTACCACC TTTCACGAGT CACTTCATGT GGACACACCG GGTCAAGACT TTCGAAATAT
```

FIG._5C

```
3301  CAGTTGAATT TTAAGTGGGG TTGATAACAC CTTGGACTGT TAGTGTTAAA AATCTAGTGG GTTGACCTTT AAATGCACAG TTTTTAAAAT ATATTGCTGC
      GTCAACTTAA AATTCACCCC AACTATTGTG GAACCTGACA ATCACAATTT TTAGATCACC CAACTGGAAA TTTACGTGTC AAAAATTTTA TATAACGACG

3401  ATTTATAGA ATAGTAAAGG TACGATTATA CTTGAGATTT TCCTCCATTT TTATTCTTTC GTGAACATAG AGTTTGGGGC CGAAAATGTT TTTAAAGTAT
      TAAATATCT TATCATTTCC ATGCTAATAT GAACTCTAAA AGGAGGTAAA AATAAAGAAG CACTTGTATC TCAAACCCCG GCTTTTACAA AAATTTCATA

3501  GTGTTTGAGT TAAATATAAA GTTGGTTCAC TTCAAAGCTA AAAAATTGTT AAACTTGCAG CTTGGTATTG CAGAGAAGAT TTTATAAGAA TTTTGCTTTA
      CACAAACTCA ATTTATATTT CAACCAAGTG AAGTTTCGAT TTTTAACAA TTTGAACGTC GAACCATAAC GTCTCTTCTA AAATATTCTT AAAACGAAAT

3601  GAGAATGCCA CTTTGGCTGA ACTACAAGTG TAGGCCACCA TTATAATTTA TAAATCCAGC ATACTTCAAA ACTGTTTGTT ATCTCTTGTT ACCATGTATG
      CTCTTACGGT GAAACCGACT TGATGTTCAC ATCCGGTGGT AATATTAAAT ATTAGGTCG TATGAAGTTT TGACAAACAA TAGAGAACAA TGGTACATAC

3701  TATAAATGGA CCTTTATATA CCTTGTTCTC TGCTTGACAG AACTCAAGAGA AACTACCCAG GTATTACACA AGCCAAAATG GGAGCAAGGC CTTCTCTCCA
      ATATTACCT GGAAATATT GGAACAAGAG ACGAACTGTC TGAGTTCTCT TGATGGGTC CATAATGTGT TCGGTTTTAC CCTCGTTCCG GAAGAGAGGT

3801  GACTATCGTA ACCTGGTTGCC TTACCAAGTT GTGCTTTTCT GTTTTCAAGT GTAAATGATG TTGAGCAGAA TGTTGTACTT GAAAATGCTA TAAGTGAGAT
      CTGATAGCAT TGGACCACGG AATGGTTCAA CACGAAAAGA CAAAGTTCA CATTTACTAC AACTCGTCTT ACAACATGAA CTTTTACGAT ATTCACTCTA

3901  GGTATGAAAT AAATTCTGAC TTATGAACTG TTTAAGACTG AAATTTATAT AAAAAAAAAA AAAAAAAAAA
      CCATACTTTA TTTAAGACTG AATACTTATA TTTTTTTTTT TTTTTTTTTT
```

*FIG._5D*

```
mouse.cl.65    1  M A P Q Q G R P A L P A R C E P P A A P P V P P R R E R G G R G A R G P G V S G G R G R A G G A E G
human.cl.65    1  M P P Q Q G D P A F P D R C E - - - A P P V P P R R E R G G R G R G P G E P G G R G R A G G A E G mouse.cl.65   51  R G V K C V L V G D G A V G K T S L V V S Y T T N G Y P T E Y I P T A F D N F S A V V S V D G R P V
human.cl.65   48  R G V K C V L V G D G A V G K T S L V V S Y T T N G Y P T E Y I P T A F D N F S A V V S V D G R P V mouse.cl.65  101  R L Q L C D T A G Q D E F D K L R P L C Y T N T D I F L L C F S V V S P T S F Q N V G E K W V P E I
human.cl.65   98  R L Q L C D T A G Q D E F D K L R P L C Y T N T D I F L L C F S V V S P S S F Q N V S E K W V P E I mouse.cl.65  151  R R H C P K A P I I L V G T Q S D L R E D V K V L I E L D K C K E K P V P E E A A K L C A E E V K A
human.cl.65  148  R C H C P K A P I I L V G T Q S D L R E D V K V L I E L D K C K E K P V P E E A A K L C A E E I K A mouse.cl.65  201  V S Y I E C S A L T Q K N L K E V F D A A I V A G I Q H S D S Q L Q P K K S K S R T P D K V R D L S
human.cl.65  198  A S Y I E C S A L T Q K N L K E V F D A A I V A G I Q Y S D T Q Q P K K S K S R T P D K M K N L S mouse.cl.65  251  K S W W R K Y C C L A
human.cl.65  248  K S W W K K Y C C F V
```

FIG._6

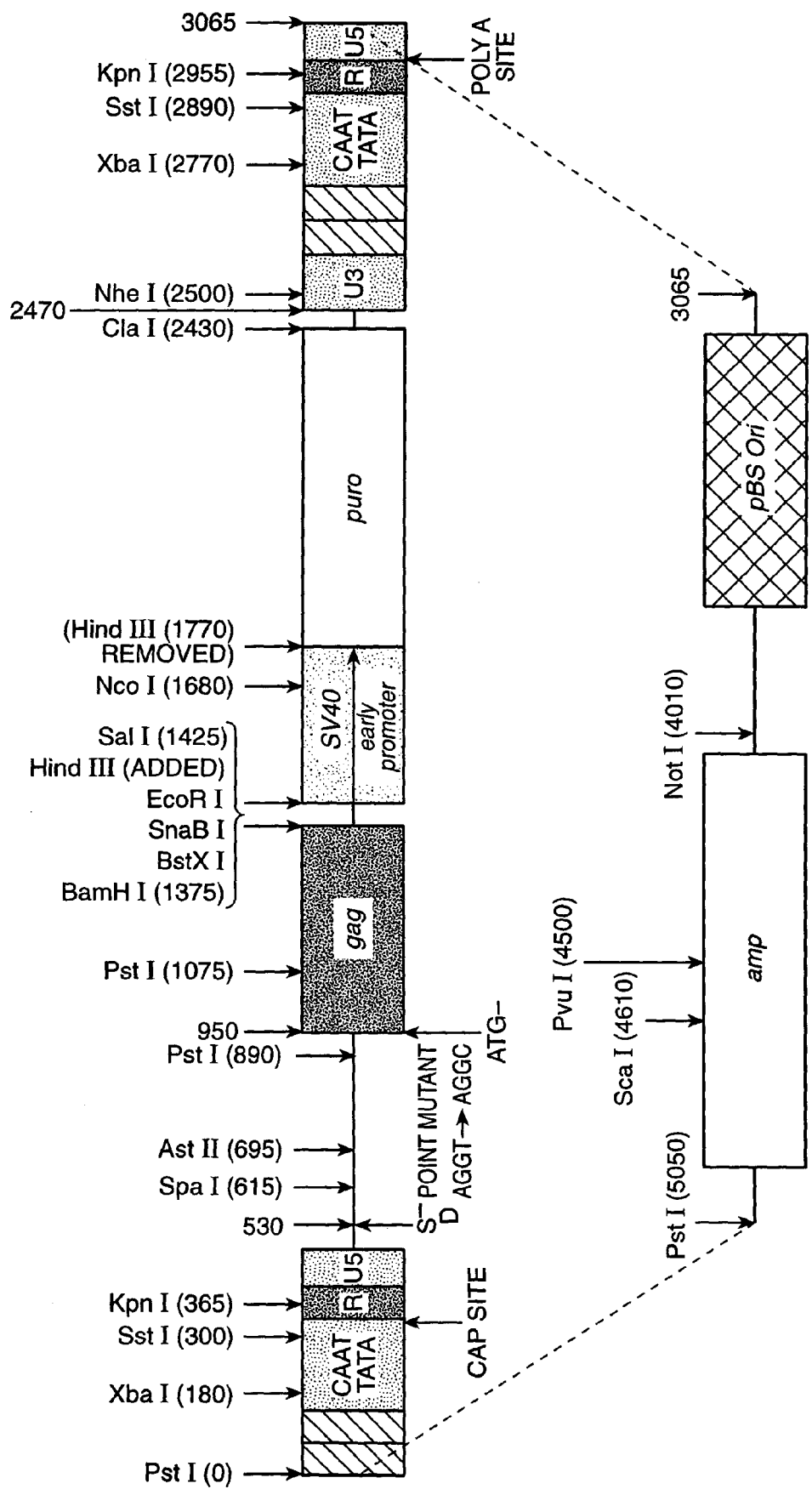
FIG._7

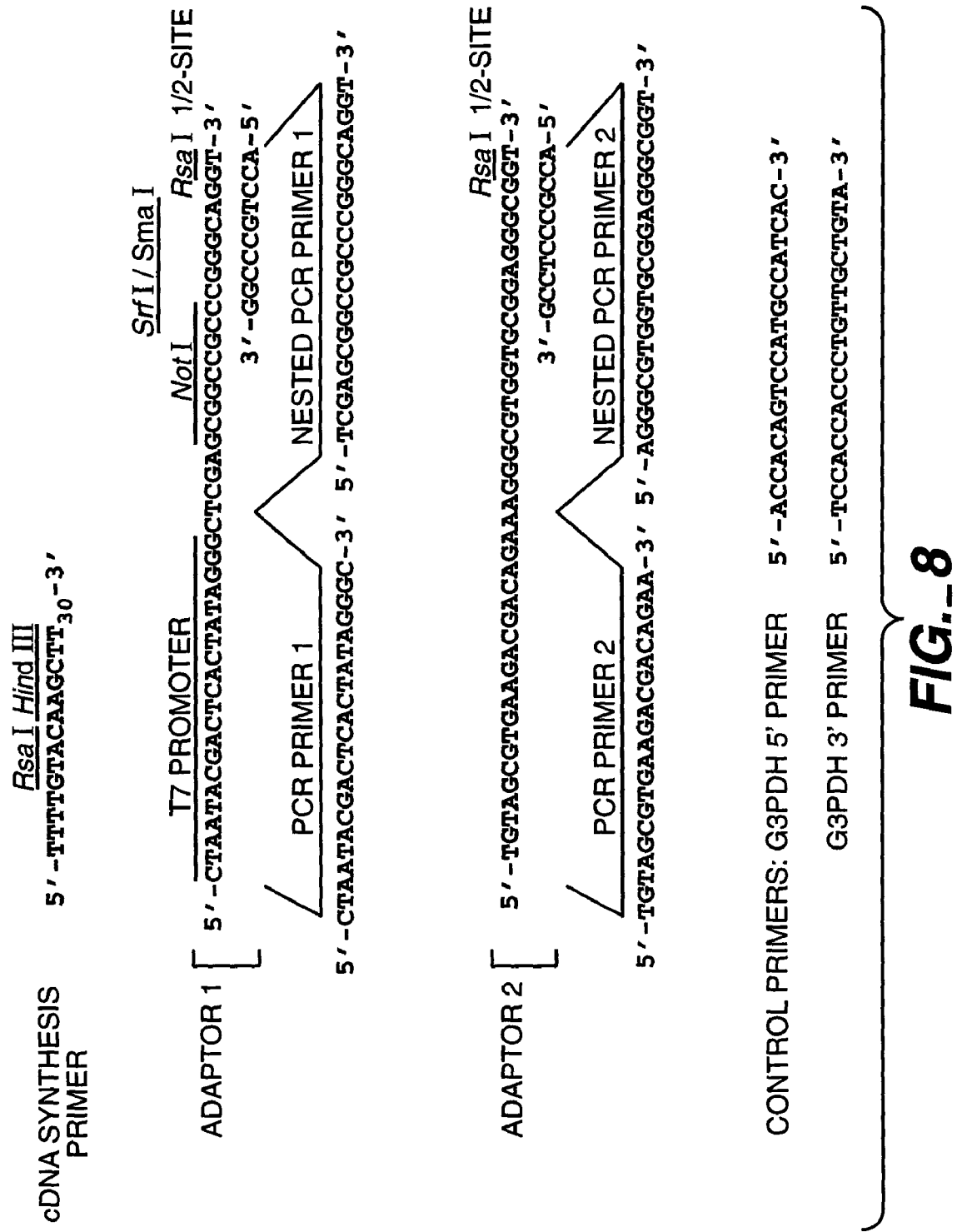
FIG._8

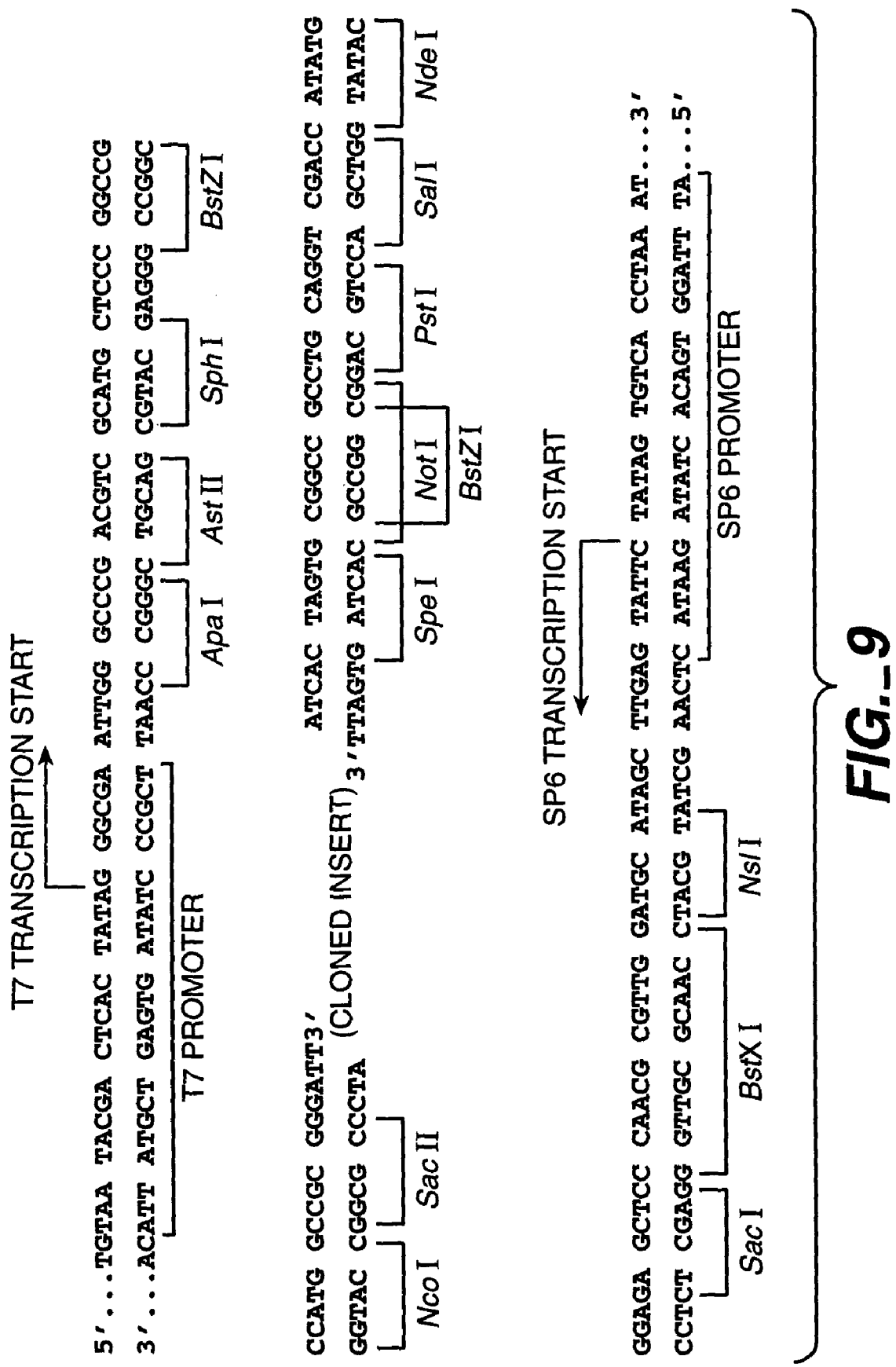
FIG._9

```
5'-CCCACGCGTCCGCGCGGTGGGCAAGACCAGCCTGGTGGTCAGCTACACCACTAACG
GCTACCCCACCGAGTACATCCCTACGGCCTTCGACAACTTCTCGGC
CGTGGTGTCTGTAGATGGGCGGCCTGTGAGACTCCAGCTCTGTGACACTGCAGGACAGG
ATGAGTTTGACAAGCTGAGGCCCCTCTGCTACACCAACACAGACATCTTCCTGCTGTGCTTCA
GCGTGGTGAGCCCCACATCCTTCCAGAACGTGGGCGAGAAGTGGGTTCCAGAGATTCGAC
GTCACTGCCCAAAGGCCCCATCATCCTGGTCGGGACACAGTCGGACCTCAGGGAGGACGTCA
AAGTGCTCATAGAACTGGCTTCTGCAGGGCATCTGTGTCCTGCTGTTAAAAGCAGGAGGAG
GTGCTTGTCTGGGAGCTTTAAGTGTGCTGGGCTCATATCGTCCCGTTTGCAAGGAATTG
GGCCACCTTGAGAGGCCATAGTTGATGGCTATGGGACACACACACACTTTTTCCTTAAGTCC
ACCAAAATGCCTGCCTGTACACACACACACACACACACACACACACACACACACACACACACT
GGCTGGTTTGCTGATGGAACCCTTAGACCACCCTCCCACCCCCACCCCTCCCCAAGCATGGC
TGCAAGTGTCAGGGCACCACACCTTCCTCTTCTTGACATTTCTTTGAACAGACATCATTT
TGTAGGATCTTAATTTATACATTTTTTCAGGTCATAAAATGTGGGATGAACATACT
TTGAACCCCAGTGCCTTCAGGGTCCATTGACTAGGGAGGCACTGTCTTAGGGGACAGGTAT
GTGCAAGGCCTTACCCACCAGTGGCTTCTCGCTGCAGGTCATGTTTGTGGCACTTGTTCTT
TAAGGTGAGGGTCTTATGACCGACTGTTCTGAGACAGCCCTGTGTCAGGCAAGCTCTTT
CACAGGGTTGTAGGTATTTCCAAGACGCCATAGGAACCAGACAGTGAATCATAGCTATCAGT
TTGCTGTGGGCAAGGAACCTCTTTTGGCCACCTGGTAACAAAATTTATGTCT
GTAAATTTTTTCTTGCTATTTAAAAAAAAAAATCAATCTTACGTTTTTCTGTAGGAAA
AAAAAAAACAAGTAAAAGAACAGGCCATATTTCAGGTCAAAGGCTTCTTCCTGCTG
GTAAATGGGACTGAAGACTTTCTTACATCATTATTAAAAGGCTAATTGCTGAACCA
CTAGAGTATATGAACTGTTTGTGAATGATATTAGCCATAGTCTCCTGAGGTGTTT
CCTTGTGGCCTGAGTGGTAACATTGTTTTGCTTATGGAGATGCTGTAACTGACCTAGTGACTCAGC
TTATCCTATTGTGCATGGCTGTCTGGAAAGCCAGCGTACAAGTGGGGCTTTGCCTGCCCTGTGTA
CAGAGGGTGGGTGGGAAGAGTGAATTATTTAATTTTAAATGTTATAATAAAGCCAATGTAGTTGA
GACCAAGGAAATGAGCATTGAGAACACAAACTTGAAGTCTGGTGCCAGGGTTGTTGGACCTC
ACACCCTGTCTCTGAGCCACCCGGAAGTGACATAAAGGACGCTGTGTGATCAAGT
TCTGGACACTTTTCTGGGATGCGTACCACTGGACTATTTATGTCACAAATCTAGTGGGTT
GACGCTGCCCTGCAAGTTTTCAATGTCCCTGCATCCTATGAAGTCATAATGTCTGAC
TGTACTGGAGGTTTTCCTGCATTTTTACTTTTCGAAAATAGAGGTTTGGGCTGAGAAT
TCTAAACGCATGTGCCTGGGTGGACGTCAAGTCAGGGTTCTCATCAAAGCTGAGAA
GTGGCTGGAATGTTCAGCTTGGTGTCTGGGGAGGATCCTGTGAGCTATGTAGA
GAGGTGGCTCTTCAGCCTGACTCAGTGTGGGCTGAACGAAGTACCTGCAGAACACACGGT
AGCAGGCTCCAAAATCGTCACCTCAAGCATGCGTGCAAGCAAACTTCCGAGAACTCC
GTTTTCTGCTCGGCAGACGTGTGAGCAGCTACCCAGAAGTCTCAAGCCAAAAGGGGAGCCTCG
CTCGCTGGCTCCTCTGCAGGTGCCTTATCGACCTGTGCTCTTCTCTTTTCCCGTGTCAAA
GATGTTGGACAGGATCTTGTACTTGAAACATACTACAAATGAGTTACTATGAAATAAATTC
TGACCTGTGGACCGAAAAAAAAAAAAAAAAAA
```

FIG._10

```
5'-CCCACGCGTCCGCACGTGACCAGTTATATTGCTATGAAAATGGTGGAGATGCCTCGTA
GAAGGCGAGTGCTGGGTGCACATGTGACATTTTCTTCAGGGAGCGACTCATGGTGAGACCA
GAGAGGGCTCTTAGCTTGCAGGACTGGCTTCTGCAGGGCATCTGTGTCCTGCTGTTAAAAG
CAGGAGGAGGTGCTTGTCTGGGAGCTTTAAGTGTGCTGGGCTCATATCGTCCCGTTTGCA
AGGAATTGGGCCACCTTGAGAGGCCATAGTTGATGGCTATGGGACACACACACTTTTT
CCTTAAGTCCACCAAAATGCCTGCCTGTACACACACACACACACACACACACACACAC
ACACACACTGGCTGGTTTGCTGATGGAACCCTTAGACCACCCTCCCACCCCCACCCCT
CCCCAAGCATGGCTGCAAGTGTCAGGGCACCACACCTTCCTCTTCTTGACATTTCTTTGA
ACAGACATCATTTTGTAGGATCTTAATTTATACATTTTTTTCAGGTCATAAAATGTGGGA
TGAACATACTTTGAACCCCAGTGCCTTCAGGGTCCATTGACTAGGGAGGCACTGTCTTAG
GGGACAGGTATGTGCAAGGCCTTACCCACCAGTGGCTTCTCGCTGCAGGTCATGTTTGTG
GCACTTGTTCTTTAAGGTGAGGGTCTTATGACCGACTGTTCTGAGACAGCCCTGTGTCAG
GCAAGCTCTTTCACAGGGTTGTAGGTATTTCCAAGACGCCATAGGAACCAGACAGTGAAT
CATAGCTATCAGTTTGCTGTGGGCAAGGAACCTCTTTTTGGCCACCTGGTAACAAAATTT
TATGTCTGTAAATTTTTCTTGCTATTTAAAAAAAAAAATCAATCTTACGTTTTTCTGT
AGGAAAAAAAAAAACAAGTAAAAGAACAGGCCATATTTCAGGTCAAAGGCTTCTTCCTGC
TGGTAAATGGGACTGAAGACTTTCTTACATCATTATTAAAAGGCTAATTGCTGAACCACT
AGAGTATATGAACTGTTTGTGAATGATATTAGCCATAGTCTCCTGAGGTGTTTCCTTGTG
GCCTGAGTGGTAACATTGTTTGCTTATGGAGATGCTGTAACTGACCTAGTGACTCAGCT
TATCCTATTGTGCATGGCTGTCTGGAAAGCCAGCGTACAAGTGGGCTTTGCCTGCCCTG
TGTACAGAGGGTGGGTGGGAAGAGTGAATTATTTAATTTTAAATGTTATAATAAAGCCA
ATGTAGTTGAGACCAAGGAAATGAGCATTGAGAACACAAACTTGAAGTCTGGTGCCAGGG
TTGTTGGACCTCACACCCTGTCTCTGAGCCACCCGGAAGTGACATAAAGGACGCTGTGTG
ATCAAGTTCTGGACACTTTTCTGGGATGCGTACCACTGGACTATTTATGTCACAAATCTA
GTGGGTTGACGCTGCCCTGCAAGTTTTCAATGTCCCTGCATCCTATGAAGTCATAATGTC
TGACTGTACTGGAGGTTTTCCTGCATTTTTTACTTTTCGAAAATAGAGGTTTGGGCTGAG
AATTCTAAACGCATGTGCCTGGGTGGGACGTCAAGTCAGGGTTCTCATCAAAGCTGAGAA
GTGGCTGGAATGTTCAGCTTGGTGTCTGGGGAGGATCCTGTGAGCTATGTAGAGAGGTGG
CTCTTCAGCCTGACTCAGTGTGGGCTGAACGAAGTACCTGCAGAACACACGGTAGCAGGC
TCCAAAATCGTCACCTCAAGCATGCGTGCAAGCAAACTTCCGAGAACTCCGTTTTCTGCT
CGGCAGACGTGTGAGCAGCTACCCAGAAGTCTCAAGCCAAAAGGGGAGCCTCGCTCGCTG
GCTCCTCTGCAGGTGCCTTATCGACCTGTGCTCTTCTCTTTCCCGTGTCAAAGATGTTG
GACAGGATCTTGTACTTGAAACATACTACAAATGAGTTACTATGAAATAAATTCTGACCT
GTGGACCGAAAAAAAAAAAAAAAA
```

FIG._11

5'-CCCACGCGTCCGCGCCGAGGGACGCGGCGTCAAGTGCGTGCTGGTCGGCGACGGCGCGGT
GGGCAAGACCAGCCTGGTGGTCAGCTACACCACTAACGGCTACCCCACCGAGTACATCCC
TACGGCCTTCGACAACTTCTCGGCCGTGGTGTCTGTAGATGGGCGGCCTGTGAGACTCCA
GCTCTGTGACACTGCAGGACAGGATGAGTTTGACAAGCTGAGGCCCCTCTGCTACACCAA
CACAGACATCTTCCTGCTGTGCTTCAGCGTGGTGAGCCCCACATCCTTCCAGAACGTGGG
CGAGAAGTGGGTTCCAGAGATTCGACGTCACTGCCCAAAGGCCCCCATCATCCTGGTCGG
GACACAGTCGGACCTCAGGGAGGACGTCAAAGTGCTCATAGAACTGGACAAGTGCAAAGA
GAAGCCGGTGCCTGAAGAGGCGGCGAAGCTGTGCGCGGAGGAAGTCAAAGCTGTCTCCTA
CATCGAGTGCTCAGCGTTGACTCAGAAAAACCTCAAAGAGGTTTTCGACGCCGCCATTGT
TGCTGGTATCCAGCACTCAGACTCCCAGCTACAGCCAAAGAAGTCTAAAAGCAGGACCCC
GGATAAGGTGCGGGACCTGTCCAAGTCTTGGTGGAGGAAGTATTGCTGCCTGGCCTGACT
CTCGCAAATAGCAGGTGTTTAAGCTGCAACAGCTCTTTATGGACGAGGCTGTCATAGGAT
GAGCCCCAAAGCACCCTCTTCTGCCCTTAACTTCCTGTGTGCGGGAGCTTAGGGCTGAGA
TTCATATGCAAAATACGTTTTTTTAAAAATTGAAAGTTACATTTTTTTTCTGTTAAGTCT
GGAAGCTTTGAGCTGTTAGACCTCCGGATTAATTTATATTCCATATGAAAAGGGCTCTTC
AAAAGCGGGGGTGTCAGCATGAAGTTCTGCTGGTGTTTGTACAGGACAAAGGAGAATGAA
TGGGGAACCTTCCTCCTGAATTAAGGGGCTAACTGAAGGGCTCAATTGCAAGGGCA

FIG._12

5'-CGCGGTGGGCAAGACCAGCCTGGTGGTCAGCTACACCACTAACGGCTACCCCACCGAGTA
CATCCCTACGGCCTTCGACAACTTCTCGGCCGTGGTGTCTGTAGATGGGCGGCCTGTGAG
ACTCCAGCTCTGTGACACTGCAGGACAGGATGAGTTTGACAAGCTGAGGCCCCTCTGCTA
CACCAACACAGACATCTTCCTGCTGTGCTTCAGCGTGGTGAGCCCCACATCCTTCCAGAA
CGTGGGCGAGAAGTGGGTTCCAGAGATTCGACGTCACTGCCCAAAGGCCCCCATCATCCT
GGTCGGGACACAGTCGGACCTCAGGGAGGACGTCAAAGTGCTCATAGAACTGGCTTCTGC
AGGGCATCTGTGTCCTGCTGTTAAAAGCAGGAGGAGGTGCTTGTCTGGGAGCTTTAAGTG
TGCTGGGCTCATATCGTCCCGTTTGCAAGGAATTGGGCCACCTTGAGAGGCCATAGTTGA
TGGCTATGGGACACACACACTTTTTCCTTAAGTCCACCAAAATGCCTGCCTGTACACA
CACACACACACACACACACACACACACACACTGGCTGGTTTGCTGATGGAACCC
TTAGACCACCCTCCCACCCCCACCCCTCCCCAAGCATGGCTGCAAGTGTCAGGGCACCAC
ACCTTCCTCTTCTTGACATTTCTTTGAACAGACATCATTTGTAGGATCTTAATTTATAC
ATTTTTTTCAGGTCATAAAATGTGGGATGAACATACTTTGAACCCCAGTGCCTTCAGGGT
CCATTGACTAGGGAGGCACTGTCTTAGGGGACAGGTATGTGCAAGGCCTTACCCACCAGT
GGCTTCT

FIG._14

```
5'-CCCACGCGTCCGGCGCGAGCTTAGCAGATCTCCACTTACCGAACATCTAGAGAGTCGCGC
CGCGCGCCGACGGAGCGGACATGGGCAGAGCGATGGTGGCCAGGCTAGGGCTGGGGTTGC
TGCTTCTGGCACTGCTCCTACCCACGCAGATTTACTGCAACCAAACATCTGTTGCACCGT
TTCCCGGTAACCAGAATATTTCTGCTTCCCCAAATCCAAGTAACGCTACCACCAGAGGGG
GTGGCAGCTCCTGCAGTCCACAGCTGGTCTCCTGGGCTCTCTCTCTCTCTTCCACAT
CTCTACTGTTAGAGACTCAGGCCAGGAAACGTCTCTACTTCCCCATCCTCTAGACCTACC
CCAAATGGCAACCACAAGTCCAATGTGATCAGGAAGAAACAGGTCCACCTCGAATTGGCT
GTTACCATATCTCAACAGAAAACACGGAGAATTCGAAATTCGACGGGATTAAAGGACGCG
TGAAAGGTTTGAGAGAAGAGAGATGCCGCTATTGAATCTGCTGGAGTTTTACATCCCAAG
ATGAAGACAGCATTCAGAATTGATGTGATTTCCTTGAATGTGGCTTAGGAAAAGTGGACA
CTTAAAACTCTCACTTGAAATTGGGCACAGGTTTGATGTAGAGATAAGGACGGGGTGCGG
AATGGAGACCCATTTTGTCATTGATTCATCTGACCGATAAGGCCATAGTGCAGTTAGGTG
ATATTCGAAAGCTTCTTTGATGCTCTTTATGTATATGTTGGAAGGAACTACCAGGCGTTG
CTTTAAATTCCCAATGTGTTGTTTCGTTACTACTAATTTAATACCGTAAGCTCTAGGTAA
AGTTCCATGTTGTTGAACTCTGACTGTTCTCTTTGGAATTGAACGTTTTGCATCCTCCTC
CTGTGGCTTTAGGTCTGACATTGTATTTGACCTTTACTAGTAATTAACATGTGCCAGGCA
ATGGTGGATTGGAACCCATCCCCAAGTCCAGCCACCACTGAATAAATCTGATTTCAAAAG
TCAAACAGTAGACATTTCCCATTGTCGTTTCTCACTCACCACAAGCACCAAATTCACTAG
AGTACACTGGTTCCAGAGAGCAGAATCATGTTGGCCTTGGCTAATTTCAAAATGCTGTCT
TTTACTTTGGTATATGTTGAGGGCTTTTCATAATTTAAAGTGTGTTCTGTTAGCAAGGC
AAAAATTATGAGTCTTAATTCTACAGGCAAATATGCAAAGGAGCCAAAACTGTAAACCCA
GCATTTGGGATGTGAAGACTGGAAGCTAACTCTCATTGAATTCACAAAGTCTTTTATACA
ATTTCTGTACATACTTTTTTTTTTTTAAGAGAAAAACAAACGGTGGATCAGAATAGCCA
CGTTTGGAATACTTTGGTTATCCATTCATATTTTAGATAGTTATTGGTCCTGTGCCTGA
AAGGGGGCTTGGTTCTACCGTAAGTTTTTCCAATTTCCTTGATATACACATACCTTCTAA
AACCTAGACATTTCCTGAAAAAAATCTTTTGTTCGCATGGTCACACACTGATGCTTACCC
GTACAGTAGTCTTGATAACCAGAGTCATTTCTCCATCTTTAGAAACCTTCCTGGGAAGA
AGGAGAGCTCACAGACCCGAAGCTACTGTGTGTGAATGAACACTCCCCTTGCCTCACA
CCTGAATGCTGTACATCTATTTGATTGTAAATTGTGTTTGTGTATTTATGCTTTGATTCA
TAGTAACTTCTCATGTTATGGAATTGATTTGCATTGAACACAAACTGTAAAAAAAAAAA
AAAAAGGGCGGCCGCCGCCCGCG
ATGGCCCCGCAGCAAGGCCGGCCGGCGCTGCCCGCCCGCTGCGAGCCGCCGGCGGCGCCG
CCGGTACCGCCTCGCCGAGAGCGCGGGGGGCGCGGGGCGCGCGGGCCCGGGGTGTCCGGG
GGTCGGGGGCGCGCGGGCGGCGCCGAGGGACGCGGCGTCAAGTGCGTGCTGGTCGGCGAC
GGCGCGGTGGGCAAGACCAGCCTGGTGGTCAGCTACACCACTAACGGCTACCCCACCGAG
TACATCCCTACGGCCTTCGACAACTTCTCGGCCGTGGTGTCTGTAGATGGGCGGCCTGTG
AGACTCCAGCTCTGTGACACTGCAGGACAGGATGAGTTTGACAAGCTGAGGCCCCTCTGC
TACACCAACACAGACATCTTCCTGCTGTGCTTCAGCGTGGTGAGCCCCACATCCTTCCAG
AACGTGGGCGAGAAGTGGGTTCCAGAGATTCGACGTCACTGCCCAAAGGCCCCCATCATC
CTGGTCGGGACACAGTCGGACCTCAGGGAGGACGTCAAAGTGCTCATAGAACTGGACAAG
TGCAAAGAGAAGCCGGTGCCTGAAGAGGCGGCGAAGCTGTGCGCGGAGGAAGTCAAAGCT
GTCTCCTACATCGAGTGCTCAGCGTTGACTCAGAAAAACCTCAAAGAGGTTTTCGACGCC
GCCATTGTTGCTGGTATCCAGCACTCAGACTCCAGCTACAGCCAAAGAAGTCTAAAAGC
AGGACCCCGGATAAGGTGCGGGACCTGTCCAAGTCTTGGTGGAGGAAGTATTGCTGCCTG
GCCTGACTCTCGCAAATAGCAGGTGTTTAAGCTGCAACAGCTCTTTATGGACGAGGCTGT
CATAGGATGAGCCCCAAAGCACCCTCTTCTGCCCTTAACTTCCTGTGTGCGGGAGCTTAG
GGCTGAGATTCATATGCAAAATACGTTTTTTAAAAATTGAAAGTTACATTTTTTTCTG
```

FIG._13A

```
TTAAGTCTGGAAGCTTTGAGCTGTAGACCTCCGGATTAATTTATATTCCATATGAAAAGG
GCTCTTCAAAGCGGGGTGTCAGCATGAAGTTCTGCTGTGTTGTACAGGACAAAGGAGAAT
GAATGGGACCTTCTCCTGATTAAGGGCTACTGAGGGCTCAGTGCAGGGCACGTGTGCACC
AGGCTTGGTGAGAGTGAGCAAGCGTGAGCTTTGAAACCACACGAGCCACCCCGGTTTTG
TAAGGGCAAAGATCTGAAACCAGCAAGGGCCTTCTGCTTACGAAACCTCGAGCCCATCCC
TTCTGTTTACTCAGATTCTCTTAGGATTTTAAAACAACCAAACATCCCACAGCCTACTGG
CATAGTGTTGGCGAACAGTGCACTTGCTTGTTACGGTTTTGTTTTGTTTTTTAAATCAC
GTGACCAGTTATATTGCTATGAAAATGGTGGAGATGCCTCGTAGAAGGCGAGTGCTGGT
GCACATGTGACATTTTCTTCAGGGAGCGACTCATGGTGAGACCAGAGAGGGCTCTTAGCT
TGCAGGACTGGCTTCTGCAGGGCATCTGTGTCCTGCTGTTAAAAGCAGGAGGAGGTGCTT
GTCTGGGAGCTTTAAGTGTGCTGGGCTCATATCGTCCCGTTTGCAAGGAATTGGGCCACC
TTGAGAGGCCATAGTTGATGGCTATGGGACACACACACACTTTTTCCTTAAGTCCACCAA
AATGCCTGCCTGTACACACACACACACACACACACACACACACACACACACACACTGGCT
GGTTTGCTGATGGAACCCTTAGACCACCCTCCCACCCCCACCCCTCCCCAAGCATGGCTG
CAAGTGTCAGGGCACCACACCTTCCTCTTCTTGACATTTCTTTGAACAGACATCATTTG
TAGGATCTTAATTTATACATTTTTTCAGGTCATAAAATGTGGGATGAACATACTTTGAA
CCCCAGTGCCTTCAGGGTCCATTGACTAGGGAGGCACTGTCTTAGGGGACAGGTATGTGC
AAGGCCTTACCCACCAGTGGCTTCTCGCTGCAGGTCATGTTTGTGGCACTTGTTCTTTAA
GGTGAGGGTCTTATGACCGACTGTTCTGAGACAGCCCTGTGTCAGGCAAGCTCTTTCACA
GGGTTGTAGGTATTTCCAAGACGCCATAGGAACCAGACAGTGAATCATAGCTATCAGTTT
GCTGTGGGCAAGGAACCTCTTTTTGGCCACCTGGTAACAAAATTTTATGTCTGTAAATTT
TTTCTTGCTATTTAAAAAAAAAAAAAAAAAA
```

FIG._13B

```
5'-CCCACGCGTCCGCGGACGCGTGGTTCAGGGTCCATTGACTAGGGAGGCACTGTCTTAGGG
GACAGGTATGTGCAAGGCCTTACCCACCAGTGGCTTCTCGCTGCAGGTCATGTTTGTGGC
ACTTGTTCTTTAAGGTGAGGGTCTTATGACCGACTGTTCTGAGACAGCCCTGTGTCAGGC
AAGCTCTTTCACAGGGTTGTAGGTATTTCCAAGACGCCATAGGAACCAGACAGTGAATCA
TAGCTATCAGTTTGCTGTGGGCAAGGAACCTCTTTTTGGCCACCTGGTAACAAAATTTTA
TGTCTGTAAATTTTTTCTTGCTATTTAAAAAAAAAAATCAATCTTACGTTTTCTGTAGG
AAAAAAAAAACAAGTAAAAGAACAGGCCATATTTCAGGTCAAAGGCTTCTTCCTGCTGG
TAAATGGGACTGAAGACTTTCTTACATCATTATTAAAAGGCTAATTGCTGAACCACTAGA
GTATATGAACTGTTTGTGAATGATATTAGCCATAGTCTCCTGAGGTGTTTCCTTGTGGCC
TGAGTGGTAACATTGTTTGCTTATGGAGATGCTGTAACTGACCTAGTGACTCAGCTTAT
CCTATTGTGCATGGCTGTCTGGAAAGCCAGCGTACAAGTGGGCTTTGCCTGCCCTGTGT
ACAGAGGGTGGGTGGGAAAGAGTGAATTATTTAATTTTAAATGTTATAATAAAGCCAATG
TAGTTGAGACCAAGGAAATGAGCATTGAGAACACAAACTTGAAGTCTGGTGCCAGGGTTG
TTGGACCTCACACCCTGTCTCTGAGCCACCCGGAAGTGACATAAAGGACGCTGTGTGATC
A
```

FIG._17

5'-CCCACGCGTCCGTATGAAAATGGTGGAGATGCCTCGTAGAAGGCGAGTGCTGGGTGCACATG
TGACATTTTCTTCAGGGAGCGACTCATGGTGAGACCAGAGAGGGCTCTTAGCTTGCAGGAC
TGGCTTCTGCAGGGCATCTGTGTCCTGCTGTTAAAAGCAGGAGGAGGTGCTTGTCTGGGAGCTTTAA
GTGTGCTGGGCTCATATCGTCCCGTTTGCAAGGAATTGGGCCACCTTGAGAGGCCA
TAGTTGATGGCTATGGGACACACACACACTTTTTCCTTAAGTCCACCAAAATGCCTGCCTGTA
CACACACACACACACACACACACACACACACACACACACACTGGCTGGTTTGCTGATGGAA
CCCTTAGACCACCCTCCCACCCCCACCCCTCCCCAAGCATGGCTGCAAGTGTCAGGGCACCACAC
CTTCCTCTTCTTGACATTTCTTTGAACAGACATCATTTGTAGGATCTTAATTTATAC
ATTTTTTTCANGTCATAAAATGTGGGATGAACATACTTTGAACCCCAGTGCCTTCAGGGTC
CATTGACTAGGGAGGCACTGTCTTAGGGGACAGGTATGTGCAAGGCCTTACCCACCAGT
GGCTTCTCGCTGCAGGTCATGTTTGTGGCACTTGTTCTTTAAGGTGAGGGTCTTATGACCG
ACTGTTCTGAGACAGCCCTGTGTCAGGCAAGCTCTTTCACAGGGTTGTAGGTATTTC
CAAGACGCCATAGGAACCAGACAGTGAATCATAGCTATCAGTTTGCTGTGGGCAAGGAACC
TCTTTTTGGCCACCTGGTAACAAAATTTTATGTCTGTAAATTTTTTCTTGCTATTTAAAA
AAAAAAATCAATCTTACGTTTTTCTGTAGGAAAAAAAAAAACAAGTAAAAGAACAGGCCAT
ATTTCAGGTCAAAGGCTTCTTCCTTCTGGTAAATGGGACTGAAGACTTTCTTACATCA
TTATTAAAAGGCTAATTGCTGAACCACTAGAGTATATGAACTGTTTGTGAATGATATTAGC
CATAGTCTCCTGAGGTGTTTCCTTGTGGCCTGAGTGGTAACATTGTTTGCTTATGGAGA
TGCTGTAACTGACCTAGTGACTCAGCTTATCCTATTGTGCATGGCTGTCTGGAAAGCCAG
CGTACAAGTGGGGCTTTGCCTGCCCTGTGTACAGAGGGTGGGTGGGAAAGAGTGAATT
ATTTAATTTTAAATGTTATAATAAAGCCAATGTAGTTGAGACCAAGGAAATGAGCATTGAGA
ACACAAACTTGAAGTCTGGTGCCAGGGTTGTTGGACCTCACACCCTGTCTCTGAGCCACC
CGGAAGTGACATAAAGGACGCTGTGTGATCA

FIG._15

```
5'-CCCACGCGTCCGGTGACCAGTTATATTGCTATGAAAATGGTGGAGATGCCTCGTAGAAGG
CGAGTGCTGGGTGCACATGTGACATTTTCTTCAGGGAGCGACTCATGGTGAGACCAGAGA
GGGCTCTTAGCTTGCAGGACTGGCTTCTGCAGGGCATCTGTGTCCTGCTGTTAAAAGCAG
GAGGAGGTGCTTGTCTGGGAGCTTTAAGTGTGCTGGGCTCATATCGTCCCGTTTGCAAGG
AATTGGGCCACCTTGAGAGGCCATAGTTGATGGCTATGGACACACACACACTTTTTCCT
TAAGTCCACCAAAATGCCTGCCTGTACACACACACACACACACACACACACACACACACA
CACACACTGGCTGGTTTGCTGATGGAACCCTTAGACCACCCTCCCACCCCCACCCCTCCC
CAAGCATGGCTGCAAGTGTCAGGGCACCACACCTTCCTCTTCTTGACATTTCTTTGAACA
GACATCATTTTGTAGGATCTAATTTATACATTTTTTCAGGTCATAAAATGTGGGATGAA
CATACTTTGAACCCCAGTGCCTTCAGGGTCCATTGACTAGGGAGGCACTGTCTTAGGGGA
CAGGTATGTGCAAGGCCTTACCCACCAGTGGCTTCTCGCTGCAGGTCATGTTTGTGGCAC
TTGTTCTTTAAGGTGAGGGTCTTATGACCGACTGTTCTGAGACAGCCCTGTGTCAGGCAA
GCTCTTTCACAGGGTTGTAGGTATTTCCAAGACGCCATAGGAACCAGACAGTGAATCATA
GCTATCAGTTTGCTGTGGGCAAGGAACCTCTTTTGGCCACCTGGTAACAAAATTTTATG
TCTGTAAATTTTTTCTTGCTATTTAAAAAAAAAATCAATCTTACGTTTTTCTGTAGGAA
AAAAAAAAACAAGTAAAAGAACAGGCCATATTTCAGGTCAAAGGCTTCTTCCTGCTGGTA
AATGGGACTGAAGACTTTCTTACATCATTATTAAAAGGCTAATTGCTGAACCACTAGAGT
ATATGAACTGTTTGTGAATGATATTAGCCATAGTCTCCTGAGGTGTTTCCTTGTGGCCTG
AGTGGTAACATTGTTTGCTTATGGAGATGCTGTAACTGACCTAGTGACTCAGCTTATCC
TATTGTGCATGGCTGTCTGGAAAGCCAGCGTACAAGTGGGGCTTTGCCTGCCCTGTGTAC
AGAGGGTGGGTGGGAAAGAGTGAATTATTTAATTTTAAATGTTATAATAAAGCCAATGTA
GTTGAGACCAAGGAAATGAGCATTGAGAACACAAACTTGAAGTCTGGTGCCAGGGTTGTT
GGACCTCACACCCTGTCTCTGAGCCACCCGGAAGTGACATAAAGGACGCTGTGTGATCAA
GTTCTGGACACTTTTCTGGGATGCGTACCACTGGACTATTTATGTCACAAATCTAGTGGG
TTGACGCTGCCCTGCAAGTTTTCAATGTCCCTGCATCCTATGAAGTCATAATGTCTGACT
GTACTGGAGGTTTTCCTGCATTTTTTACTTTTCGAAAATAGAGGTTTGGGCTGAGAATTC
TAAACGCATGTGCCTGGGTGGGACGTCAAGTCAGGGTTCTCATCAAAGCTGAGAAGTGGC
TGGAATGTTCAGCTTGGTGTCTGGGGCAGGCTCCAAAATCGTCACCTCAAGCATGCGTGC
AAGCAAACTTCCGAGAACTCCGTTTTCTGCTCGGCAGACGTGTGAGCAGCTACCCAGAAG
TCTCAAGCCAAAAGGGGAGCCTCGCTCGCTGGCTCCTCTGCAGGTGCCTTATCGACCTGT
GCTCTTCTCTTTTCCCGTGTCAAAGATGTTGGACAGGATCTTGTACTTGAAACATACTAC
AAATGAGTTACTATGAAATAAATTCTGACCTGTGGACCGAAAAAAAAAAAAAAAAAAAAA
AAAAAAAAAAAAAAAAAAAAAAAAAAAAAA
```

FIG._16

POLYPEPTIDES AND NUCLEIC ACIDS ENCODING SAME

This is a continuation of non-provisional application Ser. No. 09/182,562, filed Oct. 29, 1998, now abandoned, claiming priority to provisional application No. 60/063,704, filed Oct. 29, 1997, and to provisional application No. 60/073,612, filed Feb. 4, 1998, the entire disclosures of which applications are hereby incorporated by reference.

This invention was made with government support under grant no. 5PO1 CA41086, awarded by the National Institutes of Health, National Cancer Institute. The government has certain rights in the invention.

FIELD OF THE INVENTION

The present invention relates generally to the identification and isolation of novel DNA and to the recombinant production of novel polypeptides useful in the management of malignancies.

BACKGROUND OF THE INVENTION

Wnts are encoded by a large gene family whose members have been found in round worms, insects, cartilaginous fish, and vertebrates. Holland et al., *Dev. Suppl.*, 125-133 (1994). Wnts are thought to function in a variety of developmental and physiological processes since many diverse species have multiple conserved Wnt genes. McMahon, *Trends Genet.*, 8: 236-242 (1992); Nusse and Varmus, *Cell*, 69: 1073-1087 (1992). Wnt genes encode secreted glycoproteins that are thought to function as paracrine or autocrine signals active in several primitive cell types. McMahon, supra; Nusse and Varmus, supra. The Wnt growth factor family includes more than ten genes identified in the mouse (Wnt-1, -2, -3A, -3B, -4, -5A, -5B, -6, -7A, -7B, -8A, -8B, -10B, -11, -12, and -13) (see, e.g., Gavin et al., *Genes Dev.*, 4: 2319-2332 (1990); Lee et al., *Proc. Natl. Acad. Sci. USA*, 92: 2268-2272 (1995); Christiansen et al., *Mech. Dev.*, 51: 341-350 (1995)) and at least nine genes identified in the human (Wnt-1, -2, -3, -5A, -7A, -7B, -8B, -10B, and -11) by cDNA cloning. See, e.g., Vant Veer et al., *Mol. Cell. Biol.*, 4: 2532-2534 (1984).

The Wnt-1 proto-oncogene (int-1) was originally identified from mammary tumors induced by mouse mammary tumor virus (MMTV) due to an insertion of viral DNA sequence. Nusse and Varmus, *Cell*, 31: 99-109 (1982). In adult mice, the expression level of Wnt-1 mRNA is detected only in the testis during later stages of sperm development. Wnt-1 protein is about 42 KDa and contains an amino-terminal hydrophobic region, which may function as a signal sequence for secretion. Nusse and Varmus, supra, 1992. The expression of Wnt-2/irp is detected in mouse fetal and adult tissues and its distribution does not overlap with the expression pattern for Wnt-1. Wnt-3 is associated with mouse mammary tumorigenesis. The expression of Wnt-3 in mouse embryos is detected in the neural tubes and in the limb buds. Wnt-5a transcripts are detected in the developing fore- and hind limbs at 9.5 through 14.5 days and highest levels are concentrated in apical ectoderm at the distal tip of limbs. Nusse and Varmus, supra (1992). Recently, a Wnt growth factor, termed Wnt-x, was described (WO95/17416) along with the detection of Wnt-x expression in bone tissues and in bone-derived cells. Also described was the role of Wnt-x in the maintenance of mature osteoblasts and the use of the Wnt-x growth factor as a therapeutic agent or in the development of other therapeutic agents to treat bone-related diseases.

Wnts may play a role in local cell signaling. Biochemical studies have shown that much of the secreted Wnt protein can be found associated with the cell surface or extracellular matrix rather than freely diffusible in the medium. Papkoff and Schryver, *Mol. Cell. Biol.*, 10: 2723-2730 (1990); Bradley and Brown, *EMBO J.*, 9: 1569-1575 (19:90).

Studies of mutations in Wnt genes have indicated a role for Wnts in growth control and tissue patterning. In Drosophila, wingless (wg) encodes a Wnt-related gene (Rijsewik et al., *Cell*, 50: 649-657 (1987)) and wg mutations alter the pattern of embryonic ectoderm, neurogenesis, and imaginal disc outgrowth. Morata and Lawerence, *Dev. Biol.*, 56: 227-240 (1977); Baker, *Dev. Biol.*, 125: 96-108 (1988); Klingensmith and Nusse, *Dev. Biol.*, 166: 396-414 (1994). In *Caenorhabditis elegans*, lin-44 encodes a Wnt homolog which is required for asymmetric cell divisions. Herman and Horvitz, *Development*, 120: 1035-1047 (1994). Knock-out mutations in mice have shown Wnts to be essential for brain development (McMahon and Bradley, *Cell*, 62: 1073-1085 (1990); Thomas and Cappechi, *Nature*, 346: 847-850 (1990)), and the outgrowth of embryonic primordia for kidney (Stark et al., *Nature*, 372: 679-683 (1994)), tail bud (Takada et al., *Genes Dev.*, 8: 174-189 (1994)), and limb bud. Parr and McMahon, *Nature*, 374: 350-353 (1995). Overexpression of Wnts in the mammary gland can result in mammary hyperplasia (McMahon, supra (1992); Nusse and Varmus, supra (1992)), and precocious alveolar development. Bradbury et al., *Dev. Biol.*, 170: 553-563 (1995).

Wnt-5a and Wnt-5b are expressed in the posterior and lateral mesoderm and the extraembryonic mesoderm of the day 7-8 murine embryo. Gavin et al., supra. These embryonic domains contribute to the AGM region and yolk sac tissues from which multipotent hematopoietic precursors and HSCs are derived. Dzierzak and Medvinsky, *Trends Genet.*, 11: 359-366 (1995); Zon et al., in Gluckman and Coulombel, ed., Colloque, *INSERM*, 235: 17-22 (1995), presented at the Joint International Workshop on Foetal and Neonatal Hematopoiesis and Mechanism of Bone Marrow Failure, Paris France, Apr. 3-6, 1995; Kanatsu and Nishikawa, *Development*, 122: 823-830 (1996). Wnt-5a, Wnt-10b, and other Wnts have been detected in limb buds, indicating possible roles in the development and patterning of the early bone microenvironment as shown for Wnt-7b. Gavin et al., supra; Christiansen et al., *Mech. Devel.*, 51: 341-350 (1995); Parr and McMahon, supra.

The Wnt/Wg signal transduction pathway plays an important role in the biological development of the organism and has been implicated in several human cancers. This pathway also includes the tumor suppressor gene, APC. Mutations in the APC gene are associated with the development of sporadic and inherited forms of human colorectal cancer. The Wnt/Wg signal leads to the accumulation of beta-catenin/Armadillo in the cell, resulting in the formation of a bipartite transcription complex consisting of beta-catenin and a member of the lymphoid enhancer binding factor/T cell factor (LEF/TCF)HMG box transcription factor family. This complex translocates to the nucleus where it can activate expression of genes downstream of the Wnt/Wg signal, such as the engrailed and Ultrabithorax genes in Drosophila. The downstream target genes of Wnt-1 signaling in vertebrates that presumably function in tumorigenesis, however, are currently unknown.

For a most recent review on Wnt, see Cadigan and Nusse, *Genes & Dev.*, 11: 3286-3305 (1997).

Another family of proteins, the Rho and Rac subfamilies of Ras proteins, have been implicated in transformation by oncogenic ras. Thus far, activation of the pathways governed by three members of the Rho family of GTP-binding proteins, CDC42, Rac, and Rho, has been found to be necessary for Ras transformation. Activating Ras mutations occur in about 30% of all human tumors, indicating that elements of the CDC42, Rac, and Rho signaling pathways are drug targets for cancer therapy. These three members play a central role in the organization of the actin cytoskeleton and regulate transcription. Like Ras, the Rho proteins interact directly with protein kinases, which are likely to serve as downstream effector targets of the activated GTPase. The roles of the different Rho proteins in Ras transformation appear to be distinct: CDC42 specifically controls anchorage-independent growth, whereas Rac controls Rac-induced mitogenicity. The small G proteins Rac1, Rac2, and Rac3 are highly related GTPases. Didsbury et al., *J. Biol. Chem.*, 264: 16378-16382 (1989); Moll et al., *Oncogene*, 6: 863-866 (1991); Shirsat et al., *Oncogene*, 5: 769-772 (1990); Haataja et al., *J. Biol. Chem.*, 272: 20384-20388 (1997). RAC3 is located at chromosome 17q23-25, a region frequently deleted in breast cancer. Cropp et al., *Proc. Natl. Acad. Sci. USA*, 87: 7737-7741 (1990); Cornelis et al., *Oncogene*, 8: 781-785 (1993). Recent data have provided evidence that constitutive activity of the Rho-family GTPases is associated with cytoskeletal rearrangement and disorganized growth, motility, and invasiveness of cells, all hallmarks of neoplasia.

There is a need to elucidate the further members of the above families, including cell-surface molecules that may be tumor-specific antigens or proteins that serve a regulatory function in initiating the Wnt pathway of tumorigenesis. These would also include downstream components of the Wnt signaling pathway that are important to the transformed phenotype and the development of cancer. There is also a need to identify other proteins that, perhaps in conjunction with beta-catenin, regulate Wnt-1 downstream genes, as well as GTPases.

SUMMARY OF THE INVENTION

Several putative Wnt-1-induced genes have been identified at the mRNA level in a high-throughput cDNA substraction experiment. Thus, applicants have identified novel cDNA clones (clone 65 and clone 320) that encode novel polypeptides that are Wnt induced, designated as clone 65 and clone 320, respectively. The clone 65 molecules have homology to the Rac and Rho subfamily noted above.

In one embodiment, this invention provides isolated nucleic acid comprising DNA having at least about 800 nucleotides and at least about a 70% sequence identity to (a) a DNA molecule encoding a human clone 65 polypeptide comprising the sequence of amino acids 1 to 258 of FIGS. 5A-5D (SEQ ID NO:3), or (b) the complement of the DNA molecule of (a). Preferably, this nucleic acid has at least one clone 65 or 320 biological activity.

In another aspect, the invention provides isolated nucleic acid comprising DNA having at least about 700 nucleotides and at least about a 95% sequence identity to (a) a DNA molecule encoding a human clone 65 polypeptide comprising the sequence of amino acids 1 to 258 of FIGS. 5A-5D (SEQ ID NO:3), or (b) the complement of the DNA molecule of (a). Preferably, this nucleic acid comprises DNA encoding a human clone 65 polypeptide having amino acid residues 1 to 258 of FIGS. 5A-5D (SEQ ID NO:3), or the complement thereof.

In a still further aspect, the invention provides isolated nucleic acid comprising DNA having at least about 800 nucleotides and at least about a 70% sequence identity to (a) a DNA molecule encoding a mouse clone 65 polypeptide comprising the sequence of amino acids 1 to 261 of FIGS. 1A and 1B (SEQ ID NO:6), or (b) the complement of the DNA molecule of (a). Preferably, this nucleic acid comprises DNA having at least about a 85% sequence identity to (a) a DNA molecule encoding a mouse clone 65 polypeptide comprising the sequence of amino acids 1 to 261 of FIGS. 1A and 1B (SEQ ID NO:6), or (b) the complement of the DNA molecule of (a). Preferably, this nucleic acid comprises DNA encoding a mouse clone 65 polypeptide having amino acid residues 1 to 261 of FIGS. 1A and 1B (SEQ ID NO:6), or the complement thereof.

In a still further embodiment, the invention provides an isolated nucleic acid comprising DNA having at least about 800 nucleotides and at least about a 70% sequence identity to (a) a DNA molecule encoding the same full-length polypeptide encoded by the human clone 65 polypeptide cDNA in ATCC Deposit No. 209536 (pRK5E.h.WIG-3.65.4A), or (b) the complement of the DNA molecule of (a). Preferably, this nucleic acid comprises DNA having at least about a 95% sequence identity to (a) a DNA molecule encoding the same full-length polypeptide encoded by the human clone 65 polypeptide cDNA in ATCC Deposit No.209536 (pRK5E.h.WIG-3.65.4A), or (b) the complement of the DNA molecule of (a).

In another embodiment, the invention provides isolated nucleic acid comprising SEQ ID NO: 11, 12, 13, 14, 15, 16, 17, 18, or 19, and an isolated clone 65 polypeptide encoded by such a nucleic acid.

A still further aspect of the invention involves a process for producing a clone 65 polypeptide comprising culturing a host cell comprising clone 65-encoding nucleic acid under conditions suitable for expression of the clone 65 polypeptide and recovering the clone 65 polypeptide from the cell culture.

Further provided is an isolated clone 65 polypeptide encoded by the clone 65-encoding nucleic acid. Preferably, this polypeptide is human clone 65 or mouse clone 65.

In another embodiment, the invention provides an isolated nucleic acid having at least about 800 nucleotides and produced by hybridizing a test DNA molecule under stringent conditions with (a) a DNA molecule encoding a human clone 65 polypeptide comprising the sequence of amino acids 1 to 258 of FIGS. 5A and 5B (SEQ ID NO:3), or (b) the complement of the DNA molecule of (a), and, if the test DNA molecule has at least about a 70% sequence identity to (a) or (b), isolating the test DNA molecule.

Also provided is a polypeptide produced by (i) hybridizing a test DNA molecule under stringent conditions with (a) a DNA molecule encoding a human clone 65 polypeptide comprising the sequence of amino acids 1 to 258 of FIGS. 5A-5D (SEQ ID NO:3), or (b) the complement of the DNA molecule of (a), and if the test DNA molecule has at least about a 70% sequence identity to (a) or (b), (ii) culturing a host cell comprising the test DNA molecule under conditions suitable for expression of the polypeptide, and (iii) recovering the polypeptide from the cell culture.

Also provided by the invention is isolated nucleic acid encoding mouse clone 320 comprising DNA having at least about 500 nucleotides and having at least about a 97% sequence identity to (a) a DNA molecule comprising the sequence of nucleotides 1 to 2822 of FIG. 2 (SEQ ID NO:7), or (b) the complement of the DNA molecule of (a). Further provided is isolated nucleic acid encoding mouse clone 320 comprising DNA having at least about 700 nucleotides and having at least about a 70% sequence identity, more preferably at least about an 80% sequence identity, more preferably still at least about a 90% sequence identity, and yet more preferably at least about a 95% sequence identity, and more preferably at least about a 100% sequence identity, to (a) a DNA molecule comprising the sequence of nucleotides 1 to 727 of FIG. 3 (SEQ ID NO:8), or (b) the complement of the DNA molecule of (a).

Also provided is isolated nucleic acid encoding mouse clone 320 comprising DNA having at least about 700 nucleotides and having at least 75% sequence identity to (a) a DNA molecule comprising the sequence of nucleotides 1-2526 of FIGS. 4A and 4B (SEQ ID NO: 9), or (b) the complement of the DNA molecule of (a). More preferably, this nucleic has at least about 90% sequence identity to (a) or (b).

Also provided by the invention is isolated nucleic acid encoding mouse clone 320 comprising DNA having at least about 500 nucleotides and having at least about a 97% sequence identity to (a) a DNA molecule comprising the sequence of nucleotides 1 to 2822 of FIG. 2 (SEQ ID NO:7), or (b) the complement of the DNA molecule of (a) and comprising DNA having at least about 700 nucleotides and having at least about a 70% sequence identity, more preferably at least about an 80% sequence identity, more preferably still at least about a 90% sequence identity, and yet more preferably at least about a 95% sequence identity, and more preferably at least about a 100% sequence identity, to (c) a DNA molecule comprising the sequence of nucleotides 1 to 727 of FIG. 3 (SEQ ID NO:8), or (d) the complement of the DNA molecule of (c).

Further provided is isolated nucleic acid encoding mouse clone 320 comprising DNA having at least about 500 nucleotides and having at least about a 97% sequence identity to (a) a DNA molecule comprising the sequence of nucleotides 1 to 2822 of FIG. 2 (SEQ ID NO:7), or (b) the complement of the DNA molecule of (a) and comprising DNA having at least about 700 nucleotides and having at least a 75% sequence identity to (c) a DNA molecule comprising the sequence of nucleotides 1 to 2526 of FIGS. 4A and 4B (SEQ ID NO: 9), or (d) the complement of the DNA molecule of (c).

Additionally provided is isolated nucleic acid encoding mouse clone 320 comprising DNA having at least about 700 nucleotides and having at least about a 70% sequence identity to (a) a DNA molecule comprising the sequence of nucleotides 1 to 727 of FIG. 3 (SEQ ID NO:8), or (b) the complement of the DNA molecule of (a) and comprising DNA having at least about 700 nucleotides and having at least a 75% sequence identity to (c) a DNA molecule comprising the sequence of nucleotides 1 to 2526 of FIGS. 4A and 4B (SEQ ID NO: 9), or (d) the complement of the DNA molecule of (c).

Still further provided is isolated nucleic acid encoding mouse clone 320 comprising DNA having at least about 500 nucleotides and having at least about a 97% sequence identity to (a) a DNA molecule comprising the sequence of nucleotides 1 to 2822 of FIG. 2 (SEQ ID NO:7), or (b) the complement of the DNA molecule of (a) and comprising DNA having at least about 700 nucleotides and having at least a 75% sequence identity to (c) a DNA molecule comprising the sequence of nucleotides 1 to 2526 of FIGS. 4A and 4B (SEQ ID NO: 9), or (d) the complement of the DNA molecule of (c) and comprising DNA having at least about 700 nucleotides and having at least about a 70% sequence identity to (e) a DNA molecule comprising the sequence of nucleotides 1-727 of FIG. 3 (SEQ ID NO:8), or (f) the complement of the DNA molecule of (e).

Also provided by the invention is isolated nucleic acid encoding mouse clone 320 comprising DNA having at least about 500 nucleotides and having at least about a 95% sequence identity to (a) a DNA molecule encoding the same polypeptide encoded by the mouse clone 320 polypeptide cDNA in ATCC Deposit No. 209534_ (pRK5E.m.WIG-4.320.9), or (b) the complement of the DNA molecule of (a). Preferably, the nucleic acid is about 3 kilobases in length.

More preferably, the nucleic acid comprises DNA that encodes the same polypeptide encoded by the mouse clone 320 polypeptide cDNA in ATCC Deposit No. 209534 (pRK5E.m.WIG-4.320.9).

In another aspect, the invention provides a polypeptide encoded by the clone 320 nucleic acid above.

Further provided is an isolated nucleic acid having at least about 500 nucleotides and produced by hybridizing a test DNA molecule under stringent conditions with (a) a DNA molecule encoding the same polypeptide encoded by the mouse clone 320 polypeptide cDNA in ATCC Deposit No. 209534 (pRK5E.m.WIG-4.320.9), or (b) the complement of the DNA molecule of (a), and, if the test DNA molecule has at least about a 95% sequence identity to (a) or (b), isolating the test DNA molecule.

In a still further embodiment, the invention provides a polypeptide produced by (i) hybridizing a test DNA molecule under stringent conditions with (a) a DNA molecule encoding the same polypeptide encoded by the mouse clone 320 polypeptide cDNA in ATCC Deposit No. 209534 (pRK5E.m.WIG-4.320.9), or (b) the complement of the DNA molecule of (a), and if the test DNA molecule has at least about a 95% sequence identity to (a) or (b), (ii) culturing a host cell comprising the test DNA molecule under conditions suitable for expression of the polypeptide, and (iii) recovering the polypeptide from the cell culture.

Preferably the complements of the DNA molecules herein remain stably bound to the primary sequence under at least moderate, and optionally, under high stringency conditions.

Also provided are vectors comprising the above nucleic acids, host cells comprising the vector, preferably wherein the cell is a Chinese hamster ovary (CHO) cell, an *E. coli* cell, a baculovirus-infected cell, or a yeast cell.

Additionally provided are a chimeric molecule comprising one of the above polypeptides or an inactivated variant thereof, fused to a heterologous amino acid sequence, wherein the heterologous amino acid sequence may be, for example, an epitope tag sequence or an Fc region of an immunoglobulin. Also provided is an antibody which specifically binds to one of the above polypeptides, wherein the antibody can be a monoclonal antibody.

Further provided are a composition comprising one of the above polypeptides and a carrier therefor, and a composition comprising an antagonist to one of the polypeptides and a carrier therefor. Preferably, these compositions may also comprise a chemotherapeutic agent or growth-inhibitory agent.

In another embodiment, the invention provides a method for treating a clone 65- or 320-related disorder in a mammal comprising administering to the mammal an effective amount of any of the above compositions. Preferably, the disorder is a malignant disorder or arteriosclerosis. More preferably, the malignant disorder is breast cancer, ovarian cancer, colon cancer, or melanoma.

Also provided herein is a kit comprising one of the above clone 65 or 320 polypeptides or clone 65 or 320 antagonists, such as anti-clone 65 antibodies or anti-clone 320 antibodies, and instructions for using the antibody to detect a cancer induced by Wnt.

Also provided is a method for inducing cell death comprising exposing a cell which is induced by Wnt to an effective amount of one of the above clone 65 or 320 polypeptides or clone 65 or 320 antagonists, such as anti-clone 65 or anti-clone 320 antibodies. Preferably, such cell is a cancer cell.

More preferably, the cell is in a mammal, more preferably a human. Optionally, an effective amount of another chemotherapeutic antibody is also exposed to the cell, such as an anti-ErbB2 antibody. Further, optionally the method comprises exposing the cell to a chemotherapeutic agent, a growth-inhibitory agent, or radiation. Optionally, the cell is exposed to the growth-inhibitory agent prior to exposure to the anti-clone 65 or anti-clone 320 antibody.

In a further aspect, the invention provides an article of manufacture, comprising:
 a container;
 a label on the container; and
 a composition comprising an active agent contained within the container; wherein the composition is effective for inducing cell death, the label on the container indicates that the composition can be used for treating conditions characterized by overinduction of Wnt, and the active agent in the composition is one of the polypeptides noted above, or an antagonist to one of the polypeptides such as an antibody.

BRIEF DESCRIPTION OF THE DRAWINGS

FIGS. 1A and 1B show the derived amino acid sequence of a native-sequence mouse clone 65 protein from amino acids 1 to 261 (SEQ ID NO:6) and the nucleotide sequence (and complementary sequence) encoding the protein (SEQ ID NOS:4 and 5, respectively). This is from the mouse clone 65.11.3. A histidine sequence was fused to the heat-stable antigen. The heat-stable antigen sequence has been removed. There is 465 bp of 3' untranslated region and 86 bp of the coding region. The first 139 bp of the sequence has 89% GC content. This is the added region compared to other family members. A potential glycosylation site is at amino acid 88 through 91. A potential protein kinase C phosphorylation site is at amino acids 210 through 212. Potential casein kinase II phosphorylation sites are at amino acids 84 through 87, 122 through 125, 164 through 167, and 202 through 205. Potential N-myristoylation sites are at amino acids 29 through 34, 37 through 42, 46 through 51, and 225 through 240. A potential prenyl group binding site is at amino acids 258 through 261. A potential ATP/GTP-binding site motif A (P-loop) is at amino acids 59 through 66.

FIG. 2 shows a nucleotide sequence (SEQ ID NO:7) contained within the mouse clone 320 polypeptide cDNA in ATCC deposit no. 209534.

FIG. 3 shows another nucleotide sequence (SEQ ID NO:8) contained within the mouse clone 320 polypeptide cDNA in ATCC deposit no. 209534.

FIGS. 4A and 4B show yet another nucleotide sequence (and the complement thereof) (SEQ ID NOS:9 and 10, respectively) contained within the mouse clone 320 polypeptide cDNA in ATCC deposit no. 209534.

FIGS. 5A-D show the derived amino acid sequence of a native-sequence human clone 65 protein from amino acids 1 to 258 (SEQ ID NO:3) and the consensus nucleotide sequence (and complementary sequence) encoding the protein (SEQ ID NOS:1 and 2, respectively), which is derived from three human clones from a human fetal liver library. There are 2955 bp of 3' untranslated region and 777 bp of coding region in the sequence. Potential N-glycosylation sites are from amino acids 85 though 88, amino acids 138 through 141, and amino acids 245 through 248. Potential protein kinase C phosphorylation sites are at amino acids 140 through 142 and 207 through 209. Potential casein kinase II phosphorylation sites are at amino acids 81 through 84, 119 through 122, 161 through 164, and 199 through 202. Potential N-myristoylation sites are at amino acids 26 through 31, 43 through 48, and 222 through 227. A potential ATP/GTP-binding site motif A (P-loop) is at amino acids 56 through 63.

FIG. 6 shows an alignment of the full-length amino acid sequences of the human and mouse clone 65 (SEQ ID NOS:3 and 6, respectively).

FIG. 7 shows a map of the vector pBabe puro (5.1 kb) used to transform cells for purposes of differential expression. The vector includes both unique restriction sites and multiple restriction sites. It is shown here in modified form for Wnt-1 cloning wherein the HindIII site after the SV40 promoter in the original pBabe puro vector has been removed and a HindIII site added to the multiple cloning site of the original pBabe puro vector. Wnt-1 is cloned from EcoRI-HindIII in the multiple cloning site. Constructs derived from this vector are selected in ampicillin (100 µg/ml) and the cells infected in culture are selected in 1.0-2.5 µg/ml puromycin.

FIG. 8 shows the sequences of the PCR-Select® cDNA synthesis primer (SEQ ID NO:20), adaptors 1 and 2 (SEQ ID NOS:21 and 22, respectively) and complementary sequences for the adaptors (SEQ ID NOS:23 and 24, respectively), PCR primer 1 (SEQ ID NO:25), PCR primer 2 (SEQ ID NO:26), nested PCR primer 1 (SEQ ID NO:27), nested PCR primer 2 (SEQ ID NO:28), control primer G3PDH 5' primer (SEQ ID NO:29), and control primer G3PDH 3' primer (SEQ ID NO:30) used for suppression subtractive hybridization for identifying clones 65 and 320. When the adaptors are ligated to RsaI-digested cDNA, the RsaI site is restored.

FIG. 9 shows the cloning site region of the plasmid pGEM-T used to clone all of the clone 65 and 320 sequences herein (SEQ ID NOS:31 and 32 for 5' and 3' sequences, respectively).

FIG. 10 shows the sequence (SEQ ID NO:12) of a clone 65.11 obtained by screening with a probe derived from clone 65, which is the initial clone isolated in the process to obtain full-length mouse clone 65 DNA.

FIG. 11 shows the sequence (SEQ ID NO:13) of a clone 65.9 obtained by screening with a probe derived from clone 65.

FIG. 12 shows the sequence (SEQ ID NO:14) of a clone 65.11.1 obtained by screening with a probe derived from the CDC-42 homologous region of clone 65.11.

FIGS. 13A and 13B show the sequence (SEQ ID NO:15) of a clone 65.11.3 obtained by screening with a probe derived from the CDC-42 homologous region of clone 65.11.

FIG. 14 shows the sequence (SEQ ID NO:16) of a clone 65.11.6 obtained by screening with a probe derived from the CDC-42 homologous region of clone 65.11.

FIG. 15 shows the sequence (SEQ ID NO:17) of clone 65.1 obtained by screening with a probe derived from clone 65.

FIG. 16 shows the sequence (SEQ ID NO:18) of clone 65.6 obtained by screening with a probe derived from clone 65.

FIG. 17 shows the sequence (SEQ ID NO:19) of clone 65.13 obtained by screening with a probe derived from clone 65.

DETAILED DESCRIPTION OF THE PREFERRED EMBODIMENTS

I. Definitions

The terms "clone 65 polypeptide", "clone 65 homologue" and grammatical variants thereof, as used herein, encompass native-sequence protein derived from clone 65 and variants thereof (which are further defined herein). The clone 65 polypeptide may be isolated from a variety of sources, such as from human tissue types or from another source, or prepared by recombinant or synthetic methods, or by any combination of these and similar techniques.

The terms "clone 320 polypeptide", "clone 320 homologue", and grammatical variants thereof, as used herein, encompass native-sequence protein derived from clone 320 and variants thereof (which are further defined herein). The clone 320 polypeptide may be isolated from a variety of sources, such as from human tissue types or from another source, or prepared by recombinant or synthetic methods, or by any combination of these and similar techniques.

A "native-sequence clone 65 polypeptide" comprises a polypeptide having the same amino acid sequence as a clone 65 polypeptide derived from nature. Such native-sequence clone 65 polypeptides can be isolated from nature or can be produced by recombinant or synthetic means. The term "native-sequence clone 65 polypeptide" specifically encompasses naturally-occurring truncated or other forms of a clone 65 polypeptide disclosed herein, naturally-occurring variant forms (e.g., alternatively-spliced forms or splice variants), and naturally-occurring allelic variants of a clone 65 polypeptide. In one embodiment of the invention, the native-sequence clone 65 polypeptide is a full-length, native-sequence human clone 65 polypeptide comprising amino acids 1 to 258 of FIGS. 5A-5D (SEQ ID NO:3), with or without the N-terminal methionine. In another embodiment of the invention, the native-sequence clone 65 polypeptide is a full-length native-sequence mouse clone 65 polypeptide comprising amino acids 1 to 261 of FIGS. 1A and 1B (SEQ ID NO:6), with or without the N-terminal methionine.

In another embodiment of the invention, the native-sequence clone 65 polypeptide is one which is encoded by a nucleotide sequence comprising one of the mouse clone 65 splice or other native-sequence variants, including SEQ ID NOS:11, 12, 13, 14, 15, 16, 17, 18, or 19, with or without an N-terminal methionine.

A "native-sequence clone 320 polypeptide" comprises a polypeptide having the same amino acid sequence as a clone 320 polypeptide derived from nature. Such native-sequence clone 320 polypeptides can be isolated from nature or can be produced by recombinant or synthetic means. The term "native-sequence clone 320 polypeptide" specifically encompasses naturally-occurring truncated or secreted forms of a clone 320 polypeptide disclosed herein, naturally-occurring variant forms (e.g., alternatively spliced forms or splice variants), and naturally-occurring allelic variants of a clone 320 polypeptide. In one embodiment of the invention, the native-sequence clone 320 polypeptide is a mature or full-length, native-sequence mouse clone 320 polypeptide comprising the insert of about 3 kilobases from pRK5E.m.WIG-4.320.9 (deposited with the ATCC as accession no. 209534), with or without any signal sequence, and with or without an N-terminal methionine.

The term "clone 65 variant" means an active clone 65 polypeptide as defined below having at least about 80%, preferably at least about 85%, more preferably at least about 90%, most preferably at least about 95% amino acid sequence identity with human clone 65 having the deduced amino acid sequence shown in FIGS. 5A-5D (SEQ ID NO:3) and/or with mouse clone 65 having the deduced amino acid sequence shown in FIGS. 1A and 1B (SEQ ID NO:6). Such variants include, for instance, clone 65 polypeptides wherein one or more amino acid residues are added to, or deleted from, the N- or C-terminus of the full-length sequences of FIGS. 5A-B and 1A-B (SEQ ID NOS:3 and 6, respectively), including variants from other species, but excludes a native-sequence clone 65 polypeptide.

The term "clone 320 variant" means an active clone 320 polypeptide as defined below having at least about 80%, preferably at least about 85%, more preferably at least about 90%, most preferably at least about 95% amino acid sequence identity with mouse clone 320 derived from the clone deposited with the ATCC under ATCC no. 209534. Such variants include, for instance, clone 320 polypeptides wherein one or more amino acid residues are added to, or deleted from, the N- or C-terminus of the sequence encoding mouse clone 320 contained within the about 3-kb insert of pRK5E.m.WIG-4.320.9 deposited with the ATCC under accession no. 209534, including variants from other species, but excludes a native-sequence clone 320 polypeptide.

"Percent (%) amino acid sequence identity" with respect to the clone 65 and 320 sequences identified herein is defined as the percentage of amino acid residues in a candidate sequence that are identical with the amino acid residues in a clone 65 or 320 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" with respect to the coding region of the clone 65 and 320 sequences identified herein is defined as the percentage of nucleotides in a candidate sequence that are identical with the nucleotides in the coding region of the clone 65 or clone 320 sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN, or Megalign (DNASTAR™) software. Those skilled in the art can determine appropriate parameters for measuring alignment, including any algorithms needed to achieve maximal alignment over the full length of the sequences being compared.

"Stringent conditions" are those that (1) employ low ionic strength and high temperature for washing, for example, 0.015 M sodium chloride/0.0015 M sodium citrate/0.1% sodium dodecyl sulfate at 50° C.; (2) employ during hybridization a denaturing agent, such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC and 0.1% SDS; or (4) employ a buffer of 10% dextran sulfate, 2×SSC (sodium chloride/sodium citrate), and 50% formamide at 55° C., followed by a high-stringency wash consisting of 0.1×SSC containing EDTA at 55° C.

"Moderately stringent conditions" are described in Sambrook et al., *Molecular Cloning: A Laboratory Manual* (New York: Cold Spring Harbor Laboratory Press, 1989), and include the use of a washing solution and hybridization conditions (e.g., temperature, ionic strength, and percent SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc., as necessary to accommodate factors such as probe length and the like.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the natural environment of clone 65 or 320 polypeptide will not be present. Ordinarily, however, isolated polypeptide will be prepared by at least one purification step.

An "isolated" nucleic acid encoding a clone 65 or 320 polypeptide is a nucleic acid molecule that is identified and separated from at least one contaminant nucleic acid molecule with which it is ordinarily associated in the natural source of the respective nucleic acid. An isolated clone 65-encoding or clone 320-encoding nucleic acid molecule is other than in the form or setting in which it is found in nature. An isolated clone 65-encoding or clone 320-encoding nucleic acid molecule therefore is distinguished from the clone 65-encoding or clone 320-encoding nucleic acid molecule as it exists in natural cells. However, an isolated clone 65-encoding or clone 320-encoding nucleic acid molecule includes a nucleic acid molecule contained in cells that ordinarily express clone 65-encoding and clone 320-encoding DNA, where, for example, the nucleic acid molecule is in a chromosomal location different from that of natural cells.

The term "control sequences" refers to DNA sequences necessary for the expression of an operably-linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-clone 65 or anti-clone 320 monoclonal antibodies (including agonist, antagonist, and neutralizing antibodies), and anti-clone 65 or anti-clone 320 antibodies, and antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" or "biological activity", for purposes herein, describes the activity of form(s) of a clone 65 or 320 polypeptide, including its variants, or its antagonists, which retain the biologic and/or immunologic activities of a native or naturally-occurring (native-sequence) clone 65 or 320 polypeptide or its antagonist. Preferred "activities" for a clone 65 or 320 polypeptide or its antagonist include the ability to inhibit proliferation of tumor cells or to stimulate proliferation of normal cells and to treat arteriosclerosis, including atherosclerosis, as well as to induce wound repair and hematopoiesis, prevent desmoplasia, prevent fibrotic lesions associated with skin disorders such as scleroderma, keloid, eosinophilic fasciitis, nodular fasciitis, and Dupuytren's contracture, to treat bone-related diseases such as osteoporosis, to regulate anabolism including promotion of growth, to treat immune disorders, to treat Wilms' tumor and kidney-related disorders, to treat testis-related disorders, to treat lung-related disorders, and to treat cardiac disorders.

An "antagonist" of a clone 65 or 320 polypeptide is a molecule that inhibits an activity of a clone 65 or 320 polypeptide. Preferred antagonists are those which interfere with or block an undesirable biological activity of a clone 65 or 320 polypeptide, such as where a clone 65 or 320 polypeptide might act to stimulate cancer cells and the antagonist would serve to inhibit the growth of those cells. Such molecules include antibodies and small molecules that have such inhibitory capability, as well as polypeptide variants of, and receptors for, a clone 65 or 320 polypeptide (if available) or portions thereof that bind to clone 65 or 320 polypeptide. Thus, the receptor can be expression cloned from the family; then a soluble form of the receptor is made by identifying the extracellular domain and excising the transmembrane domain therefrom. The soluble form of the receptor can then be used as an antagonist, or the receptor can be used to screen for small molecules that would antagonize clone 65 or 320 polypeptide activity.

Alternatively, using the murine nucleotide sequences shown in FIGS. 1-4 (SEQ ID NOS:4, 7, 8, or 9, respectively), or the murine amino acid sequence shown in FIG. 1 (SEQ ID NO:6) or the human nucleotide and amino acid sequences shown in FIGS. 5A-5D (SEQ. ID NOS:1 and 3), variants of native clone 65 or clone 320 are made that act as antagonists.

Antagonist activity can be determined by several means, including standard assays for induction of cell death such as that described herein, e.g., $^3$H-thymidine proliferation assays, or other mitogenic assays, such as an assay measuring the capability of the candidate antagonist of inducing EGF-potentiated anchorage independent growth of target cell lines (Volckaert et al., *Gene*, 15:215-223 (1981)) and/or growth inhibition of neoplastic cell lines. Roberts et al., *Proc. Natl. Acad. Sci. USA,* 82:119-123 (1985). Anchorage-independent growth refers to the ability of clone 65 polypeptide-treated or clone 320 polypeptide-treated, or TGF-β-treated and EGF-treated non-neoplastic target cells to form colonies in soft agar, a characteristic ascribed to transformation of the cells. In this assay, the candidate is incubated together with an equimolar amount of a clone 6.5 or 320 polypeptide otherwise detectable in the EGF-potentiated anchorage-independent target cell growth assay, and the culture observed for failure to induce anchorage-independent growth.

"Treatment" refers to both therapeutic treatment and prophylactic or preventative measures. Those in need of treatment include those already with the disorder or condition as well as those in which the disorder or condition is to be prevented.

"Mammal" for purposes of treatment refers to any animal classified as a mammal, including humans, domestic, and farm animals, and zoo, sports, or pet animals, such as dogs, horses, cats, sheep, pigs, cows, etc. Preferably, the mammal is human.

A "clone 65-related or clone 320-related disorder" is any condition that would benefit from treatment with the clone 65 or 320 polypeptides or clone 65 or 320 antagonists herein. This includes chronic and acute disorders, as well as those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal, and blastocoelic disorders; hematopoiesis-related disorders; tissue-growth disorders; skin disorders; desmoplasia, fibrotic lesions; kidney disorders; bone-related disorders; trauma such as burns, incisions, and other wounds; catabolic states; testicular-related disorders; and inflammatory, angiogenic, and immunologic disorders, including arteriosclerosis. A "Wnt-related disorder" is one caused at least by the upregulation of the Wnt gene pathway, including Wnt-1 and Wnt-4, but preferably Wnt-1, and may include cancer.

The terms "cancer", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. The preferred cancers for treatment herein are breast, colon, lung, and melanoma.

The term "cytotoxic agent" as used herein refers to a substance that inhibits or prevents the function of cells and/or causes destruction of cells. The term is intended to include radioactive isotopes (e.g., $^{131}$I, $^{125}$I, $^{90}$Y, and $^{186}$Re), chemotherapeutic agents, and toxins such as enzymatically active toxins of bacterial, fungal, plant, or animal origin, or fragments thereof.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan, and other related nitrogen mustards. Also included in this definition are hormonal agents that act to regulate or inhibit hormone action on tumors, such as tamoxifen and onapristone.

A "growth-inhibitory agent" when used herein refers to a compound or composition which inhibits growth of a cell, such as an Wnt-overexpressing cancer cell, either in vitro or in vivo. Thus, the growth-inhibitory agent is one which is significantly reduces the percentage of malignant cells in S phase. Examples of growth-inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (W B Saunders: Philadelphia, 1995), especially p. 13. The 4D5 antibody (and functional equivalents thereof) can also be employed for this purpose if the cancer involves ErbB2-overexpressing cancer cells. See, e.g., WO 92/22653.

"Northern analysis" or "Northern blot" is a method used to identify RNA sequences that hybridize to a known probe such as an oligonucleotide, DNA fragment, cDNA or fragment thereof, or RNA fragment. The probe is labeled with a radioisotope such as $^{32}$P, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39-7.52 of Sambrook et al., supra. The technique of "polymerase chain reaction." or "PCR." as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed: these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.*, 51: 263 (1987): Erlich, ed., *PCR Technology*, (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

II. Compositions and Methods of the Invention

A. Full-length Clone 65 or 320 Polypeptide

The present invention provides newly identified and isolated nucleotide sequences encoding a polypeptide referred to in the present application as a clone 65 or clone 320 polypeptide. In particular, cDNAs have been identified and isolated encoding novel murine and human clone 65 polypeptides as well as murine clone 320 as disclosed in further detail in the Examples below.

Using BLAST and FastA sequence alignment computer programs, it was found that the coding sequences of mouse and human clone 65, as well as the three sequences for mouse clone 320 disclosed herein, show significant homology to DNA sequences disclosed in the GenBank database, including those published by Adams et al., *Nature,* 377: 3-174 (1995).

Using BLAST and FastA sequence alignment computer programs, it was found that mouse and human clone 65 show significant homology to members of the Rho family of small GTPases (mouse and human clone 65 are 58-59% and 59% homologous, respectively, to human G25k gtp-binding protein, placental and brain isoforms, and 59% homologous to canine CDC42 GTP-binding protein). Accordingly, it is presently believed that the clone 65 polypeptides disclosed in the present application possess activity relating to the treatment of various cancers with which Ras is associated, as well as to arteriosclerosis, such as atherosclerosis.

B. Clone 65 and 320 Polypeptide Variants

In addition to the full-length native-sequence clone 65 and 320 polypeptides described herein, it is contemplated that variants of these sequences can be prepared. Clone 65 and 320 variants can be prepared by introducing appropriate nucleotide changes into the clone 65-encoding and clone 320-encoding DNA, Or by synthesis of the desired variant clone 65 and 320 polypeptides. Those skilled in the art will appreciate that amino acid changes may alter post-translational processes of the clone 65 and 320 polypeptides, such as changing the number or position of glycosylation sites or altering the membrane-anchoring characteristics, if the native clone 65 or 320 polypeptide is membrane bound.

Variations in the native full-length clone 65 and 320 sequences, or in various domains of the clone 65 and 320 polypeptides described herein, can be made, for example, using any of the techniques and guidelines for conservative and non-conservative mutations set forth, for instance, in U.S. Pat. No. 5,364,934. Variations may be a substitution, deletion, or insertion of one or more codons encoding the clone 65 and 320 polypeptide that results in a change in the amino acid sequence as compared with the native-sequence clone 65 and 320 polypeptide. Optionally the variation is by substitution of at least one amino acid with any other amino acid in any portion of the clone 65 and 320 polypeptide. Guidance in determining which amino acid residue may be inserted, substituted, or deleted without adversely affecting the desired activity may be found by comparing the sequence of the clone 65 and 320 polypeptide with that of homologous known Rac or Rho protein molecules, in the case of clone 65, and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to about 5 amino acids. The variation allowed may be determined by systematically making insertions, deletions, or substitutions of amino acids in the sequence and testing the resulting variants for activity in in vitro assays for gene upregulation or downregulation and in transgenic or knock-out animals.

The variations can be made on the cloned DNA to produce variant DNA using methods known in the art such as oligonucleotide-mediated (site-directed) mutagenesis (Carter et al., *Nucl. Acids Res.,* 13:4331 (1986); Zoller et al., *Nucl. Acids Res.,* 10:6487 (1987)), cassette mutagenesis (Wells et al., *Gene,* 34:315 (1985)), alanine scanning, PCR mutagenesis, restriction selection mutagenesis (Wells et al., *Philos. Trans. R. Soc. London SerA,* 317:415 (1986)), or other known techniques.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions. T. E. Creighton, *Proteins: Structure and Molecular Properties* (W.H. Freeman & Co., San Francisco, 1983); Chothia, *J. Mol. Biol.,* 150:1 (1976). If alanine substitution does not yield adequate amounts of variant, an isoteric amino acid can be used.

Further deletional variants of the full-length clone 65 and 320 polypeptides include variants from which the N-terminal signal peptide, if any, and/or the initiating methionine has been deleted.

C. Modifications of the Clone 65 and 320 Polypeptides

Covalent modifications of the clone 65 and 320 polypeptides are included within the scope of this invention. One type of covalent modification includes reacting targeted amino acid residues of a clone 65 or 320 polypeptide with an organic derivatizing agent that is capable of reacting with selected side chains or the N- or C-terminal residues. Derivatization with bifunctional agents is useful, for instance, for crosslinking a clone 65 or 320 polypeptide to a water-insoluble support matrix or surface for use in the method for purifying anti-clone 65 antibodies and anti-clone 320 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane, and agents such as methyl-3-((p-azidophenyl)-dithio)propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains (Creighton, supra, pp. 79-86), acetylation of the N-terminal amine, and amidation of any C-terminal carboxyl group.

Another type of covalent modification of the clone 65 or 320 polypeptide included within the scope of this invention comprises altering the native glycosylation pattern of the polypeptide. "Altering the native glycosylation pattern" is intended for purposes herein to mean deleting one or more carbohydrate moieties found in the native sequence (either by deleting the underlying glycosylation site or by removing the glycosylation moieties by chemical and/or enzymatic means) and/or adding one or more glycosylation sites that are not present in the native sequence. In addition, the phrase includes qualitative changes in the glycosylation of the native proteins, involving a change in the nature and proportion of the various sugar residues present.

Addition of glycosylation sites to the clone 65 or 320 polypeptide herein may be accomplished by altering the amino acid sequence. The alteration may be made, for example, by the addition of, or substitution by, one or more serine or threonine residues to the native sequence (for O-linked glycosylation sites). The amino acid sequence may optionally be altered through changes at the DNA level, particularly by mutating the DNA encoding the clone 65 or 320 polypeptide at preselected bases such that codons are generated that will translate into the desired amino acids. The DNA mutation(s) may be made using methods described above.

Another means of increasing the number of carbohydrate moieties on the clone 65 or 320 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem., pp.* 259-306 (1981).

Removal of carbohydrate moieties present on the clone 65 or 320 polypeptide may be accomplished chemically or enzymatically or by mutational substitution of codons encoding amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo- and exo-glycosidases as described by Thotakura et al., *Meth. Enzmmol.*, 138:350 (1987).

Another type of covalent modification comprises linking the clone 65 or 320 polypeptide to one of a variety of nonproteinaceous polymers, e.g., polyethylene glycol, polypropylene glycol, or polyoxyalkylenes, in the manner set forth, e.g., in U.S. Pat. Nos. 4,640,835; 4,496,689; 4,301,144; 4,670,417; 4,791,192 or 4,179,337.

The clone 65 or 320 polypeptide of the present invention may also be modified in a way to form a chimeric molecule comprising a clone 65 or 320 polypeptide, or a fragment thereof, fused to a heterologous polypeptide or amino acid sequence. In one embodiment, such a chimeric molecule comprises a fusion of the clone 65 or 320 polypeptide with a tag polypeptide which provides an epitope to which an antitag antibody can selectively bind. The epitope tag is generally placed at the amino- or carboxyl-terminus of a native or variant clone 65 or 320 molecule. The presence of such epitope-tagged forms can be detected using an antibody against the tag polypeptide. Also, provision of the epitope tag enables the clone 65 or 320 polypeptide to be readily purified by affinity purification using an anti-tag antibody or another type of affinity matrix that binds to the epitope tag. In an alternative embodiment, the chimeric molecule may comprise a fusion of the clone 65 or 320 polypeptide, or fragments thereof, with an immunoglobulin or a particular region of an immunoglobulin. For a bivalent form of the chimeric molecule, such a fusion could be to the Fc region of an Ig, such as an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., *Mol. Cell. Biol.*, 8:2159-2165 (1988)); the c-myc tag and the 8F9, 3C7, 6E10, G4, B7, and, 9E10 antibodies thereto (Evan et al., *Molecular and Cellular Biology*, 5:3610-3616 (1985)); and the Herpes Simplex virus glycoprotein D (gD) tag and its antibody. Paborsky et al., *Protein Engineering*, 3(6):547-553 (1990). Other tag polypeptides include the Flag-peptide (Hopp et al., *BioTechnology*, 6:1204-1210 (1988)); the KT3 epitope peptide (Martin et al., *Science*, 255:192-194 (1992)); an α-tubulin epitope peptide (Skinner et al., *J. Biol. Chem.*, 266:15163-15166 (1991)); and the T7 gene 10 protein peptide tag. Lutz-Freyermuth et al., *Proc. Natl. Acad. Sci. USA*, 87:6393-6397 (1990).

D. Preparation of Clone 65 and 320 Polypeptides

The description below relates primarily to production of clone 65 and 320 polypeptides by culturing cells transformed or transfected with a vector containing at least DNA encoding the mature or full-length sequences of human or mouse clone 65 (SEQ ID NOS:3 or 6, respectively), or containing at least mouse clone 320 DNA (deposited at the ATCC as accession no. 209534 and comprising SEQ ID NOS:7, 8, and/or 9).

It is, of course, contemplated that alternative methods, which are well known in the art, may be employed to prepare clone 65 and 320 polypeptides. For instance, the clone 65 or 320 polypeptide sequence, or portions thereof, may be produced by direct peptide synthesis using solid-phase techniques. See, e.g., Stewart et al., *Solid-Phase Peptide Synthesis* (W.H. Freeman Co.: San Francisco, Calif., 1969); Merrifield, *J. Am. Chem. Soc.*, 85:2149-2154 (1963). In vitro protein synthesis may be performed using manual techniques or by automation. Automated synthesis may be accomplished, for instance, using an Applied Biosystems peptide synthesizer (Foster City, Calif.) in accordance with manufacturer's instructions. Various portions of clone 65 and 320 polypeptides may be chemically synthesized separately and combined using chemical or enzymatic methods to produce a full-length clone 65 or 320 polypeptide.

1. Isolation of DNA Encoding Clone 65 and 320 Polypeptides

DNA encoding a clone 65 or 320 polypeptide may be obtained from a cDNA library prepared from tissue believed to possess the mRNA for clone 65 or 320 polypeptide and to express it at a detectable level. Accordingly, DNA encoding human clone 65 or 320 polypeptide can be conveniently obtained from a cDNA library prepared from human tissue, such as a human fetal liver library or as otherwise described in the Examples. The genes encoding clone 65 and 320 polypeptides may also be obtained from a genomic library or by oligonucleotide synthesis.

A still alternative method of cloning clone 65 or 320 polypeptide is suppressive subtractive hybridization, which is a method for generating differentially regulated or tissue-specific cDNA probes and libraries. This is described, for example, in Diatchenko et al. *Proc. Natl. Acad. Sci USA,* 93: 6025-6030 (1996). The procedure is based primarily on a technique called suppression PCR and combines normalization and subtraction in a single procedure. The normalization step equalizes the abundance of cDNAs within the target population and the subtraction step excludes the common sequences between the target and driver populations.

Libraries can be screened with probes (such as antibodies to a clone 65 or 320 polypeptide or oligonucleotides of at least about 20-80 bases) designed to identify the gene of interest or the protein encoded by it. Screening the cDNA or genomic library with the selected probe may be conducted using standard procedures, such as described in Sambrook et al., supra. An alternative means to isolate the gene encoding clone 65 or 320 polypeptide is to use PCR methodology. Sambrook et al., supra; Dieffenbach et al., *PCR Primer: A Laboratory Manual* (New York: Cold Spring Harbor Laboratory Press, 1995).

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation, or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having polypeptide-coding sequence may be obtained by screening selected cDNA or genomic libraries using the deduced amino acid sequences disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for clone 65 or 320 polypeptide production and cultured in conventional nutrient media modified as appropriate for inducing promoters, selecting transformants, or amplifying the genes encoding the desired sequences. The culture conditions, such as media, temperature, pH, and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, *Enterobacteriaceae* such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. Various *E. coli* strains are publicly available, such as *E. coli* K12 strain MM294 (ATCC 31,446); *E. coli* X1776 (ATCC 31,537); *E. coli* strain W3110 (ATCC 27,325); and K5 772 (ATCC 53,635). These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for vectors containing nucleic acid encoding clone 65 or 320 polypeptide. *Saccharomyces cerevisiae* is a commonly used lower eukaryotic host microorganism. However, a number of other genera, species, and strains are commonly available and useful herein, such as *Schizosaccharomyces pombe* (Beach and Nurse, *Nature*, 290: 140 (1981); EP 139,383 published 2 May 1985); *Kluyveromyces* hosts (U.S. Pat. No. 4,943,529; Fleer et al., *Bio/Technology*, 9: 968-975 (1991)) such as, e.g., *K. lactis* (MW98-8C, CBS683, CBS4574; Louvencourt et al., *J. Bacteriol.*, 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8: 135 (1990)), *K. thermotolerans*, and *K. marxianus*; *yarrowia* (EP 402,226); *Pichia pastoris* (EP 183,070; Sreekrishna et al., *J. Basic Microbiol.*, 28: 265-278 (1988)); *Candida*; *Trichoderma reesia* (EP 244,234); *Neurospora crassa* (Case et al., *Proc. Natl. Acad. Sci. USA*, 76: 5259-5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 0.91/00357 published 10 Jan. 1991), and *Aspergillus* hosts such as *A. nidulans* (Ballance et al., *Biochem. Biophys. Res. Commun.*, 112: 284-289 (1983); Tilburn et al., *Gene*, 26: 205-221 (1983); Yelton et al., *Proc. Natl. Acad. Sci. USA*, 81: 1470-1474 (1984)) and *A. niger* Kelly and Hynes, *EMBO J.*, 4: 475-479 (1985). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, *The Biochemistry of Methylotrophs*, 269 (1982).

Suitable host cells for the expression of glycosylated clone 65 or 320 polypeptide are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture (Graham et al., *J. Gen Virol.*, 36:59 (1977)); Chinese hamster ovary cells/-DHFR(CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding the desired clone 65 or 320 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The desired clone 65 or 320 polypeptide may be produced recombinantly not only directly, but also as a fusion polypeptide with a heterologous polypeptide, which may be a signal sequence, if the clone 65 or 320 polypeptide is conducive to being secreted, or other polypeptide having a specific cleavage site at the N-terminus of the mature or full-length protein or polypeptide. In general, the signal sequence may be a component of the vector, or it may be a part of the DNA encoding the clone 65 or 320 polypeptide that is inserted into the vector. The signal sequence may be a prokaryotic signal sequence such as, for example, the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders, and including signals from clone 65 or 320 polypeptide.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the nucleic acid encoding clone 65 or 320 polypeptide, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7. Stinchcomb et al., *Nature*, 282:39 (1979); Kingsman et al., *Gene*, 7:141 (1979); Tschemper et al., *Gene*, 10:157 (1980). The trp1 gene provides a selection marker for a mutant strain of yeast lacking the ability to grow in tryptophan, for example, ATCC No. 44076 or PEP4-1. Jones, *Genetics*, 85:12 (1977).

Expression and cloning vectors usually contain a promoter operably linked to the nucleic acid sequence encoding clone 65 or 320 polypeptide to direct mRNA synthesis. Promoters recognized by a variety of potential host cells are well known. Promoters suitable for use with prokaryotic hosts include the β-lactamase and lactose promoter systems (Chang et al., *Nature*, 275:615 (1978); Goeddel et al., *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter. deBoer et al., *Proc. Natl. Acad. Sci. USA*, 80:21-25 (1983). Promoters for use in bacterial systems also will contain a Shine-Dalgarno (S.D.) sequence operably linked to the DNA encoding the clone 65 or 320 polypeptide.

Examples of suitable promoting sequences for use with yeast hosts include the promoters for 3-phosphoglycerate kinase (Hitzeman et al., *J. Biol. Chem.*, 255:2073 (1980)) or other glycolytic enzymes (Hess et al., *J. Adv. Enzyme Req.*, 7:149 (1968); Holland, *Biochemistry*, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Clone 65 or 320 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus, and Simian Virus 40 (SV40); from heterologous mammalian promoters, e.g., the actin promoter or an immunoglobulin promoter; and from heat-shock promoters, provided such promoters are compatible with the host cell systems.

Transcription of a DNA encoding a clone 65 or 320 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the sequence coding for a clone 65 or 320 polypeptide, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding clone 65 or 320 polypeptide.

Still other methods, vectors, and host cells suitable for adaptation to the synthesis of clone 65 and 320 polypeptides in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native-sequence clone 65 or 320 polypeptide or against a synthetic peptide based on the DNA sequences provided herein or against exogenous sequence fused to DNA encoding clone 65 or 320 polypeptide and encoding a specific antibody epitope.

5. Purification of Polypeptide

Forms of clone 65 or 320 polypeptide may be recovered from culture medium or from host cell lysates. If membrane-bound, it can be released from the membrane using a suitable detergent solution (e.g., Triton-X 100) or by enzymatic cleavage. Cells employed in expression of clone 65 and 320 polypeptides can be disrupted by various physical or chemical means, such as freeze-thaw cycling, sonication, mechanical disruption, or cell lysing agents.

It may be desired to purify clone 65 or 320 polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX™ G-75; protein A SEPHAROSE™ columns to remove contaminants such as IgG; and metal chelating columns to bind epitope-tagged forms of the clone 65 or 320 polypeptide. Various methods of protein purification may be employed, and such methods are known in the art and described, for example, in Deutscher, *Methods in Enzymology,* 182 (1990); and Scopes, *Protein Purification: Principles and Practice* (Springer-Verlag: New York, 1982).

In one specific example of purification, either a poly-HIS tag or the Fc portion of human IgG is added to the C-terminal coding region of the cDNA for clone 65 or clone 320 before expression. The conditioned media from the transfected cells are harvested by centrifugation to remove the cells and filtered. For the poly-HIS tagged constructs, the protein may be purified using a Ni-NTA column. After loading, the column may be washed with additional equilibration buffer and the protein eluted with equilibration buffer containing 0.25 M imidazole. The highly purified protein may then be desalted into a storage buffer if desired.

Immunoadhesin (Fc-containing) constructs of the clone 65 or clone 320 polypeptides may be purified from the conditioned media by pumping them onto a 5-ml Protein A column that had been equilibrated in a phosphate buffer. After loading, the column may be washed extensively with equilibration buffer before elution with citric acid. The eluted protein may be immediately neutralized by collecting 1-ml fractions into tubes containing TRIS buffer. The highly purified protein may be subsequently desalted into storage buffer as described above for the poly-HIS tagged proteins. The homogeneity of the protein may be assessed by SDS polyacrylamide gels and by N-terminal amino acid sequencing by Edman degradation.

The purification step(s) selected will depend, for example, on the nature of the production process used and the particular clone 65 or 320 polypeptide produced.

E. Uses for Clone 65 and 320 Polypeptides and Their Nucleic Acid

Nucleotide sequences (or their complement) encoding clone 65 and 320 polypeptides have various applications in the art of molecular biology, including uses as hybridization probes, in chromosome and gene mapping, and in the generation of anti-sense RNA and DNA. Nucleic acid encoding clone 65 or 320 polypeptide will also be useful for the preparation of clone 65 or 320 polypeptide by the recombinant techniques described herein.

The full-length nucleotide sequences for mouse or human clone 65 (SEQ ID NOS:4 and 1, respectively), or portions thereof, or the sequences in FIGS. 2, 3, and 4 for mouse clone 320 (SEQ ID NOS:7, 8, and/or 9), or portions thereof, may be used as hybridization probes for a cDNA library to isolate or detect the full-length gene encoding the clone 65 or 320 polypeptide of interest or to isolate or detect still other genes (for instance, those encoding naturally occurring variants of clone 65 or 320 polypeptide, other clone 65 or 320 polypeptide family members, or clone 65 or 320 polypeptides from other species) which have a desired sequence identity to the clone 65 polypeptide sequences disclosed in FIGS. 1 and 5 (SEQ ID NOS:6 and 3, respectively). For example, such procedures as in situ hybridization, Northern and Southern blotting, and PCR analysis may be used to determine whether DNA and/or RNA encoding a different clone 65 or 320 polypeptide is present in the cell type(s) being evaluated. Optionally, the length of the probes will be about 20 to about 50 bases. For example, the hybridization probes may be derived from ESTS, cloned sequences, or genomic sequences including promoters, enhancer elements, and introns of DNA encoding native-sequence clone 65 or 320 polypeptide.

By way of example, a screening method will comprise isolating the coding region of the clone 65 or clone 320 gene using the known DNA sequence to synthesize a selected probe of about 40 bases. Hybridization probes may be labeled by a variety of labels, including radionucleotides such as $^{32}P$ or $^{35}$S, or enzymatic labels such as alkaline phosphatase coupled to the probe via avidin/biotin coupling systems. Labeled probes having a sequence complementary to that of any of the genes encoding clone 65 or 320 polypeptide of the present invention can be used to screen libraries of human cDNA, genomic DNA, or mRNA to determine to which members of such libraries the probe hybridizes. Hybridization techniques are described in further detail in the Examples below.

The probes may also be employed in PCR techniques to generate a pool of sequences for identification of closely-related clone 65 and 320 sequences.

Nucleotide sequences encoding a clone 65 or 320 polypeptide can also be used to construct hybridization probes for mapping the gene that encodes the particular clone 65 or 320 polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acid encoding a clone 65 or 320 polypeptide may be used as a diagnostic to determine the extent and rate of the expression of the DNA encoding a clone 65 or 320 polypeptide in the cells of a patient. To accomplish such an assay, a sample of a patient's cells is treated, via in situ hybridization, or by other suitable means, and analyzed to determine whether the sample contains mRNA molecules capable of hybridizing with the nucleic acid molecule.

Nucleic acids that encode clone 65 or 320 polypeptide or any of their modified forms can also be used to generate either transgenic animals or "knock-out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA that is integrated into the genome of a cell from which a transgenic animal develops. In one embodiment, cDNA encoding a clone 65 or 320 polypeptide can be used to clone genomic DNA encoding the clone 65 or 320 polypeptide in accordance with established techniques and the genomic sequences used to generate transgenic animals that contain cells which express DNA encoding the clone 65 or 320 polypeptide.

Methods for generating transgenic animals, particularly animals such as mice or rats, have become conventional in the art and are described, for example, in U.S. Pat. Nos. 4,736,866 and 4,870,009 and WO 97/38086. Typically, particular cells would be targeted for clone 65 or 320 transgene incorporation with tissue-specific enhancers. Transgenic animals that include a copy of a transgene encoding the clone 65 or 320 polypeptide introduced into the germ line of the animal at an embryonic stage can be used to examine the effect of increased expression of DNA encoding the clone 65 or 320 polypeptide. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of clone 65 and 320 polypeptides can be used to construct a clone 65 or 320 polypeptide "knock-out" animal which has a defective or altered gene encoding a clone 65 or 320 polypeptide as a result of homologous recombination between the endogenous gene encoding the clone 65 or 320 polypeptide and altered genomic DNA encoding the clone 65 or 320 polypeptide introduced into an embryonic cell of the animal. For example, cDNA encoding the clone 65 or 320 polypeptide can be used to clone genomic DNA encoding the clone 65 or 320 polypeptide in accordance with established techniques. A portion of the genomic DNA encoding the clone 65 or 320 polypeptide can be deleted or replaced with another gene, such as a gene encoding a selectable marker which can be used to monitor integration. Typically, several kilobases of unaltered flanking DNA (both at the 5' and 3' ends) are included in the vector. See e.g., Thomas and Capecchi, *Cell*, 51:503 (1987) for a description of homologous recombination vectors. The vector is introduced into an embryonic stem cell line (e.g., by electroporation) and cells in which the introduced DNA has homologously recombined with the endogenous DNA are selected. See e.g., Li et al., *Cell*, 69:915 (1992). The selected cells are then injected into a blastocyst of an animal (e.g., a mouse or rat) to form aggregation chimeras. See e.g., Bradley, in *Teratocarcinomas and Embryonic Stem Cells: A Practical Approach*, E. J. Robertson, ed. (IRL, Oxford, 1987), pp. 113-152. A chimeric embryo can then be implanted into a suitable pseudopregnant female foster animal and the embryo brought to term to create a "knock-out" animal. Progeny harboring the homologously recombined DNA in their germ cells can be identified by standard techniques and used to breed animals in which all cells of the animal contain the homologously recombined DNA. Knock-out animals can be characterized, for instance, by their ability to defend against certain pathological conditions and by their development of pathological conditions due to absence of the clone 65 or 320 polypeptide.

In particular, assays in which the Rac and Rho family members are usually used are preferably performed with the clone 65 polypeptide. Further, an assay to determine whether TGF-β induces the clone 65 or 320 polypeptide, indicating a role in cancer, may be performed as known in the art, as well as assays involving induction of cell death and $^3$H-thymidine proliferation assays. Mitogenic and tissue growth assays are also performed with the clone 65 or 320 polypeptide as set forth above. The results are applied accordingly.

The clone 65 or 320 polypeptides of the present invention may also be used to induce the formation of anti-clone 65 or anti-clone 320 polypeptide antibodies which are identified by routine screening as detailed below.

For diagnostic purposes, the clone 65 or clone 320 polypeptide can be used in accordance with immunoassay technology. Examples of immunoassays are provided by Wide at pages 199-206 of *Radioimmune Assay Method*, Kirkham and Huner, ed. E & S. Livingstone, Edinburgh. 1970.

Thus, in one embodiment, clone 65 or clone 320 polypeptides can be detectably labeled and incubated with a test sample containing the molecules of interest (such as biological fluids, e.g., serum, sputum, urine, etc.), and the amount of clone 65 or clone 320 molecule bound to the sample ascertained.

Immobilization of reagents is required for certain assay methods. Immobilization entails separating the clone 65 or clone 320 polypeptide from any analyte that remains free in solution. This conventionally is accomplished by either insolubilizing the clone 65 or clone 320 polypeptide before the assay procedure, as by adsorption to a water-insoluble matrix or surface (Bennich et al., U.S. Pat. No. 3,720,760), by covalent coupling (for example, using glutaraldehyde crosslinking), or by insolubilizing the molecule afterward, e.g. by immunoprecipitation.

The foregoing are merely exemplary diagnostic assays. Other methods now or hereafter developed for the determination of these analytes are included within the scope hereof.

In addition, clone 65 and 320 polypeptides are useful for screening for compounds that bind to them as defined above. Preferably, these compounds are small molecules such as organic or peptide molecules that exhibit one or more of the desired activities. Screening assays of this kind are conventional in the art, and any such screening procedure may be employed, whereby the test sample is contacted with the clone 65 or 320 polypeptide herein and the extent of binding and biological activity of the bound molecule are determined.

Clone 65 and clone 320 polypeptides are additionally useful in affinity purification of a molecule that binds to clone 65 or clone 320 polypeptide and in purifying antibodies thereto. The clone 65 or clone 320 polypeptide is typically coupled to an immobilized resin such as Affi-Gel 10™ (Bio-Rad, Richmond, Calif.) or other such resins (support matrices) by means well known in the art. The resin is equilibrated in a buffer (such as one containing 150 mM NaCl, 20 mM HEPES, pH 7.4 supplemented to contain 20% glycerol and 0.5% NP-40) and the preparation to be purified is placed in contact with the resin, whereby the molecules are selectively adsorbed to the clone 65 or clone 320 polypeptide on the resin.

The resin is then sequentially washed with suitable buffers to remove non-adsorbed is material, including unwanted contaminants, from the mixture to be purified, using, e.g., 150 mM NaCl. 20 mM HEPES, pH 7.4, containing 0.5% NP-40; 150 mM NaCl, 20 mM HEPES, pH 7.4 containing 0.5 M NaCl and 0.1% NP-40: 150 mM NaCl. 20 mM HEPES, pH 7.4 containing 0.1% deoxycholate: 150 mM NaCl, 20 mM HEPES, pH 7.4 containing 0.1% NP-40; and a solution of 0.1% NP-40, 20% glycerol and 50 mM glycine, pH 3. The resin is then treated so as to elute the binding molecule using a buffer that will break the bond between the binding molecule and clone 65 or clone 320 polypeptide (using, e.g., 50 mM glycine, pH 3, 0.1% NP-40, 20% glycerol, and 100 mM NaCl).

It is contemplated that the clone 65 and 320 polypeptides of the present invention may be used to treat various conditions, including those characterized by overexpression and/or activation of at least the Wnt pathway. Further, they are useful in diagnosing cancer, for example, as a marker for increased susceptibility to cancer or for having cancer. Exemplary conditions or disorders to be treated with the clone 65 and 320 polypeptides include benign or malignant tumors (e.g., renal, liver, kidney, bladder, testicular, breast, gastric, ovarian, colorectal, prostate, pancreatic, lung, esophageal, vulval, thyroid, hepatic carcinomas; sarcomas; glioblastomas; and various head and neck tumors); leukemias and lymphoid malignancies; other disorders such as neuronal, glial, astrocytal, hypothalamic, and other glandular, macrophagal, epithelial, stromal, and blastocoelic disorders; cardiac disorders; renal disorders; catabolic disorders; bone-related disorders such as osteoporosis; and inflammatory, angiogenic, and immunologic disorders, such as arteriosclerosis.

The clone 65 and 320 polypeptides of the invention are administered to a mammal, preferably a human, in accord with known methods, such as intravenous administration as a bolus or by continuous infusion over a period of time, by intramuscular, intraperitoneal, intracerebrospinal, subcutaneous, intra-articular, intrasynovial, intrathecal, oral, topical, or inhalation routes. Intravenous or subcutaneous administration of the polypeptide is preferred.

Therapeutic formulations of the clone 65 or 320 polypeptide are prepared for storage by mixing the polypeptide having the desired degree of purity with optional pharmaceutically acceptable carriers, excipients, or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose, or sorbitol; salt-forming counter-ions such as sodium; metal complexes (e.g., Zn-protein complexes); and/or non-ionic surfactants such as TWEEN™, PLURONICS™, or polyethylene glycol (PEG).

Other therapeutic regimens may be combined with the administration of the clone 65 and 320 polypeptides of the instant invention. For example, the patient to be treated with the polypeptides disclosed herein may also receive radiation therapy if the disorder is cancer. Alternatively, or in addition, a chemotherapeutic agent may be administered to the patient with cancer. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry (Williams & Wilkins: Baltimore, Md., 1992). The chemotherapeutic agent may precede or follow administration of the polypeptide or may be given simultaneously therewith. The polypeptide may be combined with an anti-oestrogen compound such as tamoxifen or an anti-progesterone such as onapristone (see, EP 616812) in dosages known for such molecules.

It may be desirable also to co-administer with the clone 65 or 320 polypeptide (or anti-clone 65 or anti-clone 320 polypeptide antibodies) antibodies against other tumor-associated antigens, such as antibodies which bind to HER-2, EGFR, ErbB2, ErbB3, ErbB4, or vascular endothelial factor (VEGF). Alternatively, or in addition, two or more different anti-cancer antibodies, such as anti-ErbB2 antibodies, may be co-administered to the patient with the clone 65 or 320 polypeptide (or anti-clone 65 or anti-clone 320 polypeptide antibodies). Sometimes, it may be beneficial also to administer one or more cytokines to the patient.

In a preferred embodiment, the clone 65 or clone 320 polypeptide is co-administered with a growth-inhibitory agent to the cancer patient. For example, the growth-inhibitory agent may be administered first, followed by the clone 65 or 320 polypeptide. However, simultaneous administration or administration of the clone 65 or clone 320 polypeptide first is also contemplated. Suitable dosages for the growth-inhibitory agent are those presently used and may be lowered due to the combined action (synergy) of the growth-inhibitory agent and polypeptide. The antibodies, cytotoxic agents, cytokines, or growth-inhibitory agents are suitably present in combination in amounts that are effective for the purpose intended.

The active ingredients may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences,* 16th edition, Osol, A. Ed. (1980)., supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels (for example, poly(2-hydroxyethylmethacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For the prevention or treatment of disease or disorder, the appropriate dosage of clone 65 or 320 polypeptide will depend on the type of disorder to be treated, as defined above, the severity and course of the disorder, whether the polypeptide is administered for preventive or therapeutic purposes, previous therapy, the patient's clinical history and response to the polypeptide, the route of administration, the condition of the patient, and the discretion of the attending physician. The polypeptide is suitably administered to the patient at one time or over a series of treatments.

Depending on the type and severity of the disease, about 1 μg/kg to 15 mg/kg (e.g., 0.1-20 mg/kg) of clone 65 or 320 polypeptide is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of symptoms of the disorder occurs. However, other dosage regimens may be useful. The progress of this therapy is easily monitored by conventional techniques and assays.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example, the container may be an intravenous solution bag or a vial having a stopper pierceable by a hypodermic injection needle). The active agent in the composition is the clone 65 or 320 polypeptide. The label on, or associated with, the container indicates that the composition is used for treating the condition or disorder of choice. The article of manufacture may further comprise a second container comprising a pharmaceutically acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

F. Anti-Clone 65 and 320 Polypeptide Antibodies

The present invention further provides anti-clone 65 and 320 polypeptide antibodies. Exemplary antibodies include polyclonal, monoclonal, humanized, bispecific, and heteroconjugate antibodies.

1. Polyclonal Antibodies

The anti-clone 65 and 320 polypeptide antibodies of the present invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the clone 65 or 320 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-clone 65 or 320 polypeptide antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the clone 65 or 320 polypeptide or a fusion protein thereof. Generally, either peripheral blood lymphocytes ("PBLs") are used if, cells of human origin are desired, or spleen cells or lymph node cells are used if non-human mammalian sources are desired. The lymphocytes are then fused with an immortalized cell line using a suitable fusing agent, such as PEG, to form a hybridoma cell. Goding, *Monoclonal Antibodies: Principles and Practice* (Academic Press: New York, 1986) pp. 59-103. Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif., and the American Type Culture Collection, Manassas, Va. Human myeloma and mouse-human heteromyeloma cell lines also have been described for the production of human monoclonal antibodies. Kozbor, *J. Immunol.*, 133:3001 (1984); Brodeur et al., *Monoclonal Antibody Production Techniques and Applications* (Marcel Dekker, Inc.: New York, 1987) pp. 51-63.

The culture medium in which the hybridoma cells are cultured can then be assayed for the presence of monoclonal antibodies directed against a clone 65 or 320 polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, CHO cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., *Proc. Natl. Acad. Sci. USA*, 81: 6851-6855 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using routine techniques known in the art.

3. Humanized Antibodies

The anti-clone 65 and anti-clone 320 polypeptide antibodies of the invention may further comprise humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. Humanized antibodies include human immunoglobulins (recipient antibody) in which residues from a is complementary-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies may also comprise residues which are found neither in the recipient antibody nor in the imported CDR or framework sequences.

In general, the humanized antibody will comprise substantially all of at least one, and typically two, variable domains, in which all or substantially all of the CDR regions correspond to those of a non-human immunoglobulin, and all or substantially all of the FR regions-are those of a human immunoglobulin consensus sequence. The humanized antibody preferably also will comprise at least a portion of an immunoglobulin constant region (Fc), typically that of a human immunoglobulin. Jones et al., *Nature*, 321:522-525 (1986); Riechmann et al., *Nature*, 332:323-329 (1988); Presta, *Curr. Op. Struct. Biol.*, 2:593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art., including phage display libraries.

Hoogenboom and Winter, *J. Mol. Biol.*, 227:381 (1991); Marks et al., *J. Mol. Biol.*, 222:581 (1991). The techniques of Cole et al. and Boerner et al. are also available for the preparation of human monoclonal antibodies. Cole et al., *Monoclonal Antibodies and Cancer Therapy*, Alan R. Liss, p. 77 (1985); Boerner et al., *J. Immunol.*, 147(1):86-95 (1991).

4. Bispecific Antibodies

Bispecific antibodies are monoclonal, preferably human or humanized, antibodies that have binding specificities for at least two different antigens. In the present case, one of the binding specificities is for a clone 65 or 320 polypeptide; the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities. Milstein and Cuello, *Nature*, 305:537-539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.*, 10:3655-3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection. WO 91/00360; WO 92/200373; EP 03089. It is contemplated that the antibodies may be prepared in vitro using known methods in synthetic protein chemistry, including those involving cross-linking agents. For example, immunotoxins may be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for Anti-Clone 65 and Anti-Clone 320 Polypeptide Antibodies

The antibodies of the invention may be used as affinity purification agents. In this process, the antibodies are immobilized on a solid phase such a SEPHADEX™ resin or filter paper, using methods well known in the art. The immobilized antibody is contacted with a sample containing the clone 65 or 320 polypeptide (or fragment thereof) to be purified, and thereafter the support is washed with a suitable solvent that will remove substantially all the material in the sample except the clone 65 or 320 polypeptide, which is bound to the immobilized antibody. Finally, the support is washed with another suitable solvent, such as glycine buffer, pH 5.0, that will release the clone 65 or 320 polypeptide from the antibody.

Anti-clone 65 or 320 polypeptide antibodies may also be useful in diagnostic assays for clone 65 or 320 polypeptide, e.g., detecting its expression in specific cells, tissues, or serum. Thus, the antibodies may be used in the diagnosis of human malignancies (see, for example, U.S. Pat. No. 5,183,884).

For diagnostic applications, the antibody typically will be labeled with a detectable moiety. Numerous labels are available which can be preferably grouped into the following categories:

(a) Radioisotopes, such as $^{32}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed., (Wiley-Interscience: New York, 1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin, and Texas Red are available. The fluorescent labels can be conjugated to the antibody using the techniques disclosed in *Current Protocols in Immunology*, supra, Coligen, ed., for example. Fluorescence can be quantified using a fluorimeter.

(c) Various enzyme-substrate labels are available, and U.S. Pat. No. 4,275,149 provides a review of some of these. The enzyme preferably catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., *Methods for the Preparation of Enzyme-Antibody Conjugates for use in Enzyme Immunoassay, in Methods in Enzym.*, Vol. 73, Langone and Van Vunakis, eds. (New York: Academic Press, 1981), pp. 147-166.

Examples of enzyme-substrate combinations include:

(I) Horseradish peroxidase (HRPO) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (4-methylumbelliferyl-β-D-galactosidase).

Numerous other enzyme-substrate combinations are available to those skilled in the art. For a general review of these, see, for example, U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin, and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-clone 65 or 320 polypeptide antibody need not be labeled, and the presence thereof can be detected using a labeled antibody that binds to the anti-clone 65 or 320 polypeptide antibody.

The antibodies of the present invention may be employed in any known assay method, such as competitive binding assays, direct and indirect sandwich assays, and immunoprecipitation assays. Zola, *Monoclonal Antibodies: A Manual of Techniques* (New York: CRC Press, Inc., 1987), pp. 147-158.

Competitive binding assays rely on the ability of a labeled standard to compete with the test sample analyte for binding with a limited amount of antibody. The amount of clone 65 or 320 polypeptide in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Preferably, the antibody is labeled with a radionuclide (such as $^{111}$In, $^{99}$Tc, $^{14}$C, $^{131}$I, $^{125}$I, $^{3}$H, $^{32}$P or $^{35}$S) so that the tumor can be localized using immunoscintiography.

Additionally, anti-clone 65 or 320 polypeptide antibodies may be useful as antagonists to clone 65 or 320 polypeptide functions where clone 65 or 320 polypeptide is upregulated in cancer cells or stimulates their proliferation or is upregulated in atherosclerotic tissue. Hence, for example, the anti-clone 65 and 320 polypeptide antibodies may by themselves or with a chemotherapeutic agent or other cancer treatment or drug such as anti-HER-2 antibodies be effective in treating certain forms of cancer such as breast cancer, colon cancer, lung cancer, and melanoma. Further uses for the antibodies include inhibiting the binding of a clone 65 or 320 polypeptide to its receptor, if applicable, or to a protein that binds to the clone 65 or 320 polypeptide, if applicable. For therapeutic use, the antibodies can be used in the formulations, schedules, routes, and doses indicated above under uses for the clone 65 and 320 polypeptides. In addition, anti-clone 65 and 320 polypeptide antibodies may be administered into the lymph as well as the blood stream.

As a matter of convenience, the anti-clone 65 or 320 polypeptide antibody of the present invention can be provided in a kit format, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer), and the like. The relative amounts of the various reagents may be varied to provide for concentrations in solution of the reagents which substantially maximize the sensitivity of the assay. Particularly, the reagents may be provided as dry powders, usually lyophilized, including excipients which on dissolution will provide a reagent solution having the appropriate concentration.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, 10801 University Blvd., Manassas, Va.

Example 1

Isolation of cDNA Clones Encoding Mouse Clone 65

Several putative genes encoding clone 65 and 320 polypeptides have been identified at the mRNA level in a high throughput PCR-select cDNA substraction experiment carried out using a mouse mammary cell line (C57MG), which has been transformed by a Wnt-1 retroviral vector and compared with the parental cell line. The clone 65 and 320 polypeptide family disclosed herein, including the mouse clone 65 gene, was induced only in the transformed cell line C57MGWnt-1.

1. Suppression Subtractive Hybridization

Mouse clone 65 was isolated independently by Wnt-1 differential screening using suppression subtractive hybridization (SSH), as described by Diatchenko et al., *Proc. Natl. Acad. Sci. USA*, 93: 6025-6030 (1996). SSH was carried out using the PCR-SELECT® cDNA Subtraction Kit (Clontech Laboratories, Inc.) according to the manufacturer's protocol. Driver double-stranded (ds) cPNA was synthesized from 2 micrograms of polyA+ RNA isolated from a mouse mammary cell line (C57MG), obtainable from a mouse breast cancer myoepithelial cell line. This cell line is described in Brown et al., *Cell,* 46: 1001-1009 (1986); Olson and Papkoff, *Cell Growth and Differentiation,* 5: 197-206 (1994); Wong et al., *Mol. Cell. Biol.,* 14: 6278-6286 (1994); and Jue et al., *Mol. Cell. Biol.,* 12: 321-328 (1992), and is responsive to Wnt-1 but not to Wnt-4. Tester ds cDNA was synthesized from 2 micrograms of polyA+ RNA isolated from a transformed version of C57MG, called C57MG/wnt-1.

The C57MG/wnt-1 mouse mammary derivative cell line was prepared by first transforming the parent line with a Wnt-1 retroviral vector, pBabe Puro (5.1 kb). This vector has a 5' LTR, packaging elements, a multiple cloning site, the puromycin-resistance gene driven off the SV40 promoter, a 3' LTR, and the bacterial elements for replication and ampicillin selection. The vector was modified slightly for Wnt-1 cloning by removing the HindIII site after the SV40 promoter and adding a HindIII site to the multiple cloning site. Wnt-1 is cloned from EcoRI-HindIII in the multiple cloning site. FIG. 7 shows a map of the vector.

The transformed derivative cells were grown up in a conventional fashion, and the final cell population was selected in DMEM+10% FCS with 2.5 µg/ml puromycin to stabilize the expression vector.

PCR was performed using the Clontech kit, including the cDNA synthesis primer (SEQ ID NO:20), adaptors 1 and 2 (SEQ ID NOS:21 and 22, respectively) and complementary sequences for the adaptors (SEQ ID NOS:23 and 24, respectively), PCR primer 1 (SEQ ID NO:25), PCR primer 2 (SEQ ID NO:26), nested PCR primer 1 (SEQ ID NO:27), nested PCR primer 2 (SEQ ID NO:28), control primer G3PDH5' primer (SEQ ID NO:29), and control primer G3PDH3' primer (SEQ ID NO:30), shown in FIG. 8.

Products generated from the secondary PCR reaction were inserted into the cloning site region of pGEM-T vector (Promega), shown in FIG. 9 (SEQ ID NOS:31 and 32 for 5' and 3' sequences, respectively). Plasmid DNAs were prepared using the Wizard Miniprep Kit™ (Promega). DNA sequencing of the subcloned PCR fragments was performed manually by the chain termination reaction (Sequenase 2.0™ Kit, Pharmacia). Nucleic acid homology searches were performed using the BLAST program noted above.

A total of 1384 clones were sequenced out of greater than 5000 found. A total of 1996 DNA templates were prepared. A program was used to trim the vector off, and a different program used to cluster the clones into two or more identical clones or with an overlap of 50 bases the same. Then a BLAST was performed of a representative clone from the cluster. Primers were designed for RT-PCR to see if the clones were differentially expressed.

2. Semi-quantitative RT-PCR

The initial clone isolated, designated clone 65, had 212 bp and the sequence:

For the RT-PCR procedure, cell lines were grown to subconfluence before extracting the RNA. Total RNA was extracted using Stat-60™ (Tel-TestT™ B) per manufacturer's instructions. First-strand cDNA was prepared from 0.1 µg-3 µg of total RNA with the Superscript™ RT kit (Gibco, BRL). PCR amplification of 5 µl of first-strand cDNA was performed in a 50-µl PCR reaction. The above primers were used to amplify first-strand cDNA. As controls, primers corresponding to nucleotide positions 707-729 (sense; 5'-GTG-GCCCATGCTCTGGCAGAGGG (SEQ ID NO:35)) or 836-859 (sense; 5'-GACTGGAGCAAGGTCGTCCTCGCC (SEQ ID NO:36)) and 1048-1071 (anti-sense; 5'-GCAC-CACCCACAAGGAAGCCATCC (SEQ ID NO:37)) of human triosephosphate isomerase (huTPI) (Maquat et al., *J. Biol. Chem.*, 260: 3748-3753 (1985); Brown et al., *Mol. Cell. Biol.*, 5: 1694-1706 (1985)) were used to amplify first-strand cDNA. For mouse triosephosphate isomerase, primers corresponding to nucleotide positions 433-456 (sense; 5'1-GAC-GAAAGGGAAGCCGGCATCACC (SEQ ID NO: 38)) or 457-480 bp (sense; 5'-GAGAAGGTCGTGTTCGAG-CAAACC (SEQ ID NO: 39)) and 577-600 bp (antisense; 5'-CTTCTCGTGTACTTCCTGTGCCTG (SEQ ID NO:40)) or 694-717 bp (antisense; 5'-CACGTCAGCTGGCGTTGC-CAGCTC (SEQ ID NO:41)) were used for amplification.

Briefly, 4 µCi of (–$^{32}$P)CTP (3000 Ci/mmol) was added to each reaction with 2.5 U of TaKaRa Ex Taq™ (Panvera, Madison, Wis.) and 0.2 µM of each dNTP. The reactions were amplified in a 480 PCR thermocycler™ (Perkin Elmer) using the following conditions: 94° C. for 1 min., 62° C. for 30 sec., 72° C. for 1 min, for 18-25 cycles. 5 µl of PCR products were electrophoresed on a 6% polyacrylamide gel. The gel was exposed to film. Densitometry measurements were obtained using Alpha Ease Version 3.3a™ software (Alpha Innotech Corporation) to quantitate the clone 65-specific and clone 320-specific or TPI-specific gene products.

3. Northern Blot Analysis

Adult multiple-tissue Northern blots (Clontech) and the Northern blot of the C57MG parent and C57MG/Wnt-1 derivative polyA+ RNA (2 µg/lane) were hybridized with a probe designated 65.50mer.2 of nucleotide bases 261-310 of FIGS. 1A and 1B:
5'-CAACTTCTCGGCCGTGGTGTCTGTA-GATGGGCGGCCTGTGAGACTCCAGC (SEQ ID NO:42) generated using the primers noted above. The membranes were washed in 0.1×SSC at 55-65° C. and

```
5' CAGAGGGTGGGTGGGAAAGAGTGAATTATTTAATTTTAAATGTTATAATAAAGCCAATGT   (SEQ ID NO:11)

AGTTGAGACCAAGGAAATGAGCATTGAGAACACAAACTTGAAGTCTGGTGCCAGGGTTGT

TGGACCTCACACCCTGTCTCTGAGCCACCCGGAAGTGACATAAAGGACGCTGT

GTGATCAAGTTCTGGACACTTTTCTGGGATG.
```

RT-PCR primers were designed for confirming differential expression, pulling out additional clones, screening for full-length mouse clone, and screening for the human clone. The RT-PCR primers were designed as follows:

65.pcr.top1:  5'-CAGAGGGTGGGTGGGAAAGAGTGA (SEQ ID NO:33)

and 65.pcr.bot2: 3'-CCTTCACTGTATTTCCTGCGACAC (SEQ ID NO:34)

exposed for autoradiography. Blots were rehybridized with a 75-bp synthetic probe from the human actin gene. See Godowski et al., *Proc. Natl. Acad. Sci. USA*, 86: 8083-8087 (1989) for a method for making a probe with overlapping oligos, which is how the actin probe was prepared.

4. cDNA Library Screening

Clones encoding the full-length mouse clone 65 polypeptide were isolated by screening RNA library 211: C57MG/Wnt-1 by colony hybridization with the above probe. The inserts of certain of these clones were subcloned into pBluescript™ IISK+ and their DNA sequence determined by dideoxy DNA sequencing on both strands.

5. Results

The recently described technique of SSH combines a high subtraction efficiency with an equalized representation of differentially expressed sequences. This method is based on specific PCR reactions that permit exponential amplification of cDNAs which differ in abundance, whereas amplification of sequences of identical abundance in two populations is suppressed. The SSH technique was used herein to isolate genes expressed in a mouse mammary myoepithelial cell transformed with Wnt-1 whose expression is reduced or absent in the parental myoepithelial cell. The polyA+RNA extracted from both types of cells was used to synthesize tester and driver cDNAs. The degree of subtraction efficiency was monitored by Southern blot analysis of unsubtracted and subtracted PCR products using a β-actin probe. No β-actin mRNA was apparent in the subtracted PCR products, confirming the efficiency of the subtraction.

After RT-PCR and Northern blot analysis were carried out on the initial clone to confirm differential expression, there was found about a 2-fold induction in the Wnt-1 cell line by Northern blot and a 4.5-fold induction by RT-PCR. Upon screening of the library, the full-length mouse clone 65 was obtained, designated clone 65.11.3. The cDNA for mouse clone 65 encodes a novel intracellular protein that is strongly induced in the Wnt-1/C57 mg cell line, but is absent, or at very low levels, in the parent/C57 mg cells. This clone, 65.11.3, encodes a protein about 48-60% identical in sequence to members of the Rho family of small GTPases.

The nucleotide sequence and putative amino acid sequence of mouse clone 65 are shown in FIGS. 1A and 1B (SEQ ID NOS:4 and 6, respectively). The alignment of the human and mouse clone 65 amino acid sequences is shown in FIG. 6 (SEQ ID NOS:3 and 6, respectively). The mouse clone was placed in pRK5E, described above, and deposited with the ATCC. Upon transformation into JM 109 cells, the plasmid renders the cells Amp resistant. Upon digestion with HindIII and NotI, the cells provide a mouse insert size of 786 base pairs from the Met codon to the stop codon. There are 1824 bp upstream of the NotI site encoding mouse heat-stable antigen (HSA) (CD24) fused to the clone 65 insert, which can be eliminated by digestion with NotI. Because the HSA sequence adjacent to the 5' end of the gene was removed electronically, there is no 5' sequence for clone 65 upstream of the Met in FIGS. 1A and 1B.

Without being limited to any one theory, the PCR/RT primers may fall in the 3' UTR of an alternatively spliced clone because the final clone 65.11.3 (mouse clone 65) does not have these sequences. A number of other clones were obtained by screening a C57 mg/Wnt-1 cDNA library using the specific probes described below.

Two subsequent clones, designated as 65.11 and 65.9 and having 2224 and 2004 bp respectively, were identified using a probe derived from the original 212 bp clone 65. Their sequences (SEQ ID NOS:12 and 13, respectively) are shown in FIGS. 10 and 11, respectively. Clones 65.11 and 65.9 have different 5' ends, virtually identical 3' ends, and CA repeats. The 5' end of clone 65.11 has a CDC-42-like region. The 5' end of clone 65.9 contains a region with homology to part of a 314-bp EST, AA462407 (isolated from a mouse mammary gland).

Three other clones were obtained from the same library by screening with a probe derived from the region homologous to CDC-42 of clone 65.11: clone 65.11.1 having 836 bp (SEQ ID NO:14; FIG. 12), the full-length mouse clone 65 clone 65.11.3 (SEQ ID NO:15; FIGS. 13A-13B) having 2251 bp, described below and the coding region of which is disclosed in FIGS. 1A-1B, and sharing a region in the 5' end with EST AA613604 (isolated from adult mouse placenta), and clone 65.11.6 having 847 bp (SEQ ID NO:16; FIG. 14). Three other clones (65.1, 65.6, and 65.13) were also obtained from the primary screen (using a portion of the original clone 65 as a probe, one of which (clone 65.1) has a 5' end similar to that of clone 65.9. The sequences of these clones (SEQ ID NOS:17, 18, and 19, respectively) are shown in FIGS. 15, 16, and 17, respectively.

The subsequent clones, which may be splice variants, contain pieces of the 3' end of the initial clone, and/or contain an unusual 5' end, and/or contain a CDC-42-like end.

Example 2

Isolation of a cDNA Clone Encoding Mouse Clone 320

The cDNA for mouse clone 320 was isolated independently by Wnt-1 differential screening using the procedure described in Example 1. The initial clone isolated was designated clone 320 and had 165 bp. There were two clones in this cluster. The clone was at least partially sequenced as described above and RT-PCR primers were designed as follows:

320.pcr.top1: (corresponding to bases 2319-2342 of FIGS. 4A-4B)

5'-GCACACACGCATGGAGGCAAGCTC (SEQ ID NO:43)

and 320.pcr.bot1: (corresponding to bases 2423-2446 of FIGS. 4A-4B)

3'-ACCACCTCGACATTTGTTCTACCG (SEQ ID NO:44)

RT-PCR and Northern blot procedures were carried out as described in Example 1 to confirm differential expression.

Then four clones encoding at least partial-length mouse clone 320 were isolated by screening RNA library 211: C57MG/Wnt-1 by colony hybridization with a probe designated 320.50.mer.1 of nucleotide bases 1997-2046 of FIGS. 4A-4B:

5'-CTCCTGACCTTTGGGGCTGCCACTTC-CCAGGACGACCACTGCCTGCCCAC (SEQ ID NO:45).

The cDNA for mouse clone 320 encodes a novel protein that is strongly induced in the Wnt-1/C57 mg cell line, but is absent in the parent/C57 mg cells and may be useful in the regulation of cancer cells.

The nucleotide sequence of a consensus sequence made up of all three clones (SEQ ID NO:7) is shown in FIGS. 4A and 4B. The nucleotide sequence of another clone of mouse clone 320 is shown in FIGS. 5A-5D (SEQ ID NO:8) and of yet another clone is shown in FIG. 6 (SEQ ID NO:9). The consensus sequence is a mouse clone 320 sequence of 2822 bp having no obvious or apparent open reading frame, and is probably a partial clone. When RNA from tumors arising in mice in a colony established from two Wnt-1 male transgenic mice (provided by Harold Varmus at NCI) was subjected to RT-PCR using the above primers, clone 320 was strongly induced. A small section of only about 200 bp of the consensus sequence matches a region in the 3'UTR of human Wnt-5A.

The mouse clone was placed in pRK5E, described above, and deposited with the ATCC. Upon transformation into JM 109 cells, the plasmid renders the cells ampicillin resistant. Upon digestion with BamHI and HindIII, this provides a mouse insert size of about 3 kilobase pairs.

Example 3

Isolation of a cDNA Clone Encoding Human Clone 65

To isolate the full-length human clone corresponding to 65.11.3 (mouse clone 65), a human fetal liver cDNA library (Clontech), treated with the SuperScript™ kit using the pRK5E vector as described above, was screened with a probe (65.50.mer.2 (SEQ ID NO:42) noted above in Example 1) at low stringency (20% formamide, 1×SSC, 55° C. wash).

Four clones were identified: 65.1, 65.4, 65.5, and 65.6. The inserts to these clones were subcloned into pBluescript™ IISK+ and its DNA sequence determined by dideoxy DNA sequencing on both strands. A consensus sequence from these clones was obtained to give both the nucleotide sequence and putative amino acid sequence for human clone 65. The consensus sequence and the derived amino acid sequence are shown in FIGS. 5A-5D (SEQ ID NOS:1 and 3, respectively). Clone 65.1 (SEQ ID NO:46) starts at nucleotide position 51 and ends at 227 of SEQ ID NO:1. The second clone 65.4 (SEQ ID NO:47) starts at nucleotide position 51 and ends at 824 of SEQ ID NO:1. The third clone 65.6 (SEQ ID NO:48) starts at nucleotide position 480 and ends at 1319 of SEQ ID NO:1) in FIGS. 5A-5B. This consensus sequence of FIGS. 5A-5B (SEQ ID NO:1) is 93% homologous to the mouse clone 65 nucleotide sequence of FIG. 1 (SEQ ID NO:4). See FIG. 6. By homology searching, human clone 65, like mouse clone 65, is found to be a member of the Rho, Rac, and CDC42 family. Because of the homology to the Rho and Rac family, these proteins are believed to be involved in the upregulation of cancer genes.

The clone was placed in a pRK5E plasmid as described above and deposited with the ATCC. Upon transformation into JM109 cells, the cells become ampicillin resistant. Digestion with XbaI and NotI yields an insert size of 777 basepairs from the ATG to the stop codon.

Example 4

In situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis, and aid in chromosome mapping.

In situ hybridization was performed following an optimized version of the protocol by Lu and Gillett, *Cell Vision* 1: 169-176 (1994), using PCR-generated. $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A ($^{33}$-P)UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed-vacuum dried. To each tube containing dried $^{33}$P-UTP, the following ingredients were added:

2.0 µl 5×transcription buffer
1.0 µl DTT (100 mM)
2.0 µl NTP mix (2.5 mM: 10 µl each of 10 mM GTP, CTP & ATP+10 µl H$_2$O)
1.0 µl UTP (50 µM)
1.0 µl RNAsin
1.0 µl DNA template (1 µg)
1.0 µl H$_2$O
1.0 µl RNA polymerase (for PCR products T3=AS, T7=S, usually)

The tubes were incubated at 37° C. for one hour. A total of 1.0 µl RQ1 DNase was added, followed by incubation at 37° C. for 15 minutes. A total of 90 µl TE (10 mM Tris pH 7.6/1 mM EDTA pH 8.0) was added, and the mixture was pipetted onto DE81 paper. The remaining solution was loaded in a MICROCON-50™ ultrafiltration unit, and spun using program 10 (6 minutes). The filtration unit was inverted over a second tube and spun using program 2 (3 minutes). After the final recovery spin, a total of 100 µl TE was added. Then 1 µl of the final product was pipetted on DE81 paper and counted in 6 ml of BIOFLUOR II™.

The probe was run on a TBE/urea gel. A total of 1-3 µl of the probe or 5 µl of RNA Mrk III was added to 3 µl of loading buffer. After heating on a 95° C. heat block for three minutes, the gel was immediately placed on ice. The wells of gel were flushed, and the sample was loaded and run at 180-250 volts for 45 minutes. The gel was wrapped in plastic wrap (SARAN™ brand) and exposed to XAR film with an intensifying screen in a –70° C. freezer one hour to overnight.

$^{33}$P-Hybridization

A. Pretreatment of Frozen Sections

The slides were removed from the freezer, placed on aluminum trays, and thawed at room temperature for 5 minutes. The trays were placed in a 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+ 975 ml s.c. H$_2$O). After deproteination in 0.5 µg/ml proteinase K for 10 minutes at 37° C. (12.5 µl of 10 mg/ml stock in 250 ml prewarmed RNAse-free RNAse buffer), the sections were washed in 0.5×SSC for 10 minutes at room temperature. The sections were dehydrated in 70%, 95%, and 100% ethanol, 2 minutes each.

B. Pretreatment of Paraffin-embedded Sections

The slides were deparaffinized, placed in s.c. H$_2$O, and rinsed twice in 2×SSC at room temperature, for 5 minutes each time. The sections were deproteinated in 20 µg/ml proteinase K (500 µl of 10 mg/ml in 250 ml RNAse-free RNAse buffer; 37° C., 15 minutes) for human embryo tissue, or 8× proteinase K (100 µl in 250 ml RNASE buffer, 37° C., 30 minutes) for formalin tissues. Subsequent rinsing in 0.5×SSC and dehydration were performed as described above.

C. Prehybridization

The slides were laid out in a plastic box lined with Box buffer (4×SSC, 50% formamide) The filter paper was saturated. The tissue was covered with 50 µl of hybridization buffer (3.75 g dextran sulfate +6 ml s.c. H$_2$O), vortexed, and heated in the microwave for 2 minutes with the cap loosened. After cooling on ice, 18.75 ml formamide, 3.75 ml 20×SSC, and 9 ml s.c. H$_2$O were added, and the tissue was vortexed well and incubated at 42° C. for 1-4 hours.

D. Hybridization 1.0×10$^6$ cpm probe and 1.0 µl tRNA (50 mg/ml stock) per slide were heated at 95° C. for 3 minutes. The slides were cooled on ice, and 48 µl hybridization buffer was added per slide. After vortexing, 50 µl $^{33}$P mix was added to 50 µl prehybridization on the slide. The slides were incubated overnight at 55° C.

E. Washes

Washing was done for 2×10 minutes with 2×SSC, EDTA at room temperature (400 ml 20×SSC+16 ml 0.25 M EDTA, $V_f$=4 L), followed by RNAseA treatment at 37° C. for 30 minutes (500 µl of 10 mg/ml in 250 ml RNAse buffer=20

μg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4 L).

F. Oligonucleotides

In situ analysis was performed on DNA sequences disclosed herein. The oligonucleotides employed for these analyses are as follows.

```
(1) Clone 65.11
p1: 5'-GGA TTC TAA TAC GAC TCA CTA TAG GGC AGC GTT
GAC TCA GAA AAA CC-3'(SEQ ID NO:49)

p2: 5'-CTA TGA AAT TAA CCC TCA CTA AAG GGA GCA TAT
GAA TTT CAG CCC TAA-3'(SEQ ID NO:50)

(2) Clone 320.50
p3: 5'-GGA TTC TAA TAC GAC TCA CTA TAG GGC ACG CAC
ATC TGT TTC CGT TTT-3'(SEQ ID NO:51)

p4: 5'-CTA TGA AAT TAA CCC TCA CTA AAG GGA CCA TCC
CCG CTC TCT ACC TA-3'(SEQ ID NO:52)
```

G. Results

In situ analysis was performed on the above DNA sequences disclosed herein. The results from these analyses are as follows.

(1) Clone 65.11

Expression in Mouse tissues: This clone was expressed in developing spinal ganglia of an E15.5 mouse and in the cardiac valve cusps of an adult mouse.

(2) Clone 320.50

Expression in Mouse tissues: This clone was expressed in the pyramidal cell layer of hippocampus and dentate gyrus of an adult mouse brain. It was also expressed in the lung, renal medulla, and whisker follicles of an E15.5 mouse.

Example 5

Use of DNA Encoding Clone 65 and 320 Polypeptides as a Hybridization Probe

The following method describes use of a nucleotide sequence encoding a clone 65 or 320 polypeptide as a hybridization probe.

DNA comprising the coding sequence of full-length human clone 65 (as shown in FIGS. 5A-5D, SEQ ID NO:3), or of mouse clone 65 (as shown in FIGS. 1A and 1B, SEQ ID NO:6), or of full-length mouse clone 320 (the partial sequences shown in FIGS. 2, 3, and 4; SEQ ID NOS:7, 8, and 9, respectively) is employed as a probe to screen for homologous DNAs (such as those encoding naturally-occurring variants of these particular clone 65: and 320 polypeptides in human tissue cDNA libraries or human tissue genomic libraries.

Hybridization and washing of filters containing either library DNAs is performed under the following high-stringency conditions. Hybridization of radiolabeled clone 65-polypeptide- or clone 320-polypeptide-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding a full-length, native-sequence clone 65 or 320 polypeptide can then be identified using standard techniques known in the art.

Example 6

Expression of Clone 65 or 320 Polypeptide in E. coli

This example illustrates preparation of an unglycosylated form of clone 65 or 320 polypeptide by recombinant expression in E. coli.

The DNA sequence encoding clone 65 or 320 polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR-amplified sequences are then ligated into the vector. The vector will preferably include sequences which encode an antibiotic-resistance gene, a trp promoter, a polyhis leader (including the first six STII codons, polyhis sequence, and enterokinase cleavage site), the clone 65-coding or clone 320-coding region, lambda transcriptional terminator, and an argU gene.

The ligation mixture is then used to transform a selected E. coli strain using the methods described in Sambrook et al., supra. Transformants are identified by their ability to grow on LB plates, and antibiotic-resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger-scale culture. The cells are then grown to a desired optical density, during which the expression promoter is turned on.

After the cells are cultured for several more hours, the cells can be harvested by centrifugation. The cell pellet obtained by the centrifugation can be solubilized using various agents known in the art, and the clone 65 or 320 polypeptide can then be purified using a metal-chelating column under conditions that allow tight binding of the protein.

Example 7

Expression of Clone 65 or 320 Polypeptide in Mammalian Cells

This example illustrates preparation of a potentially glycosylated form of clone 65 or 320 polypeptide by recombinant expression in mammalian cells.

The vector, pRK5E, may be employed as the expression vector. The appropriate DNA encoding clone 65 or 320 polypeptide is ligated into pRK5E with selected restriction enzymes to allow insertion of the DNA for clone 65 or 320 polypeptide using ligation methods as described in Sambrook et al., supra. The resulting vectors are conveniently referred to generically as pRK5E.clone65 or pRK5E.clone320, respectively, in the general description below.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5E.clone65 or pRK5E.clone320 DNA is mixed with about 1 μg DNA encoding the VA RNA gene (Thimmappaya et al., Cell, 31:543 (1982)) and dissolved in 500 μl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in phosphate-buffered saline (PBS) is added for 30 seconds. The 293 cells are then washed with serum-free medium, fresh medium is added, and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12-hour incubation, the conditioned medium is collected, concentrated on a spin filter, and loaded onto a 15% SDS gel. The processed gel may be dried and exposed to film for a selected period of time to reveal the presence of the clone 65 or 320 polypeptide. The cultures containing transfected cells may undergo further incubation (in serum-free medium) and the medium is tested in selected bioassays.

In an alternative technique, the clone 65 or 320 polypeptide may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5E.clone65 or pRK5E.clone320 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin, and 0.1 µg/ml bovine transferrin. After about four days, the conditioned media are centrifuged and filtered to remove cells and debris. The sample containing expressed clone 65 or 320 polypeptide can then be concentrated and purified by any selected method, such as dialysis and/or column chromatography.

In another embodiment, the clone 65 or 320 polypeptide can be expressed in CHO cells. The pRK5E.clone65 or pRK5E.clone320 can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of the clone 65 or 320 polypeptide, the culture medium may be replaced with serum-free medium. Preferably, the cultures are incubated for about 6 days, and then the conditioned medium is harvested. The medium containing the expressed clone 65 or 320 polypeptide can then be concentrated and purified by any selected method.

Epitope-tagged clone 65 or 320 polypeptide may also be expressed in host CHO cells. The clone 65 or 320 polypeptide may be subcloned out of the pRK5 vector. Suva et al., *Science*, 237: 893-896 (1987); EP 307,247 published Mar. 15, 1989. The subclone insert can undergo PCR to fuse in-frame with a selected epitope tag such as a poly-his tag into a baculovirus expression vector. The poly-his-tagged clone 65 or 320 polypeptide insert can then be subcloned into a SV40-driven vector containing a selection marker such as DHFR for selection of stable clones. Finally, the CHO cells can be transfected (as described above) with the SV40-driven vector. Labeling may be performed, as described above, to verify expression. The culture medium containing the expressed poly-His tagged clone 65 or 320 polypeptide can then be concentrated and purified by any selected method, such as by Ni$^{2+}$-chelate affinity chromatography.

Example 8

Expression of Clone 65 or 320 Polypeptide in Yeast

The following method describes recombinant expression of a clone 65 or 320 polypeptide in yeast.

First, yeast expression vectors are constructed for intracellular production or secretion of a clone 65 or 320 polypeptide from the ADH2/GAPDH promoter. DNA encoding a clone 65 or 320 polypeptide and the promoter is inserted into suitable restriction enzyme sites in the selected plasmid to direct intracellular expression. For secretion, DNA encoding a clone 65 or 320 polypeptide can be cloned into the selected plasmid, together with DNA encoding the ADH2/GAPDH promoter, a native clone 65 or clone 320 signal peptide or other mammalian signal peptide or yeast alpha-factor or invertase secretory signal/leader sequence, and linker sequences (if needed) for expression.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant clone 65 or 320 polypeptide can subsequently be isolated and purified by removing the yeast cells from the fermentation medium by centrifugation and then concentrating the medium using selected cartridge filters. The concentrate containing the clone 65 or 320 polypeptide may further be purified using selected column chromatography resins.

Example 9

Expression of Clone 65 or 320 Polypeptide in Baculovirus-Infected Insect Cells

The following method describes recombinant expression of a clone 65 or 320 polypeptide in baculovirus-infected insect cells.

The sequence coding for clone 65 or 320 polypeptide is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding clone 65 or 320 polypeptide or the desired portion of the coding sequence (such as the sequence encoding the mature protein if the protein is extracellular) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus Expression Vectors: A Laboratory Manual* (Oxford: Oxford University Press, 1994).

Expressed poly-his-tagged clone 65 or 320 polypeptide can then be purified, for example, by Ni$^{2+}$-chelate affinity chromatography as follows. Extracts are prepared from recombinant virus-infected Sf9 cells as described by Rupert et al., *Nature,* 362:175-179 (1993). Briefly, Sf9 cells are washed, resuspended in sonication buffer (25 mL HEPES, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8), and filtered through a 0.45 µm filter. A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes non-specifically bound protein. After reaching A280 baseline again, the column is developed with a 0 to 500 mM imidazole gradient in the secondary wash buffer. One-mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged clone 65 or 320 polypeptide are pooled and dialyzed against loading buffer.

Alternatively, purification of the IgG-tagged (or Fc-tagged) clone 65 or 320 polypeptide can be performed using known chromatography techniques, including, for instance, Protein A or protein G column chromatography.

Example 10

Preparation of Antibodies that Bind Clone 65 or 320 Polypeptide

1. Polyclonal Antibodies

Polyclonal antisera are generated in female New Zealand White rabbits against murine and human clone 65 polypeptide and against murine clone 320 polypeptide. The antigens used are proteins fused with histidine or with the Fc portion of IgG. Each protein is homogenized with Freund's complete adjuvant for the primary injection and with Freund's incomplete adjuvant for all subsequent boosts. For the primary immunization and the first boost, 3.3 µg per kg body weight is injected directly into the popliteal lymph nodes as described in Bennett et al., *J. Biol. Chem.,* 266: 23060-23067 (1991) and "Production of Antibodies by Inoculation into Lymph Nodes" by Morton Sigel et al. in *Methods in Enzymology,* Vol. 93 (New York: Academic Press, 1983). For all subsequent boosts, 3.3 µg per kg body weight is injected into subcutaneous and intramuscular sites. Injections are done every 3 weeks with bleeds taken on the following two weeks.

2. Monoclonal Antibodies

Techniques for producing monoclonal antibodies that can specifically bind a clone 65 or 320 polypeptide are known in the art and are described, for instance, in Goding, supra. Immunogens that may be employed include purified clone 65 or 320 polypeptide, fusion proteins containing clone 65 or 320 polypeptide, and cells expressing recombinant clone 65 or 320 polypeptide on the cell surface. Selection of the immunogen can be made by the skilled artisan without undue experimentation.

Mice, such as Balb/c, are immunized with the clone 65 or 320 immunogen emulsified in complete Freund's adjuvant and injected subcutaneously or intraperitoneally in an amount from 1 to 100 micrograms. Alternatively, the immunogen is emulsified in. MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect antibodies to clone 65 or 320 polypeptide.

After a suitable antibody titer has been detected, the animals "positive" for antibodies can be injected with a final intravenous injection of a clone 65 or 320 polypeptide. Three to four days later, the mice are sacrificed and the spleen cells are harvested. The spleen cells are then fused (using 35% PEG) to a selected murine myeloma cell line such as P3X63AgU.1, available from ATCC, No. CRL 1597. The fusions generate hybridoma cells which can then be plated in 96-well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against a clone 65 or 320 polypeptide. Determination of "positive" hybridoma cells secreting the desired monoclonal antibodies against a clone 65 or 320 polypeptide is within the skill in the art.

The positive hybridoma cells can be injected intraperitoneally into syngeneic Balb/c mice to produce ascites containing the anti-clone 65 or 320 polypeptide monoclonal antibodies, Alternatively, the hybridoma cells can be grown in tissue culture flasks or roller bottles. Purification of the monoclonal antibodies produced in the ascites can be accomplished using ammonium sulfate precipitation, followed by gel-exclusion chromatography. Alternatively, affinity chromatography based upon binding of antibody to protein A or protein G can be employed.

Example 11

One Use of Antibodies that Bind Clone 65 or 320 Polypeptide

1. Cell Lines

The established human breast tumor cells BT474 and MDA-MB-231 (which are available from ATCC) are grown in minimum essential medium (Gibco, Grand Island, N.Y.) supplemented with 10% heat-inactivated fetal bovine serum (FBS) (Hyclone, Logan, Utah), sodium pyruvate, L-glutamine (2 mM), non-essential amino acids, and 2× vitamin solution and maintained at 37° C. in 5% $CO_2$. Zhang et al., *Invas. & Metas.,* 11:204-215 (1991); Price et al., *Cancer Res.,* 50:717-721 (1990).

2. Antibodies

Anti-clone 65 or anti-clone 320 monoclonal antibodies that may be prepared as described above are harvested with PBS containing 25 mM EDTA and used to immunize BALB/c mice. The mice are given injections i.p. of $10^7$ cells in 0.5 ml PBS on weeks 0, 2, 5 and 7. The mice with antisera that immunoprecipitated $^{32}$P-labeled Wnt-1 are given i.p. injections of a wheat-germ agglutinin-Sepharose (WGA) purified Wnt membrane extract on weeks 9 and 13. This is followed by an i.v. injection of 0.1 ml of the Wnt-1 preparation and the splenocytes are fused with mouse myeloma line X63-Ag8.653. Hybridoma supernatants are screened for Wnt-1 binding by ELISA and radioimmunoprecipitation. MOPC-21 (IgG1) (Cappell, Durham, N.C.) is used as an isotype-matched control.

Additionally, the anti-ErbB2 IgG$_1$κ murine monoclonal antibodies 4D5 (ATCC CRL 10463 deposited May 24, 1990) and 7C2, specific for the extracellular domain of ErbB2, may be used with the above antibodies. They are produced as described in Fendly et al., *Cancer Research,* 50:1550-1558 (1990) and WO89/06692.

3. Analysis of Cell Cycle Status and Viability

Cells are simultaneously examined for viability and cell cycle status by flow cytometry on a FACSTAR PLUS™ (Becton Dickinson Immunocytometry Systems USA, San Jose, Calif.). Breast tumor cells are harvested by washing the monolayer with PBS, incubating cells in 0.05% trypsin and 0.53 mM EDTA (Gibco), and resuspending them in culture medium. The cells are washed twice with PBS containing 1% FBS and the pellet is incubated for. 30 minutes on ice with 50 μl of 400 μM 7-aminoactinomycin D (7AAD) (Molecular Probes, Eugene, Oreg.), a vital dye which stains all permeable cells. Cells are then fixed with 1.0 ml of 0.5% paraformaldehyde in PBS and simultaneously permeabilized and stained for 16 hours at 4° C. with 220 μl of 10 μg/ml HOECHST 33342™ dye (also a DNA binding dye) containing 5% TWEEN 20™.

The data from 1×10$^4$ cells are collected and stored using LYSYS II™ software and analyzed using PAINT-A-GATE™ software (Becton Dickinson). Darzynkiewica et al., *Cytometry,* 13:795-808 (1992); Picker et al., *J. Immunol.,* 150:1105-1121 (1993). The viability and percentage of cells in each stage of the cell cycle are determined on gated single cells using 7AAD and Hoechst staining, respectively. (Cell doublets are excluded by pulse analysis of width vs. area of the Hoechst signal.) Cell numbers are determined using a hemocytometer.

4. Affinity of Binding to Putative Receptor

Radioiodinated anti-clone 65 and anti-clone 320 antibodies are prepared by the Iodogen™ method. Fracker et al., *Biochem. Biophys. Res. Comm.,* 80:849-857 (1978). Binding assays are performed using appropriate receptor-expressing cells cultured in 96-well tissue culture plates (Falcon, Becton Dickinson Labware, Lincoln Park, N.J.). The cells are trypsinized and seeded in wells of 96-well plates at a density of 10$^4$ cells/well and allowed to adhere overnight. The monolayers are washed with cold culture medium supplemented with 0.1% sodium azide and then incubated in triplicate with 100 μl of serial dilutions of $^{125}$I-anti-clone 65 or clone 320 antibodies in cold culture medium containing 0.1% sodium azide for 4 hours on ice. Non-specific binding is estimated by the preincubation of each sample with a 100-fold molar excess of nonradioactive antibodies in a total volume of 100 μl. Unbound radioactivity is removed by two washes with cold medium containing 0.1% sodium azide. The cell-associated radioactivity is detected in a gamma counter after solubilization of the cells with 150 μl of 0.1 M NaOH/well. The clone 65 polypeptide and clone 320 polypeptide binding constants (K$_d$) and anti-clone 65 and anti-clone 320 antibody binding affinities are determined by Scatchard analysis.

It is expected that the antibodies against clone 65 and clone 320 polypeptides will affect the growth of these cells.

Deposit of Material

The following materials have been deposited with the American Type Culture Collection, 10801 University Blvd., Manassas, Va., USA (ATCC):

| Material | ATCC Dep. No. | Deposit Date |
|---|---|---|
| pRK5E.h.WIG-3.65.4A | 209536 | Dec. 10, 1997 |
| pRK5E.m.WIG-3.65.11.3 | 209535 | Dec. 10, 1997 |
| pRK5E.m.WIG-4.320.9 | 209534 | Dec. 10, 1997 |

These deposits were made under the provisions of the Budapest Treaty on the International Recognition of the Deposit of Microorganisms for the Purpose of Patent Procedure and the Regulations thereunder (Budapest Treaty). This assures maintenance of viable cultures of the deposits for 30 years from the date of deposit. The deposits will be made available by ATCC under the terms of the Budapest Treaty, and subject to an agreement between Genentech, Inc. and ATCC, which assures permanent and unrestricted availability of the progeny of the cultures of the deposits to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886OG 638).

The assignee of the present application has agreed that if a culture of the materials on deposit should die or be lost or destroyed when cultivated under suitable conditions, the materials will be promptly replaced on notification with another of the same. Availability of the deposited materials is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the constructs deposited, since the deposited embodiment is intended as a single illustration of certain aspects of the invention and any constructs that are functionally equivalent are within the scope of this invention. The deposits of materials herein do not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated clone 65 polypeptide comprising the amino acid sequence of human clone 65 polypeptide of SEQ ID NO: 3 or the amino acid sequence of mouse clone 65 polypeptide of SEQ ID NO: 6.

2. A chimeric molecule comprising a polypeptide of claim 1 fused to a heterologous amino acid sequence.

3. The chimeric molecule of claim 2 wherein said heterologous amino acid sequence is an epitope tag sequence or an Fc region of an immunoglobulin.

4. A composition comprising the polypeptide of claim 1 and a carrier therefor.

* * * * *

SEQUENCE LISTING

<160> NUMBER OF SEQ ID NOS: 52

<210> SEQ ID NO 1
<211> LENGTH: 3960
<212> TYPE: DNA
<213> ORGANISM: Human

<400> SEQUENCE: 1

| | | | |
|---|---|---|---|
| ctccaacagc gcagggcaga gcggctggcg ccgccggagc gcggagccac | 50 |
| gaccctccct ggccgccttt gtctactggc cgtgcggccc ggaaccgcca | 100 |
| ctctccaggg ccggggacgc gcccgcagct gtcggtgaca gctcctccct | 150 |
| accgcaaccc tccggggcgg aggggcggtc gggccgggcc ctgctagccc | 200 |
| gcgaccgcaa gcccgcgctc gcggatcgat gccccgcag caggggggacc | 250 |
| ccgcgttccc cgaccgctgc gaggcgcctc cggtgccgcc gcgtcgggag | 300 |
| cgcggtggac gcggggggacg cgggcctggg gagccggggg gccggggggcg | 350 |
| tgcggggggt gccgaggggc gcggcgtcaa gtgcgtgctg gtcggcgacg | 400 |
| gcgcggtggg caagacgagc ctggtggtga gttacaccac caacggctac | 450 |
| cccaccgagt acatccctac tgccttcgac aacttctccg cggtggtgtc | 500 |
| tgtggatggg cggcccgtga gactccaact ctgtgacact gccggacagg | 550 |
| atgaatttga caagctgagg cctctctgct acaccaacac agacatcttc | 600 |
| ctgctctgct tcagtgtcgt gagcccctca tccttccaga acgtcagtga | 650 |
| gaaatgggtg ccggagattc gatgccactg tcccaaagcc cccatcatcc | 700 |
| tagttggaac gcagtcggat ctcagagaag atgtcaaagt cctcattgag | 750 |
| ttggacaaat gcaaagaaaa gccagtgcct gaagaggcgg ctaagctgtg | 800 |
| cgccgaggaa atcaaagccg cctcctacat cgagtgttca gccttgactc | 850 |
| aaaaaaacct caaagaggtc tttgatgcag ccatcgtcgc tggcattcaa | 900 |
| tactcggaca ctcagcaaca gccaaagaag tctaaaagca ggactccaga | 950 |
| taaaatgaaa aacctctcca gtcctggtg aagaagtac tgctgtttcg | 1000 |
| tatgatgctg gcaagacacc cagaaaggct attttcagat gaaatcgata | 1050 |
| ttagaagcta tattagctga aacaactcct tttactgcgt agaacctata | 1100 |
| tcgagagtgt gtgtatatgt attataggag gagctctcaa ttttatgtat | 1150 |
| tctttctgcc tttaattttc ttgtttgttt gagcttaggg atgagatact | 1200 |
| tatgcaagat atttttgaag taaattaaac attttttcaca tctctggaaa | 1250 |
| tttagagttc tagacctctg gttaatttat atctaatatg aagaagacac | 1300 |
| ctctaatctg gatgttaaga atgaagttct gctacattat aatgtacaga | 1350 |
| agagcaaaag ggaggaacac tatggttaac cctctcttga ttaagggcta | 1400 |
| cttaatgcac agtgcattat gtacacaggt caaccatggt aacaatagtt | 1450 |
| cttagctttg aaactccatg caaaccatgc cttttttta aggagcaaaa | 1500 |
| atctgagaaa aaagtgaga gacctctgcc tacaaaactt caaaccagtc | 1550 |
| acttttgtca attgctaata cccagttact tatgatttaa aaacaaccaa | 1600 |
| cagaaaacat cccacagact gtatggcact ctgtagtcaa aaaaggaaac | 1650 |
| tttcttattg ggacttttct ttcttagtcc agttgtgttg acacatatga | 1700 |
| acacagacaa agtgctatgc ggaggaaagc aagtgttggt cagtagtttc | 1750 |
| atgttttagg gagtggttcc tgtggagatc agaaagtgac atttgctttc | 1800 |
| ggtactgtaa tacatgcacc aaactgcctc aatcctaggt aacgagggca | 1850 |
| acagggagca cctgtctgga ttgttttaa acctccatac tcaagctgtc | 1900 |

-continued

| | |
|---|---|
| tcttcggcag ggaggtgaat actcttgaaa ggccaacagc aagtgtttgt | 1950 |
| gggacacaac acagataatt tttcttaag tcgaccaaga tgtacttctc | 2000 |
| tgtgtgcaca cccatgcaca ctcatgcaca cagatacata ggtctgtatg | 2050 |
| gctgtatttg ctgttgattc agactttcac accattaatg gggaaaagcg | 2100 |
| tggccacaaa aacagatgct aggaagcttg gcttcctctt cttgttgacc | 2150 |
| cttttttgaa ccaacatctt ttttattata ttcagagtat gttttaagt | 2200 |
| gtatcttaat atatacattt tttaggacat cttaaatcta aacaaaaaat | 2250 |
| aaaatgaaca tctcttgaaa cctgttaaaa caaccagtta aagccacaga | 2300 |
| tggcttcag ggcagtagca gcagaggcca gtggactctg aggactcctg | 2350 |
| aggggcgggg cgtgtagcca gccaggtgca tgccgggacc atggccccca | 2400 |
| tacttggctg cttcctgtga cagtgaaata catccttcaa ggtggcagct | 2450 |
| gttagggctg aatcttctgg agaaaaaggt gccatctcag gagaatagct | 2500 |
| tttactctgg taggaatgct tccgagacac cacaaggcag cctgaacact | 2550 |
| cagttgcagg gtcgggcttg cggtgggtga cccagagcca ccaaagtcac | 2600 |
| atccacaact aatgagggaa atctgtaaag ccagttagat agaagagttt | 2650 |
| tattttctg tgggttttgt gttgtcttttt ttatgttaaa aagaaatcca | 2700 |
| gtttgtgttt ttctatagaa aaagtaaaag atcaggttat actttaggtt | 2750 |
| aggggttcta tttattcctg ttagtaaata aaattaacaa atttctttgt | 2800 |
| ttaacaaaag attaatcttt aaaccactaa aatacataga ctgattgatt | 2850 |
| attcaacaca ttggaattga tgtcggtcat agtttcctga agcatttagt | 2900 |
| tacaacctga aggaataaaa tgatttgtgg aaatgcttaa aatagaccta | 2950 |
| actgaataca gtctcatctt gccgcgcctg gcttacctat ctgtggaaag | 3000 |
| ctaggcttcc caggtgggct ctgcctgtct ggtgcctgga ggtgtgggag | 3050 |
| ggaagatgag ttatttaact ggtaagcgat ttgaaacact atttttatat | 3100 |
| taaagtaaat ggcatggagt atagtgcaaa ttcatttta agatagaaca | 3150 |
| caaaacttga aagaagtttt atgcgtgtga cagtgtatgg ggctgcagtt | 3200 |
| ggtctccctg gagggacctt ccacacctcc tgcctttagg ccatgggtgg | 3250 |
| aaagtgctca gtgaagtaca cctgtgtggc ccagttctga aagctttata | 3300 |
| cagttgaatt ttaagtgggg ttgataacac cttggactgt tagtgttaaa | 3350 |
| aatctagtgg gttgaccttt aaatgcacag tttttaaaat atattgctgc | 3400 |
| attttataga atagtaaagg tacgattata cttgagattt tcctccattt | 3450 |
| ttatttcttc gtgaacatag agtttggggc cgaaaatgtt tttaaagtat | 3500 |
| gtgtttgagt taaatataaa gttggttcac ttcaaagcta aaaaattgtt | 3550 |
| aaacttgcag cttggtattg cagagaagat tttataagaa ttttgcttta | 3600 |
| gagaatgcca ctttggctga actacaagtg taggccacca ttataattta | 3650 |
| taaatccagc atacttcaaa actgtttgtt atctcttgtt accatgtatg | 3700 |
| tataaatgga cctttttataa ccttgttctc tgcttgacag actcaagaga | 3750 |
| aactacccag gtattacaca agccaaaatg ggagcaaggc cttctctcca | 3800 |
| gactatcgta acctggtgcc ttaccaagtt gtgcttttct gttttcaagt | 3850 |
| gtaaatgatg ttgagcagaa tgttgtactt gaaaatgcta taagtgagat | 3900 |

```
ggtatgaaat aaattctgac ttatgaatat aaaaaaaaaa aaaaaaaaaa        3950
aaaaaaaaaa                                                   3960

<210> SEQ ID NO 2
<211> LENGTH: 3960
<212> TYPE: DNA
<213> ORGANISM: Human

<400> SEQUENCE: 2
tttttttttt tttttttttt tttttttttt atattcataa gtcagaattt          50
atttcatacc atctcactta tagcattttc aagtacaaca ttctgctcaa         100
catcatttac acttgaaaac agaaaagcac aacttggtaa ggcaccaggt         150
tacgatagtc tggagagaag gccttgctcc cattttggct tgtgtaatac         200
ctgggtagtt tctcttgagt ctgtcaagca gagaacaagg ttataaaagg         250
tccatttata catacatggt aacaagagat aacaaacagt tttgaagtat         300
gctggattta taaattataa tggtggccta cacttgtagt tcagccaaag         350
tggcattctc taaagcaaaa ttcttataaa atcttctctg caataccaag         400
ctgcaagttt aacaattttt tagctttgaa gtgaaccaac tttatattta         450
actcaaacac atactttaaa aacattttcg gccccaaact ctatgttcac         500
gaagaaataa aaatggagga aaatctcaag tataatcgta cctttactat         550
tctataaaat gcagcaatat attttaaaaa ctgtgcattt aaaggtcaac         600
ccactagatt tttaacacta acagtccaag gtgttatcaa ccccacttaa         650
aattcaactg tataaagctt tcagaactgg gccacacagg tgtacttcac         700
tgagcacttt ccacccatgg cctaaaggca ggaggtgtgg aagtcccctc         750
cagggagacc aactgcagcc ccatacactg tcacacgcat aaaacttctt         800
tcaagttttg tgttctatct taaaaatgaa tttgcactat actccatgcc         850
atttacttta atataaaaat agtgtttcaa atcgcttacc agttaaataa         900
ctcatcttcc ctcccacacc tccaggcacc agacaggcag agcccacctg         950
ggaagcctag ctttccacag ataggtaagc caggcgcggc aagatgagac        1000
tgtattcagt taggtctatt ttaagcattt ccacaaatca ttttattcct        1050
tcaggttgta actaaatgct tcaggaaact atgaccgaca tcaattccaa        1100
tgtgttgaat aatcaatcag tctatgtatt ttagtggttt aaagattaat        1150
cttttgttaa acaagaaat tgttaattt tatttactaa caggaataaa         1200
tagaacccct aacctaaagt ataacctgat cttttacttt ttctatagaa        1250
aaacacaaac tggatttctt tttaacataa aaaagacaac acaaaaccca        1300
cagaaaaata aaactcttct atctaactgg ctttacagat ttccctcatt        1350
agttgtggat gtgactttgg tggctctggg tcacccaccg caagcccgac        1400
cctgcaactg agtgttcagg ctgccttgtg gtgtctcgga agcattccta        1450
ccagagtaaa agctattctc ctgagatggc acctttttct ccagaagatt        1500
cagccctaac agctgccacc ttgaaggatg tatttcactg tcacaggaag        1550
cagccaagta tgggggccat ggtcccggca tgcacctggc tggctacacg        1600
ccccgcccct caggagtcct cagagtccac tggcctctgc tgctactgcc        1650
```

| | |
|---|---|
| ctgaaagcca tctgtggctt taactggttg ttttaacagg tttcaagaga | 1700 |
| tgttcatttt atttttttgtt tagatttaag atgtcctaaa aaatgtatat | 1750 |
| attaagatac acttaaaaac atactctgaa tataataaaa aagatgttgg | 1800 |
| ttcaaaaaag ggtcaacaag aagaggaagc caagcttcct agcatctgtt | 1850 |
| tttgtggcca cgcttttccc cattaatggt gtgaaagtct gaatcaacag | 1900 |
| caaatacagc catacagacc tatgtatctg tgtgcatgag tgtgcatggg | 1950 |
| tgtgcacaca gagaagtaca tcttggtcga cttaagaaaa aattatctgt | 2000 |
| gttgtgtccc acaaacactt gctgttggcc tttcaagagt attcacctcc | 2050 |
| ctgccgaaga gacagcttga gtatggaggt ttaaaaacaa tccagacagg | 2100 |
| tgctccctgt tgccctcgtt acctaggatt gaggcagttt ggtgcatgta | 2150 |
| ttacagtacc gaaagcaaat gtcactttct gatctccaca ggaaccactc | 2200 |
| cctaaaacat gaaactactg accaacactt gctttcctcc gcatagcact | 2250 |
| ttgtctgtgt tcatatgtgt caacacaact ggactaagaa agaaaagtcc | 2300 |
| caataagaaa gtttccttt ttgactacag agtgccatac agtctgtggg | 2350 |
| atgttttctg ttggttgttt ttaaatcata agtaactggg tattagcaat | 2400 |
| tgacaaaagt gactggtttg aagttttgta ggcagaggtc tctcactttt | 2450 |
| tttctcagat ttttgctcct taaaaaaaag gcatggtttg catggagttt | 2500 |
| caaagctaag aactattgtt accatggttg acctgtgtac ataatgcact | 2550 |
| gtgcattaag tagcccttaa tcaagagagg gttaaccata gtgttcctcc | 2600 |
| cttttgctct tctgtacatt ataatgtagc agaacttcat tcttaacatc | 2650 |
| cagattagag gtgtcttctt catattagat ataaattaac cagaggtcta | 2700 |
| gaactctaaa tttccagaga tgtgaaaaat gtttaattta cttcaaaaat | 2750 |
| atcttgcata agtatctcat ccctaagctc aaacaaacaa gaaaattaaa | 2800 |
| ggcagaaaga atacataaaa ttgagagctc ctcctataat acatatacac | 2850 |
| acactctcga tataggttct acgcagtaaa aggagttgtt tcagctaata | 2900 |
| tagcttctaa tatcgatttc atctgaaaat agcctttctg ggtgtcttgc | 2950 |
| cagcatcata cgaaacagca gtacttcttc caccaggact tggagaggtt | 3000 |
| tttcattttta tctggagtcc tgcttttaga cttctttggc tgttgctgag | 3050 |
| tgtccgagta ttgaatgcca gcgacgatgg ctgcatcaaa gacctctttg | 3100 |
| aggtttttttt gagtcaaggc tgaacactcg atgtaggagg cggctttgat | 3150 |
| ttcctcggcg cacagcttag ccgcctcttc aggcactggc ttttcttgc | 3200 |
| atttgtccaa ctcaatgagg actttgacat cttctctgag atccgactgc | 3250 |
| gttccaacta ggatgatggg ggctttggga cagtggcatc gaatctccgg | 3300 |
| cacccatttc tcactgacgt tctggaagga tgagggctc acgacactga | 3350 |
| agcagagcag gaagatgtct gtgttggtgt agcagagagg cctcagcttg | 3400 |
| tcaaattcat cctgtccggc agtgtcacag agttggagtc tcacgggccg | 3450 |
| cccatccaca gacaccaccg cggagaagtt gtcgaaggca gtagggatgt | 3500 |
| actcggtggg gtagccgttg gtggtgtaac tcaccaccag gctcgtcttg | 3550 |
| cccaccgcgc cgtcgccgac cagcacgcac ttgacgccgc gccctcggc | 3600 |
| accccccgca cgcccccggc cccccggctc cccaggcccg cgtcccccgc | 3650 |

```
gtccaccgcg ctcccgacgc ggcggcaccg gaggcgcctc gcagcggtcg        3700
gggaacgcgg ggtcccccctg ctgcgggggc atcgatccgc gagcgcgggc       3750
ttgcggtcgc gggctagcag ggcccggccc gaccgcccct ccgccccgga        3800
gggttgcggt agggaggagc tgtcaccgac agctgcgggc gcgtccccgg        3850
ccctggagag tggcggttcc gggccgcacg gccagtagac aaaggcggcc        3900
agggagggtc gtggctccgc gctccggcgg cgccagccgc tctgccctgc        3950
gctgttggag                                                    3960
```

<210> SEQ ID NO 3
<211> LENGTH: 258
<212> TYPE: PRT
<213> ORGANISM: Human

<400> SEQUENCE: 3

```
Met Pro Pro Gln Gln Gly Asp Pro Ala Phe Pro Asp Arg Cys Glu
 1               5                  10                  15

Ala Pro Pro Val Pro Arg Arg Glu Arg Gly Gly Arg Gly Gly
                20                  25                  30

Arg Gly Pro Gly Glu Pro Gly Gly Arg Gly Arg Ala Gly Gly Ala
                35                  40                  45

Glu Gly Arg Gly Val Lys Cys Val Leu Val Gly Asp Gly Ala Val
                50                  55                  60

Gly Lys Thr Ser Leu Val Val Ser Tyr Thr Thr Asn Gly Tyr Pro
                65                  70                  75

Thr Glu Tyr Ile Pro Thr Ala Phe Asp Asn Phe Ser Ala Val Val
                80                  85                  90

Ser Val Asp Gly Arg Pro Val Arg Leu Gln Leu Cys Asp Thr Ala
                95                 100                 105

Gly Gln Asp Glu Phe Asp Lys Leu Arg Pro Leu Cys Tyr Thr Asn
               110                 115                 120

Thr Asp Ile Phe Leu Leu Cys Phe Ser Val Val Ser Pro Ser Ser
               125                 130                 135

Phe Gln Asn Val Ser Glu Lys Trp Val Pro Glu Ile Arg Cys His
               140                 145                 150

Cys Pro Lys Ala Pro Ile Ile Leu Val Gly Thr Gln Ser Asp Leu
               155                 160                 165

Arg Glu Asp Val Lys Val Leu Ile Glu Leu Asp Lys Cys Lys Glu
               170                 175                 180

Lys Pro Val Pro Glu Glu Ala Ala Lys Leu Cys Ala Glu Glu Ile
               185                 190                 195

Lys Ala Ala Ser Tyr Ile Glu Cys Ser Ala Leu Thr Gln Lys Asn
               200                 205                 210

Leu Lys Glu Val Phe Asp Ala Ala Ile Val Ala Gly Ile Gln Tyr
               215                 220                 225

Ser Asp Thr Gln Gln Gln Pro Lys Lys Ser Lys Ser Arg Thr Pro
               230                 235                 240

Asp Lys Met Lys Asn Leu Ser Lys Ser Trp Trp Lys Lys Tyr Cys
               245                 250                 255

Cys Phe Val
       258
```

<210> SEQ ID NO 4

<211> LENGTH: 2251
<212> TYPE: DNA
<213> ORGANISM: Mouse

<400> SEQUENCE: 4

| | |
|---|---|
| atggccccgc agcaaggccg gccggcgctg cccgcccgct gcgagccgcc | 50 |
| ggcggcgccg ccggtaccgc ctcgccgaga gcgcggggggg cgcggggcgc | 100 |
| gcgggcccgg ggtgtccggg ggtcgggggc gcgcgggcgc cgccgaggga | 150 |
| cgcggcgtca agtgcgtgct ggtcggcgac ggcgcggtgg gcaagaccag | 200 |
| cctggtggtc agctacacca ctaacggcta ccccaccgag tacatcccta | 250 |
| cggccttcga caacttctcg gccgtggtgt ctgtagatgg gcggcctgtg | 300 |
| agactccagc tctgtgacac tgcaggacag gatgagtttg acaagctgag | 350 |
| gcccctctgc tacaccaaca cagacatctt cctgctgtgc ttcagcgtgg | 400 |
| tgagccccac atccttccag aacgtgggcg agaagtgggt tccagagatt | 450 |
| cgacgtcact gcccaaaggc ccccatcatc ctggtcggga cacagtcgga | 500 |
| cctcagggag gacgtcaaag tgctcataga actggacaag tgcaaagaga | 550 |
| agccggtgcc tgaagaggcg gcgaagctgt gcgcggagga agtcaaagct | 600 |
| gtctcctaca tcgagtgctc agcgttgact cagaaaaacc tcaaagaggt | 650 |
| tttcgacgcc gccattgttg ctggtatcca gcactcagac tcccagctac | 700 |
| agccaaagaa gtctaaaagc aggaccccgg ataaggtgcg ggacctgtcc | 750 |
| aagtcttggt ggaggaagta ttgctgcctg gcctgactct cgcaaatagc | 800 |
| aggtgtttaa gctgcaacag ctctttatgg acgaggctgt cataggatga | 850 |
| gccccaaagc accctcttct gcccttaact tcctgtgtgc gggagcttag | 900 |
| ggctgagatt catatgcaaa atacgttttt ttaaaaattg aaagttacat | 950 |
| tttttttctg ttaagtctgg aagctttgag ctgtagacct ccggattaat | 1000 |
| ttatattcca tatgaaaagg gctcttcaaa gcggggtgtc agcatgaagt | 1050 |
| tctgctgtgt tgtacaggac aaaggagaat gaatgggacc ttctcctgat | 1100 |
| taagggctac tgagggctca gtgcagggca cgtgtgcacc aggcttggtg | 1150 |
| agagtgagca agcgtgagct ttgaaaccac acgagccacc cccggttttg | 1200 |
| taagggcaaa gatctgaaac cagcaagggc cttctgctta cgaaacctcg | 1250 |
| agcccatccc ttctgtttac tcagattctc ttaggatttt aaaacaacca | 1300 |
| aacatcccac agcctactgg catagtgttg gcgaacagtg cacttgcttg | 1350 |
| ttacggtttt gttttgtttt tttaaatcac gtgaccagtt atattgctat | 1400 |
| gaaaatggtg gagatgcctc gtagaaggcg agtgctgggt gcacatgtga | 1450 |
| catttttcttc agggagcgac tcatggtgag accagagagg gctcttagct | 1500 |
| tgcaggactg gcttctgcag ggcatctgtg tcctgctgtt aaaagcagga | 1550 |
| ggaggtgctt gtctgggagc tttaagtgtg ctgggctcat atcgtcccgt | 1600 |
| tgcaaggaa ttgggccacc ttgagaggcc atagttgatg gctatgggac | 1650 |
| acacacacac ttttttcctta agtccaccaa aatgcctgcc tgtacacaca | 1700 |
| cacacacaca cacacacaca cacacacaca cacactggct ggtttgctga | 1750 |
| tggaacccctt agaccaccct cccaccccca ccctcccca agcatggctg | 1800 |
| caagtgtcag ggcaccacac cttcctcttc ttgacatttc tttgaacaga | 1850 |

```
catcattttg taggatctta atttatacat tttttttcagg tcataaaatg      1900 tgggatgaac atactttgaa ccccagtgcc ttcagggtcc attgactagg      1950
gaggcactgt cttagggggac aggtatgtgc aaggccttac ccaccagtgg     2000
cttctcgctg caggtcatgt tgtggcact tgttctttaa ggtgagggtc       2050
ttatgaccga ctgttctgag acagccctgt gtcaggcaag ctctttcaca      2100
gggttgtagg tatttccaag acgccatagg aaccagacag tgaatcatag      2150
ctatcagttt gctgtgggca aggaacctct ttttggccac ctggtaacaa      2200
aattttatgt ctgtaaattt tttcttgcta tttaaaaaaa aaaaaaaaaa      2250
a                                                           2251

<210> SEQ ID NO 5
<211> LENGTH: 2251
<212> TYPE: DNA
<213> ORGANISM: Mouse

<400> SEQUENCE: 5
tttttttttt ttttttttaa atagcaagaa aaaatttaca gacataaaat        50
tttgttacca ggtggccaaa aagaggttcc ttgcccacag caaactgata       100
gctatgattc actgtctggt tcctatggcg tcttggaaat acctacaacc       150
ctgtgaaaga gcttgcctga cacagggctg tctcagaaca gtcggtcata       200
agaccctcac cttaaagaac aagtgccaca aacatgacct gcagcgagaa       250
gccactggtg ggtaaggcct tgcacatacc tgtcccctaa gacagtgcct       300
ccctagtcaa tggaccctga aggcactggg gttcaaagta tgttcatccc       350
acattttatg acctgaaaaa aatgtataaa ttaagatcct acaaaatgat       400
gtctgttcaa agaaatgtca agaagaggaa ggtgtggtgc cctgacactt       450
gcagccatgc ttggggaggg gtgggggtgg agggtggtc taagggttcc       500 atcagcaaac cagccagtgt gtgtgtgtgt gtgtgtgtgt gtgtgtgtgt       550
gtgtgtgtac aggcaggcat tttggtggac ttaaggaaaa agtgtgtgtg       600
tgtcccatag ccatcaacta tggcctctca aggtggccca attccttgca       650
aacgggacga tatgagccca gcacacttaa agctcccaga caagcacctc       700
ctcctgcttt taacagcagg acacagatgc cctgcagaag ccagtcctgc       750
aagctaagag ccctctctgg tctcaccatg agtcgctccc tgaagaaaat       800
gtcacatgtg cacccagcac tcgccttcta cgaggcatct ccaccatttt       850
catagcaata taactggtca cgtgatttaa aaaaacaaaa caaaaccgta       900
acaagcaagt gcactgttcg ccaacactat gccagtaggc tgtgggatgt       950
ttggttgttt taaaatccta agagaatctg agtaaacaga agggatgggc     1000
tcgaggtttc gtaagcagaa ggcccttgct ggtttcagat cttgtccctt     1050
acaaaaccgg gggtggctcg tgtggtttca aagctcacgc ttgctcactc     1100
tcaccaagcc tggtgcacac gtgccctgca ctgagccctc agtagcccctt    1150 aatcaggaga aggtcccatt cattctcctt tgtcctgtac aacacagcag     1200
aacttcatgc tgacaccccg ctttgaagag ccctttcat atggaatata      1250 aattaatccg gaggtctaca gctcaaagct tccagactta acagaaaaaa     1300
```

-continued

```
aatgtaactt tcaattttta aaaaaacgta ttttgcatat gaatctcagc        1350
cctaagctcc cgcacacagg aagttaaggg cagaagaggg tgctttgggg        1400
ctcatcctat gacagcctcg tccataaaga gctgttgcag cttaaacacc        1450
tgctatttgc gagagtcagg ccaggcagca atacttcctc caccaagact        1500
tggacaggtc ccgcacctta tccggggtcc tgcttttaga cttctttggc        1550
tgtagctggg agtctgagtg ctggataccca gcaacaatgg cggcgtcgaa       1600
aacctctttg aggtttttct gagtcaacgc tgagcactcg atgtaggaga        1650
cagctttgac ttcctccgcg cacagcttcg ccgcctcttc aggcaccggc        1700
ttctctttgc acttgtccag ttctatgagc actttgacgt cctccctgag        1750
gtccgactgt gtcccgacca ggatgatggg ggcctttggg cagtgacgtc        1800
gaatctctgg aacccacttc tcgcccacgt tctggaagga tgtggggctc        1850
accacgctga agcacagcag gaagatgtct gtgttggtgt agcagagggg        1900
cctcagcttg tcaaactcat cctgtcctgc agtgtcacag agctggagtc        1950
tcacaggccg cccatctaca gacaccacgg ccgagaagtt gtcgaaggcc        2000
gtagggatgt actcggtggg gtagccgtta gtggtgtagc tgaccaccag        2050
gctggtcttg cccaccgcgc cgtcgccgac cagcacgcac ttgacgccgc        2100
gtccctcggc gccgcccgcg cgcccccgac cccggacac  cccgggcccg        2150
cgcgccccgc gcccccgcg  ctctcggcga ggcggtaccg gcggcgccgc        2200
cggcggctcg cagcgggcgg gcagcgccgg ccggccttgc tgcggggcca        2250
t                                                            2251
```

<210> SEQ ID NO 6
<211> LENGTH: 261
<212> TYPE: PRT
<213> ORGANISM: Mouse

<400> SEQUENCE: 6

Met Ala Pro Gln Gln Gly Arg Pro Ala Leu Pro Ala Arg Cys Glu
 1               5                  10                  15

Pro Pro Ala Ala Pro Val Pro Pro Arg Arg Glu Arg Gly Gly
             20                  25                  30

Arg Gly Ala Arg Gly Pro Gly Val Ser Gly Arg Gly Arg Ala
         35                  40                  45

Gly Gly Ala Glu Gly Arg Gly Val Lys Cys Val Leu Val Asp
     50                  55                  60

Gly Ala Val Gly Lys Thr Ser Leu Val Val Ser Tyr Thr Thr Asn
 65                  70                  75

Gly Tyr Pro Thr Glu Tyr Ile Pro Thr Ala Phe Asp Asn Phe Ser
             80                  85                  90

Ala Val Val Ser Val Asp Gly Arg Pro Val Arg Leu Gln Leu Cys
             95                 100                 105

Asp Thr Ala Gly Gln Asp Glu Phe Asp Lys Leu Arg Pro Leu Cys
        110                 115                 120

Tyr Thr Asn Thr Asp Ile Phe Leu Leu Cys Phe Ser Val Val Ser
        125                 130                 135

Pro Thr Ser Phe Gln Asn Val Gly Glu Lys Trp Val Pro Glu Ile
        140                 145                 150

Arg Arg His Cys Pro Lys Ala Pro Ile Ile Leu Val Gly Thr Gln

```
                    155                 160                 165
Ser Asp Leu Arg Glu Asp Val Lys Val Leu Ile Glu Leu Asp Lys
                170                 175                 180

Cys Lys Glu Lys Pro Val Pro Glu Ala Ala Lys Leu Cys Ala
            185                 190                 195

Glu Glu Val Lys Ala Val Ser Tyr Ile Glu Cys Ser Ala Leu Thr
            200                 205                 210

Gln Lys Asn Leu Lys Glu Val Phe Asp Ala Ala Ile Val Ala Gly
            215                 220                 225

Ile Gln His Ser Asp Ser Gln Leu Gln Pro Lys Lys Ser Lys Ser
            230                 235                 240

Arg Thr Pro Asp Lys Val Arg Asp Leu Ser Lys Ser Trp Trp Arg
            245                 250                 255

Lys Tyr Cys Cys Leu Ala
            260 261

<210> SEQ ID NO 7
<211> LENGTH: 2822
<212> TYPE: DNA
<213> ORGANISM: Mouse

<400> SEQUENCE: 7
cccacgcgtc cgctgaatgt atgttggtta gaaagtagcc tttctgcttc            50
ctgcccatgg ccagttctcc accctctctt tggtgttctt tgtggggagg           100
gcactgtggt ttgtcgcagc cctggacttc gagaggctcc cagaacccag           150
gatcaccagc ctcctgtctg tttgcttcac tcctttccca gggaggactt           200
gggactgtcc tgtctgacag gacggatctg agttcccgaa gcaaaccagc           250
tcaccacata gatagctagt ttaaacaatg ttttaaaata agggcacctc           300
tgtttcaaaa gtgacatctg ctgtgttgtt ttcgaggcct gatactctta           350
caaggtttga aaaaaaatgt gtgtatccat tcatgggctt ggtagccttc           400
tggtcacctc agtcctgtgg ctcttaactt attgcccaac aatattcatt           450 tccccctcagc tacaatgaat tgcaagcaaa agatgttgaa aaaaagcact          500
aatttagttt aaaatgtcac ttttggtttt ttattctaca aaaaccatga           550
agttctctct ctctctctct ctctctctta gttgttaaat cagattatgt           600
tctttttttg ttttgtttt tagtgattca tgtttatgag cagagtggag            650
tttaacaatc ctagctttaa aaaaaaccta tttaatgtaa gatattctac           700
gcatccttca gatattttgt atatccccta tggcctttag tctgtacttt           750
taatgtacat atttctgtct tgtgtgattt gtagatttca ctggttaaaa           800
gagagaacat tgaaaggctt atgccaagtg gaagatagaa tataaaataa           850
aaatgttact tgtatattgg taagaggttt cagttgtcct tcagctaatt           900
catgtagaga aatattttag ttgaagccac aagagacagc ttagggcagt           950
tatgtgttca aataacagaa gaacagactt ttttttttttt ttaaaccaaa         1000 cccaaactgt tgggaaacct caatagagct ctatatgtat tggaacaaaa         1050
gtggaattct cttctcctat atatgttcct tcaaaaagag agagagaatc          1100
aagcagatgg cttaaagctg gtcacaggat tgctcacatt ctttttggcat        1150 tatgcatgcg acttaattgt ttgagagtgt gttgctattg taacatccca         1200
```

| | |
|---|---|
| gagatgaatc aaaaaggctc accctctcac ccaggagcag cttttcagct | 1250 |
| tatatacaca tgcatgtaca tgtgtgtgat atgcatgtgt gcatgcatgt | 1300 |
| ttgtattttt gtgcttgcca ctataactat tgcacctctc tattcggttt | 1350 |
| gactgaagag gggtcttgtg ggacatctct gtgtcccagt ctttatggga | 1400 |
| agaaagcaag ggtctgcaga gaacaggaac taaagaatcc ctgtgtgatg | 1450 |
| tgcaattaat agaaggcctc ctgctttctg gaaatgtaga ccagaatctg | 1500 |
| gccaggactg tagactgata cattatctgg tcctttgcct ttttcttttc | 1550 |
| cctccctgcc cctcccctc ttgctttatg gataaccttg taacatattg | 1600 |
| aaacctttaa aggaaaccaa gaatgcatta ttacacacac acacacacac | 1650 |
| acacacacac acacacacac acacacacta cagtagacca acatatagag | 1700 |
| tgtttaaaat agcttttctg ggcaaattca acaacttgt ggctctagga | 1750 |
| cgcacatctg tttccgtttt tcttcagttg tatattgacc agtattcttt | 1800 |
| attgctaaaa catatactcg gggtagcaat gtcagcatct tttcccttcc | 1850 |
| catcctggag agcattcaag accttcccag tacaggaaca tcaatgaagc | 1900 |
| atttatatac aggcggtggc aagcagaacc acatccaaaa tggtcagtgt | 1950 |
| cgggctctag ggcaaggcta tcttgttcca gtcctgtttc tttgtgctcc | 2000 |
| tgacctttgg ggctgccact tcccaggacg accactgcct gcccacactg | 2050 |
| tcccccctc cccccggggg gattttccca atagccagtt cccatgtgtc | 2100 |
| tttttctgca acggtattca agccaatgga accttcagat agggcccaag | 2150 |
| agcaggatga cacaacctgt ggacaagagc tatattaact tgatcactag | 2200 |
| tatgagctaa tattaacatg atcacccatg aaaggcgcct gcaagagctg | 2250 |
| tttagtctga aatataggta gagagcgggg atggcaaggt tgcttgtaac | 2300 |
| ttctggtaca tgttgaatgc acacacgcat ggaggcaagc tctaaatcac | 2350 |
| tgcactgtta ctgtaaagca tactttaaaa atatttattg ttttgaaaag | 2400 |
| cattttctag tcttccctct cttggtggag ctgtaaacaa gatggcatgt | 2450 |
| tgtgaaggtt caagatgatt ttttttaaa tcgcagaaac atttagacac | 2500 |
| ctaagaacta aaacttataa aagggatctt tgaatttgcc tgttaacatg | 2550 |
| gattaatgtt tacacttaca gctgatgatt ggacggtgtt ttatgttagg | 2600 |
| gaaatgcctt gttaacgaac ttcatgaagc agatgtaatt aaaggttgat | 2650 |
| gtgagccaat ctagaaggtt gaacagtgtt ttcaaagaac ggagagactt | 2700 |
| acattttaga ccaatctta tacattttgc tgagctagaa aggagataaa | 2750 |
| gattatttat ttttgttcat atcttgtact tttctattaa aatcatttta | 2800 |
| tgaaawmmaa aaaaaaaaaa aa | 2822 |

<210> SEQ ID NO 8
<211> LENGTH: 727
<212> TYPE: DNA
<213> ORGANISM: Mouse

<400> SEQUENCE: 8

| | |
|---|---|
| cccacgcgtc cgcatatgtc tcctttgtga ggatcaacag ctcgctggca | 50 |
| gtggcggctt acgaggatgg gatccttaac atttgggacc tgagaaccgg | 100 |
| aaggttccct atctttcgtt ttgagcatga cgcaagaata caagcccttg | 150 |

```
cgctgagcca agaaaagccc attgttgcca cggcttctgc ttttgacgtt      200
gtgatgttgt accccaacga ggaggggcat tggcatgtgg cctcggagtt      250
tgaagttcag aagctggttg actaccttga aatagttccg aatactggga      300
ggtaccctgt ggcaatagcc acagccgggg atctggtgta cctgctgaag      350
gccgacgact cagccagaac ccttcattat gtcaatggcc agcctgccac      400
atgtctggat gtctcagcca gccaggttgc ctttggagtg aagagtctag      450
gatgggtgta tgaaggaaac aagatcctgg tgtacagcct ggaagcagag      500
cgctgcctct cgaagctggg caatgcactt ggagacttta cctgtgtcaa      550
catccgggat agccctccca acctcatggt cagcggcaac atggacagga      600
gagtgaggat tcatgacctc cgcagcgata agatcgccct gtcgctgtct      650
gcccatcagc tgggggtgtc cgcaattcca aatggataac tggaaaggtt      700
gtcagtggag gccaggaggg gtggtgt                               727
```

```
<210> SEQ ID NO 9
<211> LENGTH: 2526
<212> TYPE: DNA
<213> ORGANISM: Mouse

<400> SEQUENCE: 9
cccacgcgtc cgcatatgtc tcctttgtga ggatcaacag ctcgctggca       50
gtggcggctt acgaggatgg gatccttaac atttgggacc tgagaaccgg      100
aaggttccct atctttcgtt ttgagcatga cgcaagaata caagcccttg      150
cgctgagcca agaaaagccc attgttgcca cggcttctgc ttttgacgtt      200
gtgatgttgt accccaacga ggaggggcat tggcatgtgg cctcggagtt      250
tgaagttcag aagctggttg actaccttga aatagttccg aatactggga      300
ggtaccctgt ggcaatagcc acagccgggg atctggtgta cctgctgaag      350
gccgacgact cagccagaac ccttcattat gtcaatggcc agcctgccac      400
atgtctggat gtctcagcca gccaggttgc ctttggagtg aagagtctag      450
gatgggtgta tgaaggaaac aagatcctgg tgtacagcct ggaagcagag      500
cgctgcctct cgaagctggg caatgcactt ggagacttta cctgtgtcaa      550
catccgggat agccctccca acctcatggt cagcggcaac atggacagga      600
gagtgaggat ccatgacctc cgcagcgata agatcgccct gtcgctgtct      650
gcccatcagc tgggggtgtc cgcagtccag atggatgact ggaaggttgt      700
cagtggaggc gaggaggggc tggtgtctgt gtgggattac cgcatgaacc      750
agaagctgtg ggaagtgcac tccaggcacc ctgtgcgcta tctctccttc      800
aatagccaca gcctcatcac tgccaacgtg ccctacgaga aggtgctgcg      850
aaactccgac ctcgacaact ttgcctgtca caggagacat cgtggcctga      900
tccatgccta tgaatttgct gtggaccagc tggcctttca gagccccctt      950
cctgtctgcc gcttacccg tgacatcatg gctggataca gctatgacct     1000
cgcactgtct ttccccccatg acagtattta gggtgtcacc tcatgtagac     1050
gtggaaaggg cagttttaca aatgttagag ttggagagag gctctgcagc     1100
acatggtggg agtttgggga cagtgtcctg tatgactgtg gccacacagc     1150
```

-continued

| | |
|---|---|
| cctgttgccc tgtacagaac cagactccat tgctgccttt ctcctcctcc | 1200 |
| tcctcctcct caggctttgg taggactggc tgatgactca gagttaacct | 1250 |
| ttccaggggt ggctcctccc cctcagccta tggcagcagt gacaccccc | 1300 |
| ctcgttccat aggccaggga cacagggcct tcacttgcac tgtctcctgg | 1350 |
| gtgtggtgct gagggtggaa ccagaatctc acacgcatag gcaagcgtca | 1400 |
| gcctccaagc tgcctcccca gctgtcagcc tccccagctg tctcctccag | 1450 |
| gcaccctcca gtgcagcccc tcctctggga ttcaccgt tgataattat | 1500 |
| agggccacct tacctgtagg agctgttctg tcctgtacat gtgctatgaa | 1550 |
| ggagacagcc atccttcctg cagagggaaa gggtcattgc acagggatag | 1600 |
| ggtcagtctc caagcctagc cggtggtgtc tcttcctgac aaacgcagcc | 1650 |
| atagctcacc cactctgcct tcagagtgtc atggacaaat ccacacatag | 1700 |
| tggccaggag acccagtcag agctcttcag aatccccaca gaccaggcac | 1750 |
| ctaacacacc tgcacagagg ccaccaggtc tcaggagaca agttcctct | 1800 |
| cccagggaat accagctcaa aaacaagtg gctggcaaa ctccacattg | 1850 |
| ggtctgccga gagcaagaaa aagagggggg gtgggggagc tccatggggt | 1900 |
| ggatcccagg ctggcagcag gaaggtgctg gaaggcctga gagggtgtgc | 1950 |
| agtgccctcc ccgagccctg gtggtctcct cctgtgtgct gggatggagt | 2000 |
| ctagtggggtt tgtggcatga tctcagatct tggcattgag gcctctcccc | 2050 |
| atgcacaagt gcccagggga gctcacctcc ctcttgctgg gctggcgccc | 2100 |
| cctgctggcc tggtcttgct gtgtcctcac tcgagcattc ccagtcctaa | 2150 |
| gctgtccact ggagacattt ctgtcagaga aattggctgt gcggtcagct | 2200 |
| cctttctggg cttcgcagcc atgaaaggcc actgaagagc agaggtgact | 2250 |
| agagtagttt caagcataca tgcccttcta gcccccaatc cctgccccct | 2300 |
| accccacag agcatctgtc ctcgctggct cctgccactg cacctgctcc | 2350 |
| cagggtgggg gacaggctgg ctccctgtgc tgcctctgaa gccagaagac | 2400 |
| accaggacac agccctggga gccaggggtg gtcacacatc tgcagcttgc | 2450 |
| cttttgcctt aagcggccac ttctgctctg ttattaaagg ttctacactg | 2500 |
| aaaaaaaaaa aaaaaaaaaa aaaaaa | 2526 |

<210> SEQ ID NO 10
<211> LENGTH: 2526
<212> TYPE: DNA
<213> ORGANISM: Mouse

<400> SEQUENCE: 10

| | |
|---|---|
| tttttttttt tttttttttt tttttcagt gtagaacctt taataacaga | 50 |
| gcagaagtgg ccgcttaagg caaaaggcaa gctgcagatg tgtgaccacc | 100 |
| cctggctccc agggctgtgt cctggtgtct tctggcttca gaggcagcac | 150 |
| agggagccag cctgtccccc accctgggag caggtgcagt ggcaggagcc | 200 |
| agcgaggaca gatgctctgt gggggtaggg ggcagggatt gggggctaga | 250 |
| agggcatgta tgcttgaaac tactctagtc acctctgctc ttcagtggcc | 300 |
| tttcatggct gcgaagccca gaaggagct gaccgcacag ccaatttctc | 350 |
| tgacagaaat gtctccagtg gacagcttag gactgggaat gctcgagtga | 400 |

-continued

| | |
|---|---|
| ggacacagca agaccaggcc agcagggggc gccagcccag caagagggag | 450 |
| gtgagctccc ctgggcactt gtgcatgggg agaggcctca atgccaagat | 500 |
| ctgagatcat gccacaaacc cactagactc catcccagca cacaggagga | 550 |
| gaccaccagg gctcggggag ggcactgcac accctctcag gccttccagc | 600 |
| accttcctgc tgccagcctg ggatccaccc catggagctc cccaccccc | 650 |
| ctctttttc ttgctctcgg cagacccaat gtggagtttg ccagcccact | 700 |
| tgttttttga gctggtattc cctgggagag aactttgtc tcctgagacc | 750 |
| tggtggcctc tgtgcaggtg tgttaggtgc ctggtctgtg gggattctga | 800 |
| agagctctga ctgggtctcc tggccactat gtgtggattt gtccatgaca | 850 |
| ctctgaaggc agagtgggtg agctatggct gcgtttgtca ggaagagaca | 900 |
| ccaccggcta ggcttggaga ctgaccctat ccctgtgcaa tgacccttc | 950 |
| cctctgcagg aaggatggct gtctccttca tagcacatgt acaggacaga | 1000 |
| acagctccta caggtaaggt ggccctataa ttatcaacgg tgtgaatccc | 1050 |
| agaggagggg ctgcactgga gggtgcctgg aggagacagc tggggaggct | 1100 |
| gacagctggg gaggcagctt ggaggctgac gcttgcctat gcgtgtgaga | 1150 |
| ttctggttcc accctcagca ccacacccag gagacagtgc aagtgaaggc | 1200 |
| cctgtgtccc tggcctatgg aacgagggg ggtgtcactg ctgccatagg | 1250 |
| ctgaggggga ggagccaccc ctggaaaggt taactctgag tcatcagcca | 1300 |
| gtcctaccaa agcctgagga ggaggaggag gaggagaaag gcagcaatgg | 1350 |
| agtctggttc tgtacagggc aacagggctg tgtggccaca gtcatacagg | 1400 |
| acactgtccc caaactccca ccatgtgctg cagagcctct ctccaactct | 1450 |
| aacatttgta aaactgccct ttccacgtct acatgaggtg acaccctaaa | 1500 |
| tactgtcatg ggggaaagac agtgcgaggt catagctgta tccagccatg | 1550 |
| atgtcacggg gtaagcggca gacaggaagg gggctctgaa aggccagctg | 1600 |
| gtccacagca aattcatagg catggatcag gccacgatgt ctcctgtgac | 1650 |
| aggcaaagtt gtcgaggtcg gagtttcgca gcaccttctc gtagggcacg | 1700 |
| ttggcagtga tgaggctgtg gctattgaag gagagatagc gcacagggtg | 1750 |
| cctggagtgc acttcccaca gcttctggtt catgcggtaa tcccacacag | 1800 |
| acaccagccc ctcctcgcct ccactgacaa ccttccagtc atccatctgg | 1850 |
| actgcggaca ccccccagctg atgggcagac agcgacaggg cgatcttatc | 1900 |
| gctgcggagg tcatggatcc tcactctcct gtccatgttg ccgctgacca | 1950 |
| tgaggttggg agggctatcc cggatgttga cacaggtaaa gtctccaagt | 2000 |
| gcattgccca gcttcgagag gcagcgctct gcttccaggc tgtacaccag | 2050 |
| gatcttgttt ccttcataca cccatcctag actcttcact ccaaaggcaa | 2100 |
| cctggctggc tgagacatcc agacatgtgg caggctggcc attgacataa | 2150 |
| tgaagggttc tggctgagtc gtcggccttc agcaggtaca ccagatcccc | 2200 |
| ggctgtggct attgccacag ggtacctccc agtattcgga actatttcaa | 2250 |
| ggtagtcaac cagcttctga acttcaaact ccgaggccac atgccaatgc | 2300 |
| ccctcctcgt tggggtacaa catcacaacg tcaaaagcag aagccgtggc | 2350 |

```
aacaatgggc ttttcttggc tcagcgcaag ggcttgtatt cttgcgtcat         2400
gctcaaaacg aaagataggg aaccttccgg ttctcaggtc ccaaatgtta         2450
aggatcccat cctcgtaagc cgccactgcc agcgagctgt tgatcctcac         2500
aaaggagaca tatgcggacg cgtggg                                   2526

<210> SEQ ID NO 11
<211> LENGTH: 204
<212> TYPE: DNA
<213> ORGANISM: Mouse

<400> SEQUENCE: 11
cagagggtgg gtgggaaaga gtgaattatt taattttaaa tgttataata          50
aagccaatgt agttgagacc aaggaaatga gcattgagaa cacaaacttg         100
aagtctggtg ccagggttgt tggacctcac accctgtctc tgagccaccc         150
ggaagtgaca taaaggacgc tgtgtgatca agttctggac acttttctgg         200
gatg                                                           204

<210> SEQ ID NO 12
<211> LENGTH: 2224
<212> TYPE: DNA
<213> ORGANISM: Mouse

<400> SEQUENCE: 12
cccacgcgtc cgcgcggtgg gcaagaccag cctggtggtc agctacacca          50
ctaacggcta ccccaccgag tacatcccta cggccttcga caacttctcg         100
gccgtggtgt ctgtagatgg gcggcctgtg agactccagc tctgtgacac         150
tgcaggacag gatgagtttg acaagctgag gcccctctgc tacaccaaca         200
cagacatctt cctgctgtgc ttcagcgtgg tgagccccac atccttccag         250
aacgtgggcg agaagtgggt tccagagatt cgacgtcact gcccaaaggc         300
ccccatcatc ctggtcggga cacagtcgga cctcagggag gacgtcaaag         350
tgctcataga actggcttct gcagggcatc tgtgtcctgc tgttaaaagc         400
aggaggaggt gcttgtctgg gagctttaag tgtgctgggc tcatatcgtc         450
ccgtttgcaa ggaattgggc caccttgaga ggccatagtt gatggctatg         500
ggacacacac acacttttc cttaagtcca ccaaaatgcc tgcctgtaca          550
cacacacaca cacacacaca cacacacaca cacacacact ggctggtttg         600
ctgatggaac ccttagacca ccctcccacc ccaccccctc cccaagcatg         650
gctgcaagtg tcagggcacc acaccttcct cttcttgaca tttctttgaa         700
cagacatcat tttgtaggat cttaatttat acatttttt caggtcataa          750 aatgtgggat gaacatactt tgaaccccag tgccttcagg gtccattgac         800
tagggaggca ctgtcttagg ggacaggtat gtgcaaggcc ttacccacca         850
gtggcttctc gctgcaggtc atgtttgtgg cacttgttct ttaaggtgag         900
ggtcttatga ccgactgttc tgagacagcc ctgtgtcagg caagctcttt         950
cacagggttg taggtatttc caagacgcca taggaaccag acagtgaatc        1000
atagctatca gtttgctgtg ggcaaggaac ctctttttgg ccacctggta        1050
acaaaatttt atgtctgtaa attttttctt gctatttaaa aaaaaaaat         1100 caatcttacg ttttctgta ggaaaaaaaa aaacaagtaa aagaacaggc          1150
```

| | |
|---|---|
| catatttcag gtcaaaggct tcttcctgct ggtaaatggg actgaagact | 1200 |
| ttcttacatc attattaaaa ggctaattgc tgaaccacta gagtatatga | 1250 |
| actgtttgtg aatgatatta gccatagtct cctgaggtgt ttccttgtgg | 1300 |
| cctgagtggt aacattgttt tgcttatgga gatgctgtaa ctgacctagt | 1350 |
| gactcagctt atcctattgt gcatggctgt ctggaaagcc agcgtacaag | 1400 |
| tggggctttg cctgccctgt gtacagaggg tgggtgggaa agagtgaatt | 1450 |
| atttaatttt aaatgttata ataaagccaa tgtagttgag accaaggaaa | 1500 |
| tgagcattga gaacacaaac ttgaagtctg gtgccagggt tgttggacct | 1550 |
| cacaccctgt ctctgagcca cccggaagtg acataaagga cgctgtgtga | 1600 |
| tcaagttctg gacactttc tgggatgcgt accactggac tatttatgtc | 1650 |
| acaaatctag tgggttgacg ctgccctgca agttttcaat gtccctgcat | 1700 |
| cctatgaagt cataatgtct gactgtactg gaggttttcc tgcattttt | 1750 |
| acttttcgaa aatagaggtt tgggctgaga attctaaacg catgtgcctg | 1800 |
| ggtgggacgt caagtcaggg ttctcatcaa agctgagaag tggctggaat | 1850 |
| gttcagcttg gtgtctgggg aggatcctgt gagctatgta gagaggtggc | 1900 |
| tcttcagcct gactcagtgt gggctgaacg aagtacctgc agaacacacg | 1950 |
| gtagcaggct ccaaaatcgt cacctcaagc atgcgtgcaa gcaaacttcc | 2000 |
| gagaactccg ttttctgctc ggcagacgtg tgagcagcta cccagaagtc | 2050 |
| tcaagccaaa aggggagcct cgctcgctgg ctcctctgca ggtgccttat | 2100 |
| cgacctgtgc tcttctcttt tcccgtgtca aagatgttgg acaggatctt | 2150 |
| gtacttgaaa catactacaa atgagttact atgaaataaa ttctgacctg | 2200 |
| tggaccgaaa aaaaaaaaaa aaaa | 2224 |

<210> SEQ ID NO 13
<211> LENGTH: 2004
<212> TYPE: DNA
<213> ORGANISM: Mouse

<400> SEQUENCE: 13

| | |
|---|---|
| cccacgcgtc cgcacgtgac cagttatatt gctatgaaaa tggtggagat | 50 |
| gcctcgtaga aggcgagtgc tgggtgcaca tgtgacattt tcttcaggga | 100 |
| gcgactcatg gtgagaccag agagggctct tagcttgcag gactggcttc | 150 |
| tgcagggcat ctgtgtcctg ctgttaaaag caggaggagg tgcttgtctg | 200 |
| ggagctttaa gtgtgctggg ctcatatcgt cccgtttgca aggaattggg | 250 |
| ccaccttgag aggccatagt tgatggctat gggacacaca cacactttt | 300 |
| ccttaagtcc accaaaatgc ctgcctgtac acacacacac acacacac | 350 |
| acacacacac acacacacac tggctggttt gctgatggaa cccttagacc | 400 |
| accctcccac ccccacccct cccaagcat ggctgcaagt gtcagggcac | 450 |
| cacaccttcc tcttcttgac atttctttga acagacatca ttttgtagga | 500 |
| tcttaatttta tacatttttt tcaggtcata aaatgtggga tgaacatact | 550 |
| ttgaaccca gtgccttcag ggtccattga ctagggaggc actgtctag | 600 |
| gggacaggta tgtgcaaggc cttacccacc agtggcttct cgctgcaggt | 650 |

-continued

| | |
|---|---|
| catgtttgtg gcacttgttc tttaaggtga gggtcttatg accgactgtt | 700 |
| ctgagacagc cctgtgtcag gcaagctctt tcacagggtt gtaggtattt | 750 |
| ccaagacgcc ataggaacca gacagtgaat catagctatc agtttgctgt | 800 |
| gggcaaggaa cctcttttg gccacctggt aacaaaattt tatgtctgta | 850 |
| aattttttct tgctatttaa aaaaaaaaaa tcaatcttac gttttctgt | 900 |
| aggaaaaaaa aaacaagta aagaacagg ccatatttca ggtcaaaggc | 950 |
| ttcttcctgc tggtaaatgg gactgaagac tttcttacat cattattaaa | 1000 |
| aggctaattg ctgaaccact agagtatatg aactgtttgt gaatgatatt | 1050 |
| agccatagtc tcctgaggtg tttccttgtg gcctgagtgg taacattgtt | 1100 |
| ttgcttatgg agatgctgta actgacctag tgactcagct tatcctattg | 1150 |
| tgcatggctg tctggaaagc cagcgtacaa gtggggcttt gcctgccctg | 1200 |
| tgtacagagt gtgggtggga aagagtgaat tatttaattt taaatgttat | 1250 |
| aataaagcca atgtagttga gaccaaggaa atgagcattg agaacacaaa | 1300 |
| cttgaagtct ggtgccaggg ttgttggacc tcacaccctg tctctgagcc | 1350 |
| acccggaagt gacataaagg acgctgtgtg atcaagttct ggacactttt | 1400 |
| ctgggatgcg taccactgga ctatttatgt cacaaatcta gtgggttgac | 1450 |
| gctgccctgc aagttttcaa tgtccctgca tcctatgaag tcataatgtc | 1500 |
| tgactgtact ggaggttttc ctgcattttt tacttttcga aaatagaggt | 1550 |
| ttgggctgag aattctaaac gcatgtgcct gggtgggacg tcaagtcagg | 1600 |
| gttctcatca aagctgagaa gtggctggaa tgttcagctt ggtgtctggg | 1650 |
| gaggatcctg tgagctatgt agagaggtgg ctcttcagcc tgactcagtg | 1700 |
| tgggctgaac gaagtacctg cagaacacac ggtagcaggc tccaaaatcg | 1750 |
| tcacctcaag catgcgtgca agcaaacttc cgagaactcc gttttctgct | 1800 |
| cggcagacgt gtgagcagct acccagaagt ctcaagccaa aaggggagcc | 1850 |
| tcgctcgctg gctcctctgc aggtgcctta tcgacctgtg ctcttctctt | 1900 |
| ttcccgtgtc aaagatgttg acaggatct tgtacttgaa acatactaca | 1950 |
| aatgagttac tatgaaataa attctgacct gtggaccgaa aaaaaaaaa | 2000 |
| aaaa | 2004 |

<210> SEQ ID NO 14
<211> LENGTH: 1016
<212> TYPE: DNA
<213> ORGANISM: Mouse

<400> SEQUENCE: 14

| | |
|---|---|
| cccacgcgtc cgcgccgagg gacgcggcgt caagtgcgtg ctggtcggcg | 50 |
| acggcgcggt gggcaagacc agcctggtgg tcagctacac cactaacggc | 100 |
| taccccaccg agtacatccc tacgccttc gacaacttct cggccgtggt | 150 |
| gtctgtagat gggcggcctg tgagactcca gctctgtgac actgcaggac | 200 |
| aggatgagtt tgacaagctg aggcccctct gctacaccaa cacagacatc | 250 |
| ttcctgctgt gcttcagcgt ggtgagcccc acatccttcc agaacgtggg | 300 |
| cgagaagtgg gttccagaga ttcgacgtca ctgcccaaag gccccccatca | 350 |
| tcctggtcgg gacacagtcg gacctcaggg aggacgtcaa agtgctcata | 400 |

| | |
|---|---|
| gaactggaca agtgcaaaga gaagccggtg cctgaagagg cggcgaagct | 450 |
| gtgcgcggag gaagtcaaag ctgtctccta catcgagtgc tcagcgttga | 500 |
| ctcagaaaaa cctcaaagag gttttcgacg ccgccattgt tgctggtatc | 550 |
| cagcactcag actcccagct acagccaaag aagtctaaaa gcaggacccc | 600 |
| ggataaggtg cgggacctgt ccaagtcttg gtggaggaag tattgctgcc | 650 |
| tggcctgact ctcgcaaata gcaggtgttt aagctgcaac agctctttat | 700 |
| ggacgaggct gtcataggat gagccccaaa gcaccctctt ctgcccttaa | 750 |
| cttcctgtgt gcgggagctt agggctgaga ttcatatgca aaatacgttt | 800 |
| ttttaaaaat tgaaagttac attttttttc tgttaagtct ggaagctttg | 850 |
| agctgttaga cctccggatt aatttatatt ccatatgaaa agggctcttc | 900 |
| aaaagcgggg gtgtcagcat gaagttctgc tggtgtttgt acaggacaaa | 950 |
| ggagaatgaa tggggaacct tcctcctgaa ttaagggggct aactgaaggg | 1000 |
| ctcaattgca agggca | 1016 |

<210> SEQ ID NO 15
<211> LENGTH: 4075
<212> TYPE: DNA
<213> ORGANISM: Mouse

<400> SEQUENCE: 15

| | |
|---|---|
| cccacgcgtc cggcgcgagc ttagcagatc tccacttacc gaacatctag | 50 |
| agagtcgcgc cgcgcgccga cggagcggac atgggcagag cgatggtggc | 100 |
| caggctaggg ctggggttgc tgcttctggc actgctccta cccacgcaga | 150 |
| tttactgcaa ccaaacatct gttgcaccgt ttcccggtaa ccagaatatt | 200 |
| tctgcttccc caaatccaag taacgctacc accagagggg gtggcagctc | 250 |
| cctgcagtcc acagctggtc tcctgggctc tctctctctc tcttccacat | 300 |
| ctctactgtt agagactcag gccaggaaac gtctctactt ccccatcctc | 350 |
| tagacctacc ccaaatggca accacaagtc caatgtgatc aggaagaaac | 400 |
| aggtccacct cgaattggct gttaccatat ctcaacagaa aacacggaga | 450 |
| attcgaaatt cgacgggatt aaaggacgcg tgaaaggttt gagagaagag | 500 |
| agatgccgct attgaatctg ctggagtttt acatcccaag atgaagacag | 550 |
| cattcagaat tgatgtgatt tccttgaatg tggcttagga aaagtggaca | 600 |
| cttaaaactc tcacttgaaa ttgggcacag gtttgatgta gagataagga | 650 |
| cggggtgcgg aatggagacc cattttgtca ttgattcatc tgaccgataa | 700 |
| ggccatagtg cagttaggtg atattcgaaa gcttctttga tgctcttat | 750 |
| gtatatgttg gaaggaacta ccaggcgttg ctttaaattc ccaatgtgtt | 800 |
| gtttcgttac tactaattta ataccgtaag ctctaggtaa agttccatgt | 850 |
| tgttgaactc tgactgttct ctttggaatt gaacgttttg catcctcctc | 900 |
| ctgtggcttt aggtctgaca ttgtatttga cctttactag taattaacat | 950 |
| gtgccaggca atggtggatt ggaacccatc cccaagtcca gccaccactg | 1000 |
| aataaatctg atttcaaaag tcaaacagta gacatttccc attgtcgttt | 1050 |
| ctcactcacc acaagcacca aattcactag agtacactgg ttccagagag | 1100 |

```
cagaatcatg ttggccttgg ctaatttcaa aatgctgtct tttactttgg     1150
tatatgttga gggcttttc ataatttaaa gtgtgttctg ttagcaaggc     1200
aaaaattatg agtcttaatt ctacaggcaa atatgcaaag gagccaaaac     1250
tgtaaaccca gcatttggga tgtgaagact ggaagctaac tctcattgaa     1300
ttcacaaagt cttttataca atttctgtac atactttttt ttttttttaag    1350
agaaaaacaa acggtggatc agaatagcca cgtttggaat actttggtta     1400
tccattcata ttttagata gttattggtc ctgtgcctga aagggggctt      1450
ggttctaccg taagttttc caattccctt gatatacaca taccttctaa     1500
aacctagaca tttcctgaaa aaatcttttt gttcgcatgg tcacacactg     1550
atgcttaccc gtacagtagt cttgataacc agagtcattt tctccatctt     1600
tagaaacctt cctgggaaga aggagagctc acagacccga agctactgtg     1650
tgtgtgaatg aacactcccc ttgcctcaca cctgaatgct gtacatctat     1700
ttgattgtaa attgtgtttg tgtatttatg ctttgattca tagtaacttc     1750
tcatgttatg gaattgattt gcattgaaca caaactgtaa aaaaaaaaa     1800
aaaaagggcg gccgccgccc cgcgatggcc ccgcagcaag gccggccggc     1850
gctgcccgcc cgctgcgagc cgccggcggc gccgccggta ccgcctcgcc     1900
gagagcgcgg ggggcgcggg gcgcgcgggc ccggggtgtc cgggggtcgg     1950
gggcgcgcgg gcggcgccga gggacgcggc gtcaagtgcg tgctggtcgg     2000
cgacggcgcg gtgggcaaga ccagcctggt ggtcagctac accactaacg     2050
gctaccccac cgagtacatc cctacggcct tcgacaactt ctcggccgtg     2100
gtgtctgtag atgggcggcc tgtgagactc cagctctgtg acactgcagg     2150
acaggatgag tttgacaagc tgaggcccct ctgctacacc aacacagaca     2200
tcttcctgct gtgcttcagc gtggtgagcc ccacatcctt ccagaacgtg     2250
ggcgagaagt gggttccaga gattcgacgt cactgcccaa aggcccccat     2300
catcctggtc gggacacagt cggacctcag ggaggacgtc aaagtgctca     2350
tagaactgga caagtgcaaa gagaagccgg tgcctgaaga ggcggcgaag     2400
ctgtgcgcgg aggaagtcaa agctgtctcc tacatcgagt gctcagcgtt     2450
gactcagaaa aacctcaaag aggttttcga cgccgccatt gttgctggta     2500
tccagcactc agactcccag ctacagccaa agaagtctaa aagcaggacc     2550
ccggataagg tgcgggacct gtccaagtct tggtggagga agtattgctg     2600
cctggcctga ctctcgcaaa tagcaggtgt ttaagctgca acagctcttt     2650
atggacgagg ctgtcatagg atgagcccca agcaccctc ttctgccctt     2700
aacttcctgt gtgcgggagc ttagggctga gattcatatg caaaatacgt     2750
ttttttaaaa attgaaagtt acatttttt tctgttaagt ctggaagctt     2800
tgagctgtag acctccggat taatttatat tccatatgaa aagggctctt     2850
caaagcgggg tgtcagcatg aagttctgct gtgttgtaca ggacaaagga     2900
gaatgaatgg gaccttctcc tgattaaggg ctactgaggg ctcagtgcag     2950
ggcacgtgtg caccaggctt ggtgagagtg agcaagcgtg agctttgaaa     3000
ccacacgagc caccccggt tttgtaaggg caaagatctg aaaccagcaa     3050
gggccttctg cttacgaaac ctcgagccca tcccttctgt ttactcagat     3100
```

-continued

| | |
|---|---|
| tctcttagga ttttaaaaca accaaacatc ccacagccta ctggcatagt | 3150 |
| gttggcgaac agtgcacttg cttgttacgg ttttgttttg ttttttttaaa | 3200 |
| tcacgtgacc agttatattg ctatgaaaat ggtggagatg cctcgtagaa | 3250 |
| ggcgagtgct gggtgcacat gtgacatttt cttcagggag cgactcatgg | 3300 |
| tgagaccaga gagggctctt agcttgcagg actggcttct cagggcatc | 3350 |
| tgtgtcctgc tgttaaaagc aggaggaggt gcttgtctgg gagctttaag | 3400 |
| tgtgctgggc tcatatcgtc ccgtttgcaa ggaattgggc caccttgaga | 3450 |
| ggccatagtt gatggctatg ggacacacac acactttttc cttaagtcca | 3500 |
| ccaaaatgcc tgcctgtaca cacacacaca cacacacaca cacacacaca | 3550 |
| cacacacact ggctggtttg ctgatggaac ccttagacca ccctcccacc | 3600 |
| cccacccctc cccaagcatg gctgcaagtg tcagggcacc acaccttcct | 3650 |
| cttcttgaca tttctttgaa cagacatcat tttgtaggat cttaatttat | 3700 |
| acatttttt caggtcataa aatgtgggat gaacatactt tgaacccag | 3750 |
| tgccttcagg gtccattgac tagggaggca ctgtcttagg ggacaggtat | 3800 |
| gtgcaaggcc ttaccacca gtggcttctc gctgcaggtc atgtttgtgg | 3850 |
| cacttgttct ttaaggtgag ggtcttatga ccgactgttc tgagacagcc | 3900 |
| ctgtgtcagg caagctcttt cacagggttg taggtatttc caagacgcca | 3950 |
| taggaaccag acagtgaatc atagctatca gtttgctgtg ggcaaggaac | 4000 |
| ctcttttttgg ccacctggta acaaaatttt atgtctgtaa attttttctt | 4050 |
| gctatttaaa aaaaaaaaaa aaaaa | 4075 |

<210> SEQ ID NO 16
<211> LENGTH: 847
<212> TYPE: DNA
<213> ORGANISM: Mouse

<400> SEQUENCE: 16

| | |
|---|---|
| cgcggtgggc aagaccagcc tggtggtcag ctacaccact aacggctacc | 50 |
| ccaccgagta catccctacg gccttcgaca acttctcggc cgtggtgtct | 100 |
| gtagatgggc ggcctgtgag actccagctc tgtgacactg caggacagga | 150 |
| tgagtttgac aagctgaggc ccctctgcta caccaacaca gacatcttcc | 200 |
| tgctgtgctt cagcgtggtg agccccacat ccttccagaa cgtgggcgag | 250 |
| aagtgggttc cagagattcg acgtcactgc ccaaaggccc ccatcatcct | 300 |
| ggtcgggaca cagtcggacc tcagggagga cgtcaaagtg ctcatagaac | 350 |
| tggcttctgc agggcatctg tgtcctgctg ttaaaagcag gaggaggtgc | 400 |
| ttgtctggga gctttaagtg tgctgggctc atatcgtccc gtttgcaagg | 450 |
| aattgggcca ccttgagagg ccatagttga tggctatggg acacacacac | 500 |
| acttttttcct taagtccacc aaaatgcctg cctgtacaca cacacacaca | 550 |
| cacacacaca cacacacaca cacacactgg ctggtttgct gatggaaccc | 600 |
| ttagaccacc ctcccacccc caccctccc caagcatggc tgcaagtgtc | 650 |
| agggcaccac accttcctct tcttgacatt tctttgaaca gacatcattt | 700 |
| tgtaggatct taatttatac attttttca ggtcataaaa tgtgggatga | 750 |

```
acatactttg aacccagtg ccttcagggt ccattgacta gggaggcact        800
gtcttagggg acaggtatgt gcaaggcctt acccaccagt ggcttct          847
```

<210> SEQ ID NO 17
<211> LENGTH: 1363
<212> TYPE: DNA
<213> ORGANISM: Mouse
<220> FEATURE:
<221> NAME/KEY: Unknown
<222> LOCATION: 504
<223> OTHER INFORMATION: Any nucleotide

<400> SEQUENCE: 17

```
cccacgcgtc cgtatgaaaa tggtggagat gcctcgtaga aggcgagtgc         50
tgggtgcaca tgtgacattt tcttcaggga gcgactcatg gtgagaccag        100
agagggctct tagcttgcag gactggcttc tgcagggcat ctgtgtcctg        150
ctgttaaaag caggaggagg tgcttgtctg ggagctttaa gtgtgctggg        200
ctcatatcgt cccgtttgca aggaattggg ccaccttgag aggccatagt        250
tgatggctat gggacacaca cacactttt ccttaagtcc accaaaatgc         300
ctgcctgtac acacacacac acacacacac acacacacac acacacacac        350
tggctggttt gctgatggaa cccttagacc accctcccac cccacccct         400 ccccaagcat ggctgcaagt gtcagggcac cacaccttcc tcttcttgac        450
atttctttga acagacatca ttttgtagga tcttaattta tacatttttt        500
tcangtcata aaatgtggga tgaacatact ttgaaccccca gtgccttcag       550 ggtccattga ctagggaggc actgtcttag gggacaggta tgtgcaaggc        600
cttacccacc agtggcttct cgctgcaggt catgtttgtg gcacttgttc        650
tttaaggtga gggtcttatg accgactgtt ctgagacagc cctgtgtcag        700
gcaagctctt tcacagggtt gtaggtattt ccaagacgcc ataggaacca        750
gacagtgaat catagctatc agtttgctgt gggcaaggaa cctctttttg        800
gccacctggt aacaaaattt tatgtctgta aattttttct tgctatttaa        850
aaaaaaaaat caatcttacg ttttctgta ggaaaaaaaa aaacaagtaa         900
aagaacaggc catatttcag gtcaaaggct tcttccttct ggtaaatggg        950
actgaagact ttcttacatc attattaaaa ggctaattgc tgaaccacta       1000
gagtatatga actgtttgtg aatgatatta gccatagtct cctgaggtgt       1050
ttccttgtgg cctgagtggt aacattgttt tgcttatgga gatgctgtaa       1100
ctgacctagt gactcagctt atcctattgt gcatggctgt ctggaaagcc       1150
agcgtacaag tggggctttg cctgccctgt gtacagaggg tgggtgggaa       1200
agagtgaatt atttaatttt aaatgttata ataaagccaa tgtagttgag       1250
accaaggaaa tgagcattga gaacacaaac ttgaagtctg gtgccagggt       1300
tgttggacct cacaccctgt ctctgagcca cccggaagtg acataaagga       1350
cgctgtgtga tca                                              1363
```

<210> SEQ ID NO 18
<211> LENGTH: 1953
<212> TYPE: DNA
<213> ORGANISM: Mouse

<400> SEQUENCE: 18

-continued

```
cccacgcgtc cggtgaccag ttatattgct atgaaaatgg tggagatgcc      50
tcgtagaagg cgagtgctgg gtgcacatgt gacattttct tcagggagcg     100
actcatggtg agaccagaga gggctcttag cttgcaggac tggcttctgc     150
agggcatctg tgtcctgctg ttaaaagcag gaggaggtgc ttgtctggga     200
gctttaagtg tgctgggctc atatcgtccc gtttgcaagg aattgggcca     250
ccttgagagg ccatagttga tggctatggg acacacacac acttttttcct    300
taagtccacc aaaatgcctg cctgtacaca cacacacaca cacacacaca     350
cacacacaca cacacactgg ctggtttgct gatggaaccc ttagaccacc     400
ctcccacccc caccccctccc caagcatggc tgcaagtgtc agggcaccac    450
accttcctct tcttgacatt tctttgaaca gacatcattt tgtaggatct     500
aatttataca ttttttttcag gtcataaaat gtgggatgaa catactttga    550
accccagtgc cttcagggtc cattgactag ggaggcactg tcttagggga     600
caggtatgtg caaggcctta cccaccagtg gcttctcgct gcaggtcatg     650
tttgtggcac ttgttcttta aggtgagggt cttatgaccg actgttctga     700
gacagccctg tgtcaggcaa gctctttcac agggttgtag gtatttccaa     750
gacgccatag gaaccagaca gtgaatcata gctatcagtt tgctgtgggc     800
aaggaacctc ttttgggcca cctggtaaca aaatttatg tctgtaaatt      850
ttttcttgct atttaaaaaa aaaatcaat cttacgtttt tctgtaggaa       900
aaaaaaaaac aagtaaaaga acaggccata tttcaggtca aaggcttctt     950
cctgctggta aatgggactg aagactttct tacatcatta ttaaaaggct    1000
aattgctgaa ccactagagt atatgaactg tttgtgaatg atattagcca    1050
tagtctcctg aggtgtttcc ttgtggcctg agtggtaaca ttgttttgct    1100
tatggagatg ctgtaactga cctagtgact cagcttatcc tattgtgcat    1150
ggctgtctgg aaagccagcg tacaagtggg gctttgcctg ccctgtgtac    1200
agagggtggg tgggaaagag tgaattattt aattttaaat gttataataa    1250
agccaatgta gttgagacca aggaaatgag cattgagaac acaaacttga    1300
agtctggtgc cagggttgtt ggacctcaca ccctgtctct gagccacccg    1350
gaagtgacat aaaggacgct gtgtgatcaa gttctggaca cttttctggg    1400
atgcgtacca ctggactatt tatgtcacaa atctagtggg ttgacgctgc    1450
cctgcaagtt ttcaatgtcc ctgcatccta tgaagtcata atgtctgact    1500
gtactggagg ttttcctgca tttttttactt ttcgaaaata gaggtttggg   1550
ctgagaattc taaacgcatg tgcctgggtg ggacgtcaag tcagggttct    1600
catcaaagct gagaagtggc tggaatgttc agcttggtgt ctggggcagg    1650
ctccaaaatc gtcacctcaa gcatgcgtgc aagcaaactt ccgagaactc    1700
cgttttctgc tcggcagacg tgtgagcagc tacccagaag tctcaagcca    1750
aaaggggagc ctcgctcgct ggctcctctg caggtgcctt atcgacctgt    1800
gctcttctct tttcccgtgt caaagatgtt ggacaggatc ttgtacttga    1850
aacatactac aaatgagtta ctatgaaata aattctgacc tgtggaccga    1900
aaaaaaaaaa aaaaaaaaaa aaaaaaaaaa aaaaaaaaaa aaaaaaaaa    1950
```

-continued aaa 1953

<210> SEQ ID NO 19
<211> LENGTH: 841
<212> TYPE: DNA
<213> ORGANISM: Mouse

<400> SEQUENCE: 19

| | |
|---|---|
| cccacgcgtc cgcggacgcg tggttcaggg tccattgact agggaggcac | 50 |
| tgtcttaggg gacaggtatg tgcaaggcct tacccaccag tggcttctcg | 100 |
| ctgcaggtca tgtttgtggc acttgttctt taaggtgagg gtcttatgac | 150 |
| cgactgttct gagacagccc tgtgtcaggc aagctctttc acagggttgt | 200 |
| aggtatttcc aagacgccat aggaaccaga cagtgaatca tagctatcag | 250 |
| tttgctgtgg gcaaggaacc tcttttggc cacctggtaa caaaatttta | 300 |
| tgtctgtaaa ttttttcttg ctatttaaaa aaaaaatca atcttacgtt | 350 |
| tttctgtagg aaaaaaaaaa acaagtaaaa gaacaggcca tatttcaggt | 400 |
| caaaggcttc ttcctgctgg taaatgggac tgaagacttt cttacatcat | 450 |
| tattaaaagg ctaattgctg aaccactaga gtatatgaac tgtttgtgaa | 500 |
| tgatattagc catagtctcc tgaggtgttt ccttgtggcc tgagtggtaa | 550 |
| cattgttttg cttatggaga tgctgtaact gacctagtga ctcagcttat | 600 |
| cctattgtgc atggctgtct ggaaagccag cgtacaagtg gggctttgcc | 650 |
| tgccctgtgt acagagggtg ggtgggaaag agtgaattat ttaattttaa | 700 |
| atgttataat aaagccaatg tagttgagac caaggaaatg agcattgaga | 750 |
| acacaaactt gaagtctggt gccagggttg ttggacctca caccctgtct | 800 |
| ctgagccacc cggaagtgac ataaaggacg ctgtgtgatc a | 841 |

<210> SEQ ID NO 20
<211> LENGTH: 14
<212> TYPE: DNA
<213> ORGANISM: Artificial sequence
<220> FEATURE:
<221> NAME/KEY: Artificial sequence
<222> LOCATION: 1-14
<223> OTHER INFORMATION: Sequence is synthesized

<400> SEQUENCE: 20
ttttgtacaa gctt 14

<210> SEQ ID NO 21
<211> LENGTH: 44
<212> TYPE: DNA
<213> ORGANISM: Artificial sequence
<220> FEATURE:
<221> NAME/KEY: Artificial sequence
<222> LOCATION: 1-44
<223> OTHER INFORMATION: Sequence is synthesized

<400> SEQUENCE: 21
ctaatacgac tcactatagg gctcgagcgg ccgcccgggc aggt 44

<210> SEQ ID NO 22
<211> LENGTH: 43
<212> TYPE: DNA
<213> ORGANISM: Artificial sequence
<220> FEATURE:
<221> NAME/KEY: Artificial sequence
<222> LOCATION: 1-43
<223> OTHER INFORMATION: Sequence is synthesized

<400> SEQUENCE: 22
tgtagcgtga agacgacaga aagggcgtgg tgcggagggc ggt    43

<210> SEQ ID NO 23
<211> LENGTH: 10
<212> TYPE: DNA
<213> ORGANISM: Artificial Sequence
<220> FEATURE:
<221> NAME/KEY: Artificial sequence
<222> LOCATION: 1-10
<223> OTHER INFORMATION: Sequence is synthesized

<400> SEQUENCE: 23
acctgcccgg    10

<210> SEQ ID NO 24
<211> LENGTH: 11
<212> TYPE: DNA
<213> ORGANISM: Artificial sequence
<220> FEATURE:
<221> NAME/KEY: Artificial sequence
<222> LOCATION: 1-11
<223> OTHER INFORMATION: Sequence is synthesized

<400> SEQUENCE: 24
accgccctcc g    11

<210> SEQ ID NO 25
<211> LENGTH: 22
<212> TYPE: DNA
<213> ORGANISM: Artificial sequence
<220> FEATURE:
<221> NAME/KEY: Artificial sequence
<222> LOCATION: 1-22
<223> OTHER INFORMATION: Sequence is synthesized

<400> SEQUENCE: 25
ctaatacgac tcactatagg gc    22

<210> SEQ ID NO 26
<211> LENGTH: 21
<212> TYPE: DNA
<213> ORGANISM: Artificial sequence
<220> FEATURE:
<221> NAME/KEY: Artificial sequence
<222> LOCATION: 1-21
<223> OTHER INFORMATION: Sequence is synthesized

<400> SEQUENCE: 26
tgtagcgtga agacgacaga a    21

<210> SEQ ID NO 27
<211> LENGTH: 22
<212> TYPE: DNA
<213> ORGANISM: Artificial sequence
<220> FEATURE:
<221> NAME/KEY: Artificial sequence
<222> LOCATION: 1-22
<223> OTHER INFORMATION: Sequence is synthesized

<400> SEQUENCE: 27
tcgagcggcc gcccgggcag gt    22

<210> SEQ ID NO 28

```
<211> LENGTH: 22
<212> TYPE: DNA
<213> ORGANISM: Artificial sequence
<220> FEATURE:
<221> NAME/KEY: Artificial sequence
<222> LOCATION: 1-22
<223> OTHER INFORMATION: Sequence is synthesized

<400> SEQUENCE: 28
agggcgtggt gcggagggcg gt                                              22

<210> SEQ ID NO 29
<211> LENGTH: 20
<212> TYPE: DNA
<213> ORGANISM: Artificial sequence
<220> FEATURE:
<221> NAME/KEY: Artificial sequence
<222> LOCATION: 1-20
<223> OTHER INFORMATION: Sequence is synthesized

<400> SEQUENCE: 29
accacagtcc atgccatcac                                                 20

<210> SEQ ID NO 30
<211> LENGTH: 20
<212> TYPE: DNA
<213> ORGANISM: Artificial sequence
<220> FEATURE:
<221> NAME/KEY: Artificial sequence
<222> LOCATION: 1-20
<223> OTHER INFORMATION: Sequence is synthesized

<400> SEQUENCE: 30
tccaccaccc tgttgctgta                                                 20

<210> SEQ ID NO 31
<211> LENGTH: 163
<212> TYPE: DNA
<213> ORGANISM: Artificial sequence
<220> FEATURE:
<221> NAME/KEY: Artificial sequence
<222> LOCATION: 1-163
<223> OTHER INFORMATION: Sequence is synthesized

<400> SEQUENCE: 31
tgtaatacga ctcactatag ggcgaattgg gcccgacgtc gcatgctccc                50
ggccgccatg gccgcgggat tatcactagt gcggccgcct gcaggtcgac                100
catatgggag agctcccaac gcgttggatg catagcttga gtattctata                150
gtgtcaccta aat                                                        163

<210> SEQ ID NO 32
<211> LENGTH: 163
<212> TYPE: DNA
<213> ORGANISM: Artificial sequence
<220> FEATURE:
<221> NAME/KEY: Artificial sequence
<222> LOCATION: 1-163
<223> OTHER INFORMATION: Sequence is synthesized

<400> SEQUENCE: 32
atttaggtga cactatagaa tactcaagct atgcatccaa cgcgttggga                50
gctctcccat atggtcgacc tgcaggcggc cgcactagtg attatcccgc                100
ggccatggcg gccgggagca tgcgacgtcg ggcccaattc gccctatagt                150
gagtcgtatt aca                                                        163
```

<210> SEQ ID NO 33
<211> LENGTH: 24
<212> TYPE: DNA
<213> ORGANISM: Artificial sequence
<220> FEATURE:
<221> NAME/KEY: Artificial sequence
<222> LOCATION: 1-24
<223> OTHER INFORMATION: Sequence is synthesized

<400> SEQUENCE: 33
cagagggtgg gtgggaaaga gtga                                              24

<210> SEQ ID NO 34
<211> LENGTH: 24
<212> TYPE: DNA
<213> ORGANISM: Artificial Sequence
<220> FEATURE:
<221> NAME/KEY: Artificial
<222> LOCATION: 1-24
<223> OTHER INFORMATION: Sequence is synthesized

<400> SEQUENCE: 34
cacagcgtcc tttatgtcac ttcc                                              24

<210> SEQ ID NO 35
<211> LENGTH: 23
<212> TYPE: DNA
<213> ORGANISM: Artificial Sequence
<220> FEATURE:
<221> NAME/KEY: Artificial sequence
<222> LOCATION: 1-23
<223> OTHER INFORMATION: Sequence is synthesized

<400> SEQUENCE: 35
gtggcccatg ctctggcaga ggg                                               23

<210> SEQ ID NO 36
<211> LENGTH: 24
<212> TYPE: DNA
<213> ORGANISM: Artificial sequence
<220> FEATURE:
<221> NAME/KEY: Artificial sequence
<222> LOCATION: 1-24
<223> OTHER INFORMATION: Sequence is synthesized

<400> SEQUENCE: 36
gactggagca aggtcgtcct cgcc                                              24

<210> SEQ ID NO 37
<211> LENGTH: 24
<212> TYPE: DNA
<213> ORGANISM: Artificial sequence
<220> FEATURE:
<221> NAME/KEY: Artificial sequence
<222> LOCATION: 1-24
<223> OTHER INFORMATION: Sequence is synthesized

<400> SEQUENCE: 37
gcaccaccca caaggaagcc atcc                                              24

<210> SEQ ID NO 38
<211> LENGTH: 24
<212> TYPE: DNA
<213> ORGANISM: Artificial sequence
<220> FEATURE:
<221> NAME/KEY: Artificial sequence
<222> LOCATION: 1-24

<223> OTHER INFORMATION: Sequence is synthesized

<400> SEQUENCE: 38
gacgaaaggg aagccggcat cacc                                   24

<210> SEQ ID NO 39
<211> LENGTH: 24
<212> TYPE: DNA
<213> ORGANISM: Artificial sequence
<220> FEATURE:
<221> NAME/KEY: Artificial sequence
<222> LOCATION: 1-24
<223> OTHER INFORMATION: Sequence is synthesized

<400> SEQUENCE: 39
gagaaggtcg tgttcgagca aacc                                   24

<210> SEQ ID NO 40
<211> LENGTH: 24
<212> TYPE: DNA
<213> ORGANISM: Artificial sequence
<220> FEATURE:
<221> NAME/KEY: Artificial sequence
<222> LOCATION: 1-24
<223> OTHER INFORMATION: Sequence is synthesized

<400> SEQUENCE: 40
cttctcgtgt acttcctgtg cctg                                   24

<210> SEQ ID NO 41
<211> LENGTH: 24
<212> TYPE: DNA
<213> ORGANISM: Artificial sequence
<220> FEATURE:
<221> NAME/KEY: Artificial sequence'
<222> LOCATION: 1-24
<223> OTHER INFORMATION: Sequence is synthesized

<400> SEQUENCE: 41
cacgtcagct ggcgttgcca gctc                                   24

<210> SEQ ID NO 42
<211> LENGTH: 50
<212> TYPE: DNA
<213> ORGANISM: Artificial Sequence
<220> FEATURE:
<221> NAME/KEY: Artificial sequence
<222> LOCATION: 1-50
<223> OTHER INFORMATION: Sequence is synthesized

<400> SEQUENCE: 42
caacttctcg gccgtggtgt ctgtagatgg gcggcctgtg agactccagc        50

<210> SEQ ID NO 43
<211> LENGTH: 24
<212> TYPE: DNA
<213> ORGANISM: Artificial sequence
<220> FEATURE:
<221> NAME/KEY: Artificial sequence
<222> LOCATION: 1-24
<223> OTHER INFORMATION: Sequence is synthesized

<400> SEQUENCE: 43
gcacacacgc atggaggcaa gctc                                   24

<210> SEQ ID NO 44
<211> LENGTH: 24

```
<212> TYPE: DNA
<213> ORGANISM: Artificial sequence
<220> FEATURE:
<221> NAME/KEY: Artificial sequence
<222> LOCATION: 1-24
<223> OTHER INFORMATION: Sequence is synthesized

<400> SEQUENCE: 44
gccatcttgt ttacagctcc acca                                          24

<210> SEQ ID NO 45
<211> LENGTH: 50
<212> TYPE: DNA
<213> ORGANISM: Artificial sequence
<220> FEATURE:
<221> NAME/KEY: Artificial sequence
<222> LOCATION: 1-50
<223> OTHER INFORMATION: Sequence is synthesized

<400> SEQUENCE: 45
ctcctgacct ttggggctgc acttcccag gacgaccact gcctgcccac               50

<210> SEQ ID NO 46
<211> LENGTH: 177
<212> TYPE: DNA
<213> ORGANISM: Human

<400> SEQUENCE: 46
gaccctccct ggccgccttt gtctactggc cgtgcggccc ggaaccgcca              50
ctctccaggg ccggggacgc gcccgcagct gtcggtgaca gctcctccct             100
accgcaaccc tccggggcgg aggggcggtc gggccgggcc ctgctagccc             150
gcgaccgcaa gcccgcgctc gcggatc                                      177

<210> SEQ ID NO 47
<211> LENGTH: 774
<212> TYPE: DNA
<213> ORGANISM: Human

<400> SEQUENCE: 47
gaccctccct ggccgccttt gtctactggc cgtgcggccc ggaaccgcca              50
ctctccaggg ccggggacgc gcccgcagct gtcggtgaca gctcctccct             100
accgcaaccc tccggggcgg aggggcggtc gggccgggcc ctgctagccc             150
gcgaccgcaa gcccgcgctc gcggatcgat gccccgcag caggggggacc             200 ccgcgttccc cgaccgctgc gaggcgcctc cggtgccgcc gcgtcgggag             250
cgcggtggac gcggggggacg cgggcctggg gagccggggg gccgggggcg             300 tgcgggggt gccgaggggc gcggcgtcaa gtgcgtgctg gtcggcgacg               350
gcgcggtggg caagacgagc ctggtggtga gttacaccac caacggctac              400
cccaccgagt acatccctac tgccttcgac aacttctccg cggtggtgtc              450
tgtggatggg cggcccgtga gactccaact ctgtgacact gccggacagg              500
atgaatttga caagctgagg cctctctgct acaccaacac agacatcttc              550
ctgctctgct tcagtgtcgt gagccccctca tccttccaga acgtcagtga              600
gaaatgggtg ccggagattc gatgccactg tcccaaagcc cccatcatcc              650
tagttggaac gcagtcggat ctcagagaag atgtcaaagt cctcattgag              700
ttggacaaat gcaaagaaaa gccagtgcct gaagaggcgg ctaagctgtg              750
```
cgccgaggaa atcaaagccg cctc                                                  774

<210> SEQ ID NO 48
<211> LENGTH: 840
<212> TYPE: DNA
<213> ORGANISM: Human

<400> SEQUENCE: 48
caacttctcc gcggtggtgt ctgtggatgg gcggcccgtg agactccaac              50
tctgtgacac tgccggacag gatgaatttg acaagctgag gcctctctgc             100
tacaccaaca cagacatctt cctgctctgc ttcagtgtcg tgagcccctc             150
atccttccag aacgtcagtg agaaatgggt gccggagatt cgatgccact             200
gtcccaaagc ccccatcatc ctagttggaa cgcagtcgga tctcagagaa             250
gatgtcaaag tcctcattga gttggacaaa tgcaaagaaa agccagtgcc             300
tgaagaggcg gctaagctgt gcgccgagga aatcaaagcc gcctcctaca             350
tcgagtgttc agccttgact caaaaaaacc tcaaagaggt ctttgatgca             400
gccatcgtcg ctggcattca atactcggac actcagcaac agccaaagaa             450
gtctaaaagc aggactccag ataaaatgaa aaacctctcc aagtcctggt             500
ggaagaagta ctgctgtttc gtatgatgct ggcaagacac ccagaaaggc             550
tattttcaga tgaaatcgat attagaagct atattagctg aaacaactcc             600
ttttactgcg tagaacctat atcgagagtg tgtgtatatg tattatagga             650
ggagctctca attttatgta ttctttctgc ctttaatttt cttgtttgtt             700
tgagcttagg gatgagatac ttatgcaaga tattttttgaa gtaaattaaa            750
cattttttcac atctctggaa atttagagtt ctagacctct ggttaattta            800
tatctaatat gaagaagaca cctctaatct ggatgttaag                        840

<210> SEQ ID NO 49
<211> LENGTH: 47
<212> TYPE: DNA
<213> ORGANISM: Artificial sequence
<220> FEATURE:
<221> NAME/KEY: Artificial sequence
<222> LOCATION: 1-47
<223> OTHER INFORMATION: Sequence is synthesized

<400> SEQUENCE: 49
ggattctaat acgactcact atagggcagc gttgactcag aaaaacc                 47

<210> SEQ ID NO 50
<211> LENGTH: 48
<212> TYPE: DNA
<213> ORGANISM: Artificial sequence
<220> FEATURE:
<221> NAME/KEY: Artificial sequence
<222> LOCATION: 1-48
<223> OTHER INFORMATION: Sequence is synthesized

<400> SEQUENCE: 50
ctatgaaatt aaccctcact aaagggagca tatgaatttc agccctaa                48

<210> SEQ ID NO 51
<211> LENGTH: 48
<212> TYPE: DNA
<213> ORGANISM: Artificial sequence
<220> FEATURE:
<221> NAME/KEY: Artificial sequence

```
-continued

<222> LOCATION: 1-48
<223> OTHER INFORMATION: Sequence is synthesized

<400> SEQUENCE: 51
ggattctaat acgactcact atagggcacg cacatctgtt tccgtttt                    48

<210> SEQ ID NO 52
<211> LENGTH: 47
<212> TYPE: DNA
<213> ORGANISM: Artificial sequence
<220> FEATURE:
<221> NAME/KEY: Artificial sequence
<222> LOCATION: 1-47
<223> OTHER INFORMATION: Sequence is synthesized

<400> SEQUENCE: 52
ctatgaaatt aaccctcact aaagggacca tccccgctct ctaccta                     47
```